United States Patent
McDevitt et al.

(10) Patent No.: US 9,277,945 B2
(45) Date of Patent: Mar. 8, 2016

(54) METHOD AND APPARATUS FOR TREATING A BONE FRACTURE

(71) Applicant: MNR Device Corporation, Durham, NC (US)

(72) Inventors: Dennis McDevitt, Raleigh, NC (US); Vince Novak, Durham, NC (US); Hadley Callaway, Raleigh, NC (US)

(73) Assignee: MNR Device Corporation, Durham, NC (US)

( * ) Notice: Subject to any disclaimer, the term of this patent is extended or adjusted under 35 U.S.C. 154(b) by 0 days.

(21) Appl. No.: 13/762,054

(22) Filed: Feb. 7, 2013

(65) Prior Publication Data

US 2013/0204250 A1     Aug. 8, 2013

Related U.S. Application Data

(60) Provisional application No. 61/596,056, filed on Feb. 7, 2012, provisional application No. 61/669,852, filed on Jul. 10, 2012, provisional application No. 61/699,387, filed on Sep. 11, 2012, provisional application No. 61/699,715, filed on Sep. 11, 2012, provisional application No. 61/706,385, filed on Sep. 27, 2012.

(51) Int. Cl.
*A61B 17/72* (2006.01)
*A61B 17/84* (2006.01)
(Continued)

(52) U.S. Cl.
CPC ......... *A61B 17/7233* (2013.01); *A61B 17/0401* (2013.01); *A61B 17/1717* (2013.01);
(Continued)

(58) Field of Classification Search
CPC .............. A61B 17/72–17/748; A61B 17/0401; A61B 2017/0404; A61B 2017/0406; A61B 2017/0409; A61B 2017/0459; A61B 5/6837
USPC .............................. 606/62–68, 232, 228, 148
See application file for complete search history.

(56) References Cited

U.S. PATENT DOCUMENTS

| 2,765,787 A | 10/1956 | Pellet |
| 3,433,220 A | 3/1969 | Zickel |

(Continued)

FOREIGN PATENT DOCUMENTS

| EP | 0824893 | 2/1998 |
| EP | 1486175 | 12/2004 |

(Continued)

OTHER PUBLICATIONS

Arthrex, Inc., Humeral SuturePlate: Proximal Humeral Fracture Management System, Product Brochure, 2012, United States.

(Continued)

*Primary Examiner* — Jacqueline Johanas
(74) *Attorney, Agent, or Firm* — Pandiscio & Pandiscio

(57) ABSTRACT

Apparatus for treating a bone fracture, the apparatus including an anchoring tube having a hollow elongated shaft adapted for disposition in a hole formed in a bone and having a distal end, a proximal end and a lumen extending therebetween, and a substantially planar plate mounted to the proximal end of the hollow elongated shaft and adapted for disposition against the outer surface of the bone; wherein the plate has a top surface and a bottom surface, and further wherein the bottom surface of the plate is convex, such that when the anchoring tube is disposed in a hole formed in a bone and is rotated about the longitudinal axis of the hollow elongated shaft, the convex bottom surface of the plate maintains supporting contact with the outer surface of the bone.

32 Claims, 66 Drawing Sheets

(51) Int. Cl.
*A61B 17/88* (2006.01)
*A61B 17/17* (2006.01)
*A61B 17/04* (2006.01)
*A61B 17/80* (2006.01)

(52) U.S. Cl.
CPC .............. *A61B17/1725* (2013.01); *A61B 17/72* (2013.01); *A61B 17/7266* (2013.01); *A61B 17/88* (2013.01); *A61B 17/8872* (2013.01); *A61B 17/808* (2013.01); *A61B 2017/0404* (2013.01); *A61B 2017/0409* (2013.01); *A61B 2017/0496* (2013.01)

(56) References Cited

U.S. PATENT DOCUMENTS

| | | | |
|---|---|---|---|
| 3,530,854 A | 9/1970 | Kearney | |
| 3,709,218 A | 1/1973 | Halloran | |
| 4,522,200 A * | 6/1985 | Stednitz | 606/63 |
| 4,622,959 A | 11/1986 | Marcus | |
| 4,823,794 A * | 4/1989 | Pierce | 606/232 |
| 5,041,114 A | 8/1991 | Chapman et al. | |
| 5,454,823 A | 10/1995 | Richardson et al. | |
| 5,484,438 A | 1/1996 | Pennig | |
| 5,776,194 A | 7/1998 | Mikol et al. | |
| 6,102,953 A * | 8/2000 | Huebner | A61F 2/40 623/19.11 |
| 6,168,627 B1 * | 1/2001 | Huebner | A61F 2/40 606/86 R |
| 6,514,274 B1 | 2/2003 | Boucher et al. | |
| 6,558,388 B1 | 5/2003 | Bartsch et al. | |
| 7,306,626 B2 | 12/2007 | Whelan | |
| 7,569,059 B2 | 8/2009 | Cerundolo | |
| 7,655,009 B2 | 2/2010 | Grusin | |
| 7,713,300 B2 * | 5/2010 | Meridew et al. | 623/13.14 |
| 7,771,441 B2 | 8/2010 | Cerundolo | |
| 7,793,459 B1 | 9/2010 | Ruzicka | |
| 7,833,230 B2 | 11/2010 | Cerundolo | |
| 7,914,532 B2 | 3/2011 | Shaver et al. | |
| 7,914,533 B2 * | 3/2011 | Nelson et al. | 606/64 |
| 7,955,341 B2 | 6/2011 | Cerundolo | |
| 8,088,128 B2 * | 1/2012 | May et al. | 606/64 |
| 8,109,936 B2 | 2/2012 | Tipirneni | |
| RE43,482 E * | 6/2012 | Mikol et al. | 623/22.42 |
| 8,287,538 B2 * | 10/2012 | Brenzel et al. | 606/62 |
| 8,382,835 B2 * | 2/2013 | Meridew et al. | 623/13.14 |
| 8,486,071 B2 | 7/2013 | Jensen et al. | |
| 8,496,657 B2 * | 7/2013 | Bonutti et al. | 606/62 |
| 8,906,022 B2 * | 12/2014 | Krinke et al. | 606/63 |
| 8,926,661 B2 * | 1/2015 | Sikora et al. | 606/232 |
| 8,961,518 B2 | 2/2015 | Taylor et al. | |
| 2002/0049445 A1 | 4/2002 | Hall, IV et al. | |
| 2003/0236555 A1 * | 12/2003 | Thornes | 606/232 |
| 2004/0127907 A1 * | 7/2004 | Dakin et al. | 606/72 |
| 2006/0264952 A1 * | 11/2006 | Nelson et al. | 606/72 |
| 2009/0069812 A1 * | 3/2009 | Gillard et al. | 606/62 |
| 2009/0138014 A1 * | 5/2009 | Bonutti | 606/64 |
| 2009/0182336 A1 * | 7/2009 | Brenzel et al. | 606/62 |
| 2010/0106194 A1 * | 4/2010 | Bonutti et al. | 606/279 |
| 2011/0046625 A1 | 2/2011 | Boileau et al. | |
| 2011/0087227 A1 * | 4/2011 | Mazur et al. | 606/62 |
| 2011/0137313 A1 * | 6/2011 | Jensen et al. | 606/64 |
| 2011/0218626 A1 * | 9/2011 | Krinke et al. | 623/16.11 |
| 2012/0089143 A1 | 4/2012 | Martin et al. | |
| 2012/0191142 A1 * | 7/2012 | Bouduban et al. | 606/331 |
| 2012/0245642 A1 | 9/2012 | Giannoudis et al. | |
| 2013/0172944 A1 * | 7/2013 | Fritzinger et al. | 606/286 |
| 2013/0267953 A1 * | 10/2013 | Brenzel et al. | 606/62 |
| 2014/0128870 A1 * | 5/2014 | Brenzel et al. | 606/62 |
| 2014/0155944 A1 * | 6/2014 | Truman | 606/324 |

FOREIGN PATENT DOCUMENTS

| | | |
|---|---|---|
| EP | 1 700 572 | 9/2006 |
| EP | 1 797 835 | 9/2006 |
| WO | WO 01/97677 | 12/2001 |
| WO | WO 03/007799 | 1/2003 |
| WO | WO 2004/039271 | 5/2004 |
| WO | WO 2006/115782 | 11/2006 |
| WO | WO 2007/035440 | 3/2007 |
| WO | WO 2010/017990 | 2/2010 |

OTHER PUBLICATIONS

Rowles DJ et al., Percutaneous pinning of the proximal part of the humerus. An anatomic study., The Journal of Bone & Joint Surgery Am, Nov. 2001; 83:1695-1699.

Orthopedic Sciences, Inc., TSY Shoulder Plate Bone Graft Stabilization System: Endoscopically Guided Subchondral Intraosseous Osteotomy and Bone Graft Stabilization of the Humeral Head, 2005.

* cited by examiner ures for improved bone screw placement, etc. However, these recent innovations in proximal humeral fracture fixation have not adequately addressed all of the clinical issues faced by the physician.

Significantly, the number of proximal humeral fractures occurring in osteopenic patients (particularly women) is growing. Treating proximal humeral fractures in osteopenic patients is even more challenging than treating proximal humeral fractures in non-osteopenic patients, due to the poor bone quality common in osteopenic patients. Furthermore, increasing numbers of these fractures are being treated in ambulatory surgical settings, which require the physician to treat the patient using less invasive techniques. Current approaches for treating proximal humeral fractures in osteopenic patients have proven inadequate, particularly where minimally invasive techniques must be used.

Thus there is a need for a new and improved method and apparatus for treating bone fractures in general, and for treating proximal humeral fractures in particular.

SUMMARY OF THE INVENTION

The present invention provides a novel method and apparatus for treating bone fractures in general, and for treating proximal humeral fractures in particular.

In one form of the invention, there is provided apparatus for treating a bone fracture, the apparatus comprising:

an anchoring tube comprising a hollow elongated shaft adapted for disposition in a hole formed in a bone and having a distal end, a proximal end and a lumen extending therebetween, and a substantially planar plate mounted to the proximal end of the hollow elongated shaft and adapted for disposition against the outer surface of the bone;

wherein the plate comprises a top surface and a bottom surface, and further wherein the bottom surface of the plate is convex, such that when the anchoring tube is disposed in a hole formed in a bone and is rotated about the longitudinal axis of the hollow elongated shaft, the convex bottom surface of the plate maintains supporting contact with the outer surface of the bone.

In another form of the invention, there is provided apparatus for treating a bone fracture, the apparatus comprising:

an anchoring tube comprising a hollow elongated shaft adapted for disposition in a hole formed in a bone and having a distal end, a proximal end and a lumen extending therebetween, and a substantially planar plate mounted to the proximal end of the hollow elongated shaft and adapted for disposition against the outer surface of the bone;

wherein the hollow elongated shaft comprises at least two diametrically-opposed holes extending therethrough; and a suture assembly extending through a bone fragment, through at least one of the diametrically-opposed holes in the hollow elongated shaft, and through the lumen of the anchoring tube, the suture assembly securing the bone fragment to the anchoring tube under tension, whereby to secure the bone fragment to the bone receiving the anchoring tube.

In another form of the invention, there is provided apparatus for treating a bone fracture, the apparatus comprising:

an anchoring tube comprising a hollow elongated shaft adapted for disposition in a hole formed in a bone and having a distal end, a proximal end and a lumen extending therebetween, and a substantially planar plate mounted to the proximal end of the hollow elongated shaft and adapted for disposition against the outer surface of the bone;

wherein the hollow elongated shaft comprises at least two diametrically-opposed holes extending therethrough;

a breakaway rod for disposition within the lumen of the hollow elongated shaft, the breakaway rod comprising a distal end, a proximal end, a hole proximal to the distal end for alignment with at least two diametrically-opposed holes formed in the hollow elongated shaft, and a breakaway section proximal to the hole formed in the breakaway rod; and a fixation element for extending through a bone fragment, through two diametrically-opposed holes in the hollow elongated shaft, and through the hole in the breakaway rod for securing the bone fragment to the anchoring tube, whereby to secure the bone fragment to the bone receiving the anchoring tube.

In another form of the invention, there is provided apparatus for treating a bone fracture, the apparatus comprising:

a suture assembly comprising a suture and a buckle for mounting to the suture, wherein the buckle comprises a plate having two holes formed therein, a bridge extending between the two holes, and a slot connecting one of the two holes to a perimeter of the plate.

In another form of the invention, there is provided apparatus for treating a bone fracture, the apparatus comprising:

a suture assembly comprising a suture and a buckle, the buckle comprising means for attaching a closed end of the suture to the buckle without tying.

In another form of the invention, there is provided a buckle holder for holding a buckle while suture is secured to the buckle, wherein the buckle has two holes therein and a slot connecting one of the holes to an end of the buckle, the buckle holder comprising a body having a proximal end, a distal end, a top surface and a bottom surface, a pair of holes extending from the top surface to the bottom surface, a buckle seat adjacent the distal end and extending proximally, and a vertical slot opening on the distal end and extending proximally, the vertical slot extending between the top surface and the bottom surface, the buckle holder being sized so that the buckle seat can receive the buckle, with the two holes in the buckle being aligned with the two holes in the buckle holder.

In another form of the invention, there is provided a method for treating a bone fracture, the method comprising:

providing an anchoring tube comprising a hollow elongated shaft adapted for disposition in a hole formed in a bone and having a distal end, a proximal end and a lumen extending therebetween, and a substantially planar plate mounted to the proximal end of the hollow elongated shaft and adapted for disposition against the outer surface of the bone;

wherein the plate comprises a top surface and a bottom surface, and further wherein the bottom surface of the plate is convex, such that when the anchoring tube is disposed in a hole formed in a bone and is rotated about the longitudinal axis of the hollow elongated shaft, the convex bottom surface of the plate maintains supporting contact with the outer surface of the bone;

forming a hole in the bone;

positioning the hollow elongated shaft of the anchoring tube in the hole in the bone; and rotating the anchoring tube about the longitudinal axis of the hollow elongated shaft while the convex bottom surface of the plate maintains supporting contact with the outer surface of the bone.

In another form of the invention, there is provided a method for treating a bone fracture, the method comprising:

providing apparatus comprising:

an anchoring tube comprising a hollow elongated shaft adapted for disposition in a hole formed in a bone and having a distal end, a proximal end and a lumen extending therebetween, and a substantially planar plate mounted to the proximal end of the hollow elongated shaft and adapted for disposition against the outer surface of the bone;

wherein the hollow elongated shaft comprises at least two diametrically-opposed holes extending therethrough; and a suture assembly extending through a bone fragment, through at least one of the diametrically-opposed holes in the hollow elongated shaft, and through the lumen of the anchoring tube, the suture assembly securing the bone fragment to the anchoring tube under tension, whereby to secure the bone fragment to the bone receiving the anchoring tube;

forming a hole in the bone;

positioning the hollow elongated shaft of the anchoring tube in the hole in the bone; and extending a suture assembly through a bone fragment, through at least one of the diametrically-opposed holes in the hollow elongated shaft, and through the lumen of the anchoring tube, the suture assembly securing the bone fragment to the anchoring tube under tension, whereby to secure the bone fragment to the bone receiving the anchoring tube.

In another form of the invention, there is provided a method for treating a bone fracture, the method comprising:

providing apparatus comprising:

an anchoring tube comprising a hollow elongated shaft adapted for disposition in a hole formed in a bone and having a distal end, a proximal end and a lumen extending therebetween, and a substantially planar plate mounted to the proximal end of the hollow elongated shaft and adapted for disposition against the outer surface of the bone;

wherein the hollow elongated shaft comprises at least two diametrically-opposed holes extending therethrough;

a breakaway rod for disposition within the lumen of the hollow elongated shaft, the breakaway rod comprising a distal end, a proximal end, a hole proximal to the distal end for alignment with at least two diametrically-opposed holes formed in the hollow elongated shaft, and a breakaway section proximal to the hole formed in the breakaway rod; and a fixation element for extending through a bone fragment, through two diametrically-opposed holes in the hollow elongated shaft, and through the hole in the breakaway rod for securing the bone fragment to the anchoring tube, whereby to secure the bone fragment to the bone receiving the anchoring tube;

forming a hole in the bone;

positioning the breakaway rod within the lumen of the hollow elongated shaft, and positioning the hollow elongated shaft of the anchoring tube in the hole in the bone; and extending a fixation element through a bone fragment, through two diametrically-opposed holes in the hollow elongated shaft, and through the hole in the breakaway rod, the fixation element securing the bone fragment to the anchoring tube, whereby to secure the bone fragment to the bone receiving the anchoring tube.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE INVENTION

Fracture Fixation with Suture Assembly

Figure 1:
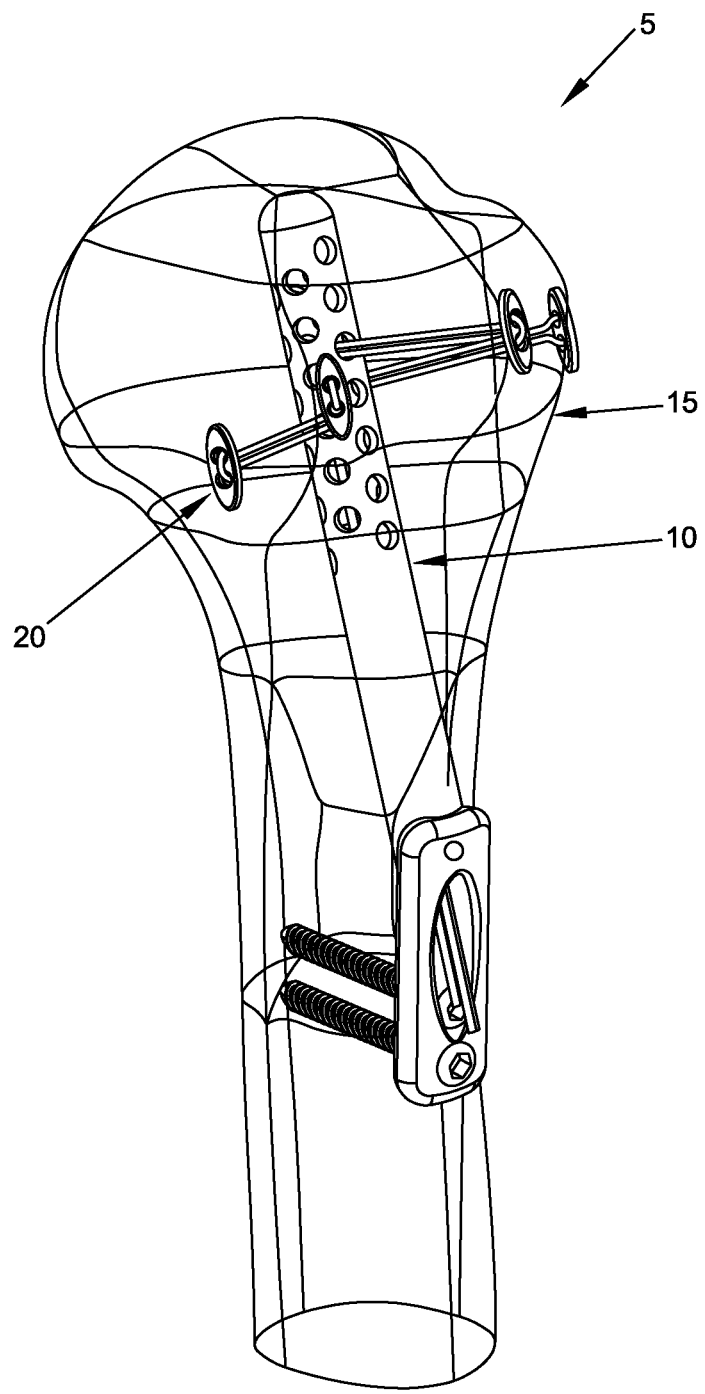
FIG. 1 is a schematic view showing fracture fixation in the proximal humerus using novel fracture fixation apparatus formed in accordance with the present invention.
Figure 2:
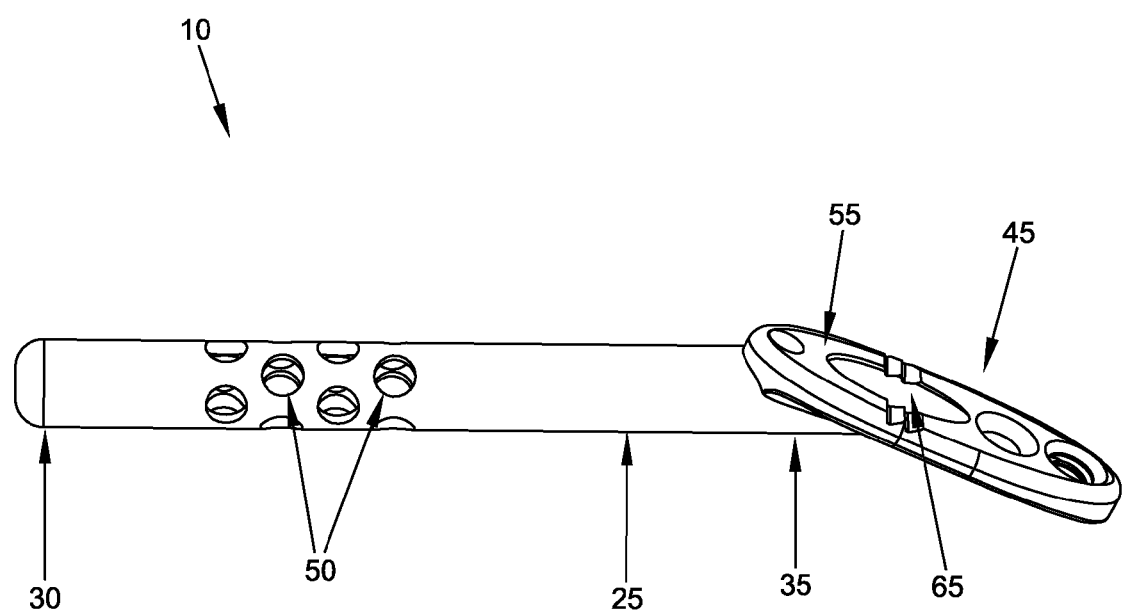
FIGS. 2-7 are schematic views showing details of the anchoring tube of the novel fracture fixation apparatus shown in FIG. 1.
Figure 3:
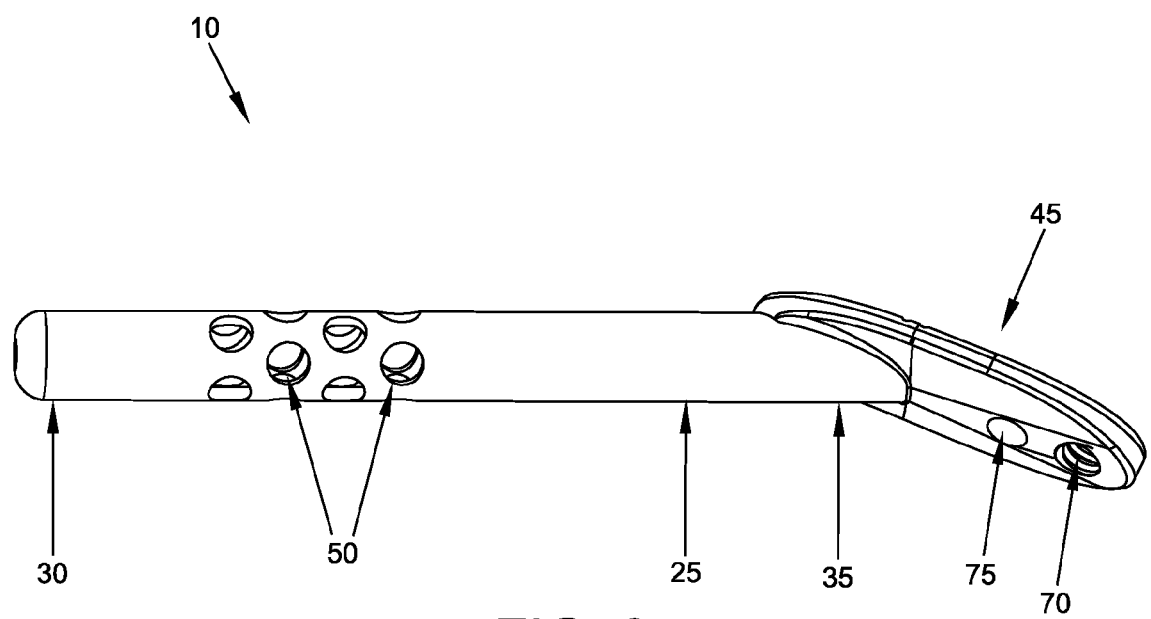
Figure 4:
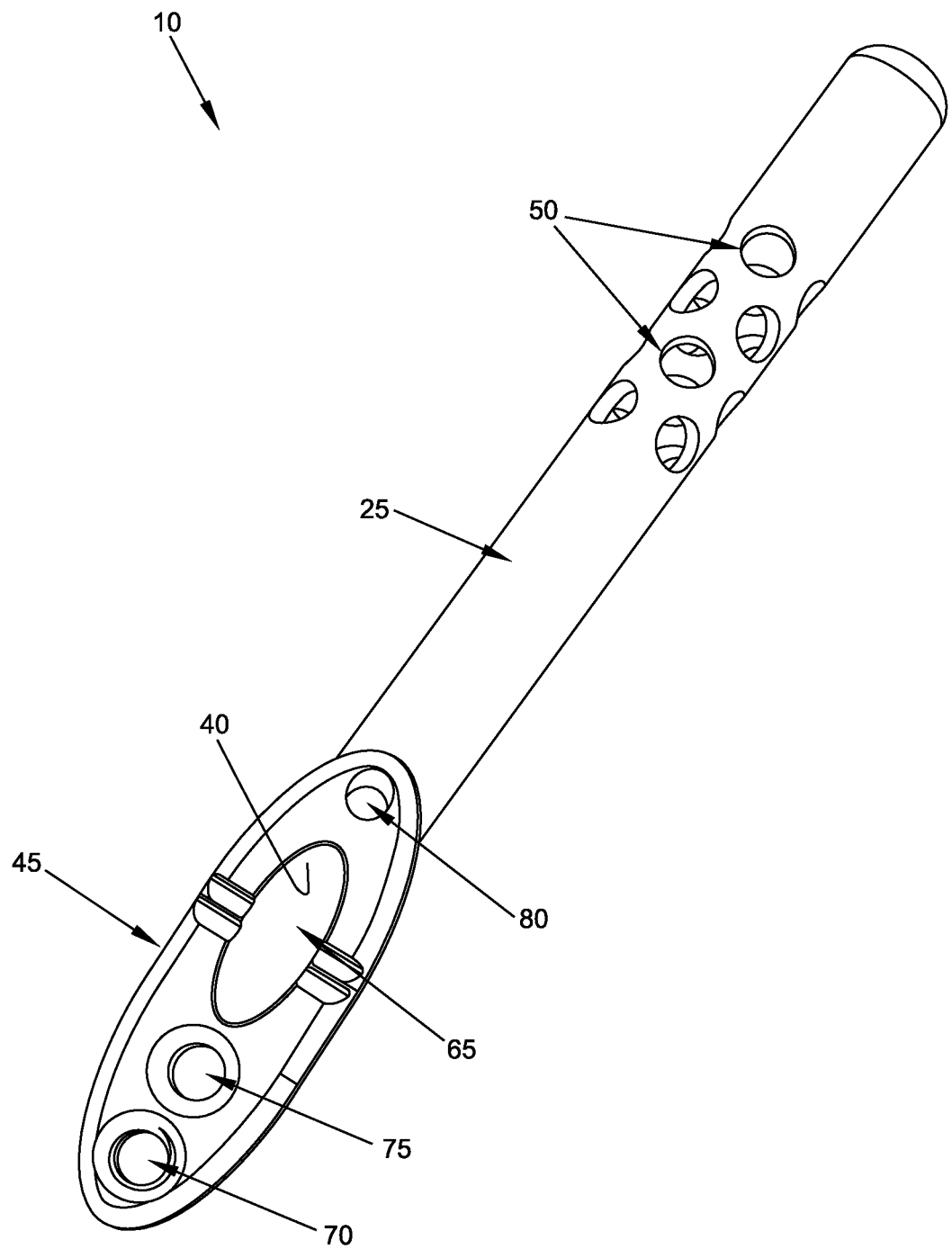
Figure 5:
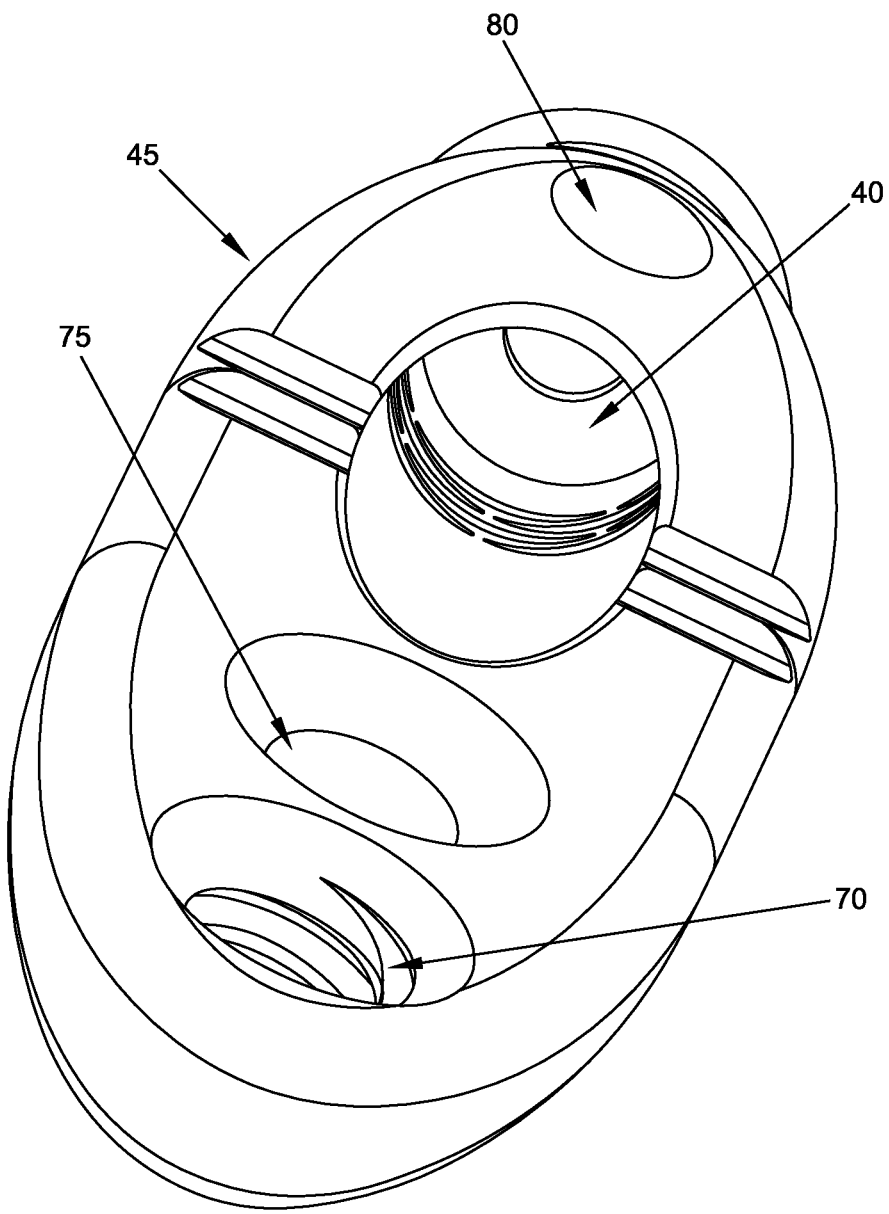
Figure 6:
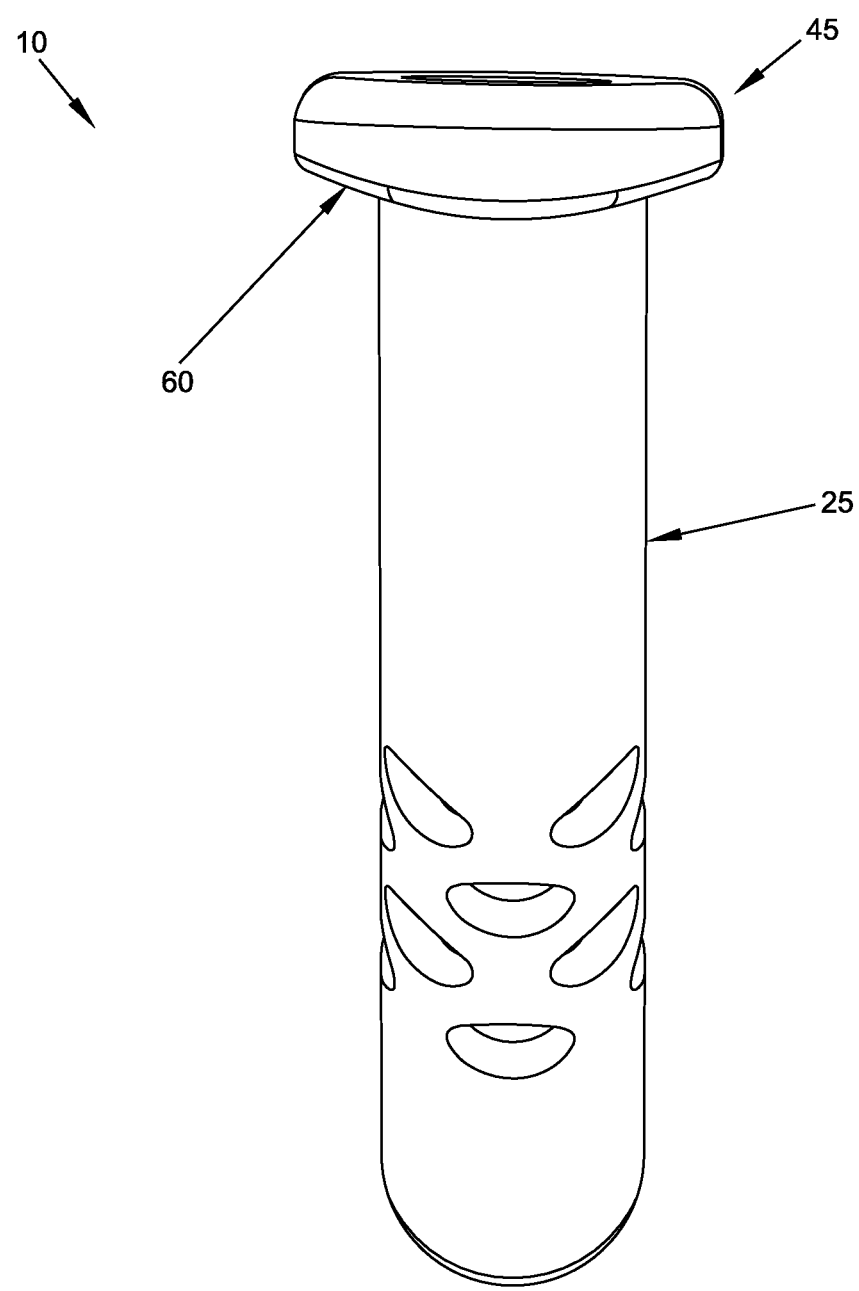
Figure 7:
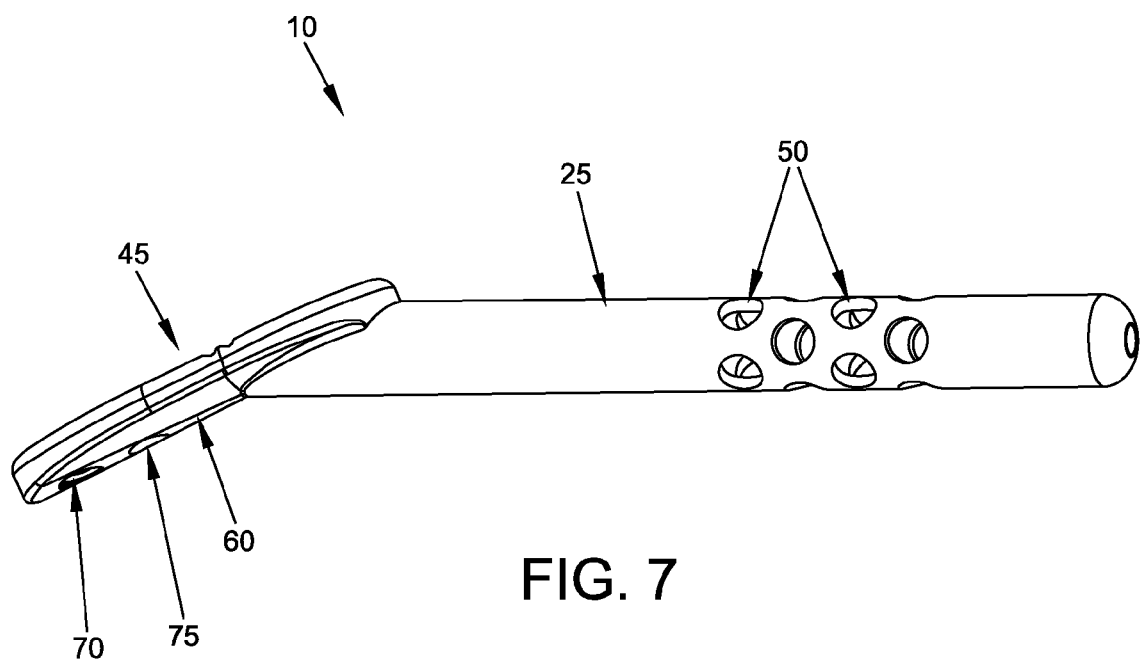

Looking first at FIG. 1, there is shown novel fracture fixation apparatus 5 for treating bone fractures in general, and for treating proximal humeral fractures in particular. As seen in FIG. 1, novel fracture fixation apparatus 5 generally comprises an anchoring tube 10 for disposition in a proximal humerus 15, and one or more suture assemblies 20 for securing bone fragments to anchoring tube 10 and, as a result, for securing bone fragments to proximal humerus 15.

Anchoring tube 10 is shown in greater detail in FIGS. 2-7. Anchoring tube 10 generally comprises a hollow elongated shaft 25 having a distal end 30, a proximal end 35 and a lumen 40 extending therebetween, and a generally planar plate 45 mounted to proximal end 35 of hollow elongated shaft 25. In one form of the invention, plate 45 is formed integral with hollow elongated shaft 25. Plate 45 is mounted to proximal end 35 of hollow elongated shaft 25 so that the plane of plate 45 extends at an angle of approximately 15-45 degrees, and preferably 25 degrees, to the longitudinal axis of hollow elongated shaft 25. Hollow elongated shaft 25 has a plurality of holes 50 extending transversely therethrough. Holes 50 are formed so that for every hole 50, there is a diametrically opposing hole 50. Plate 45 has a substantially flat upper surface 55 and a convex lower surface 60. Plate 45 has a recess 65 formed in its upper surface 55. Recess 65 communicates with interior lumen 40 of hollow elongated shaft 25. Plate 45 also has three holes 70, 75, 80 extending transversely therethrough. More particularly, holes 70 and 75 extend from upper surface 55 of plate 45 to lower surface 60 of plate 45. Hole 80 extends from upper surface 55 of plate 45 to lumen 40 of hollow elongated shaft 25.

Figure 8:
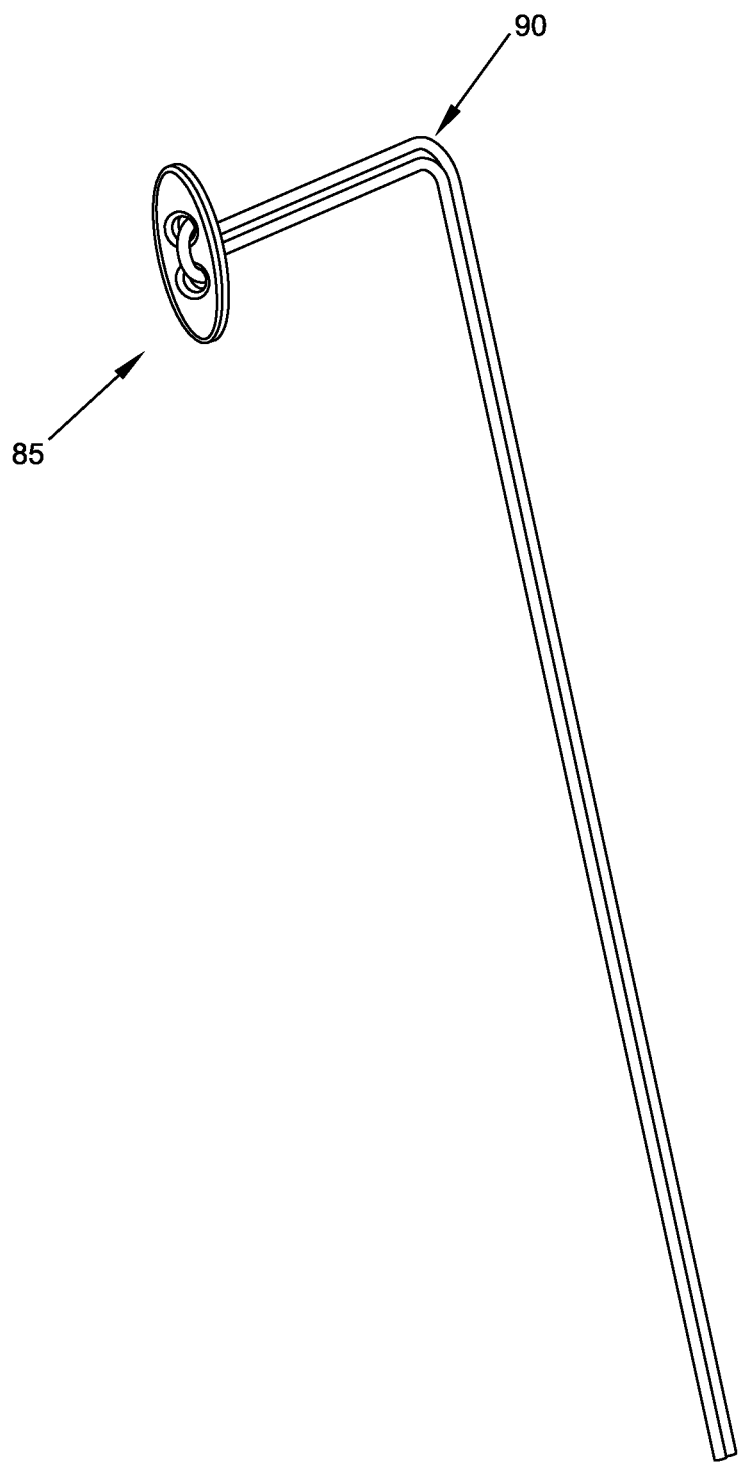
FIGS. 8 and 9 are schematic views showing details of the suture assemblies of the novel fracture fixation apparatus shown in FIG. 1.
Figure 9:
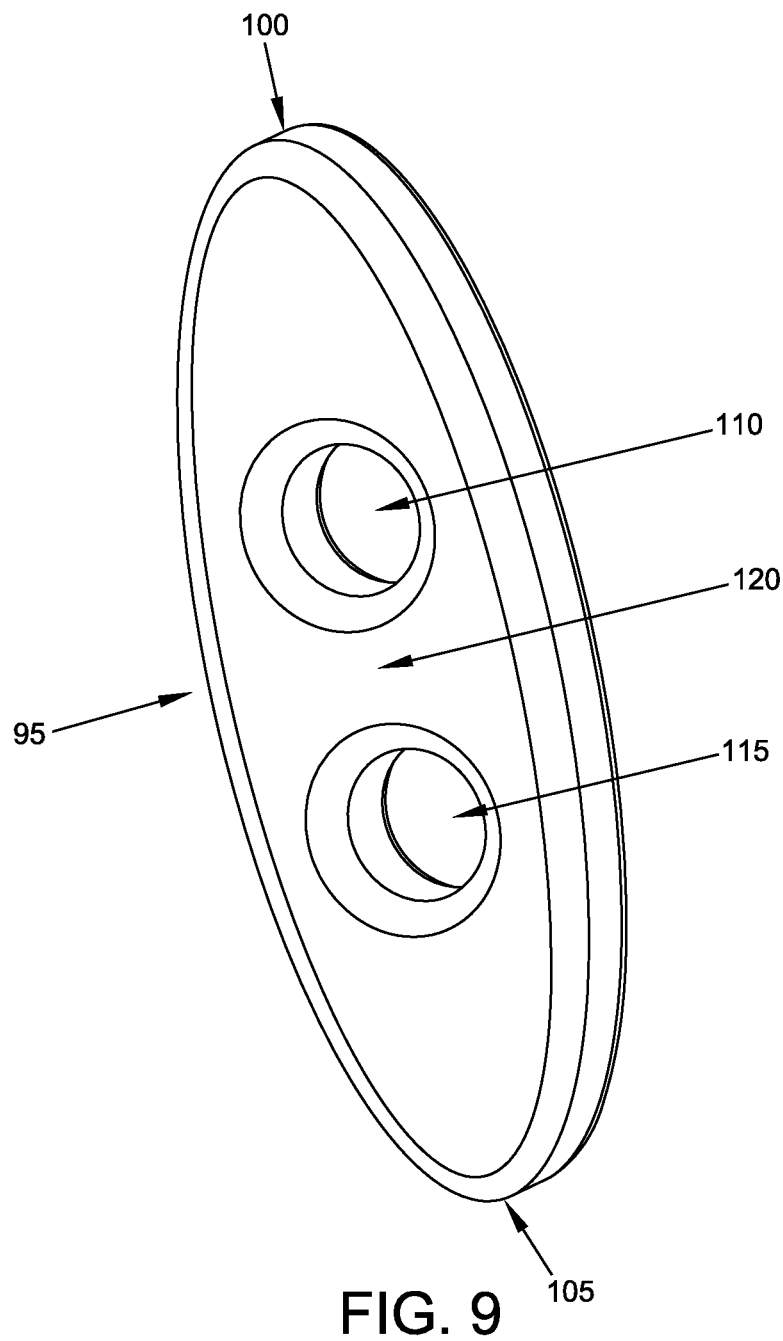

One of the suture assemblies 20 is shown in greater detail in FIGS. 8 and 9. More particularly, each suture assembly 20 comprises a buckle 85 and a suture 90. As seen in FIGS. 8 and 9, buckle 85 comprises an elongated body 95 having a first end 100 and a second end 105, and a first hole 110 and a second hole 115. A bridge 120 is disposed between first hole 110 and second hole 115.

As seen in FIG. 1, anchoring tube 10 of fracture fixation apparatus 5 is intended to be disposed in proximal humerus 15, and the one or more suture assemblies 20 of fracture fixation apparatus 5 are intended to secure bone fragments to anchoring tube 10 and, as a result, to proximal humerus 15. To this end, various instrumentation is provided in order to appropriately deploy fracture fixation apparatus 5 in proximal humerus 15. More particularly, in one preferred form of the invention, this instrumentation comprises:

(i) a lateral entry drill guide 125 (FIGS. 10-12) for forming a hole in proximal humerus 15 for receiving anchoring tube 10;

(ii) an inserter 130 (FIGS. 13-15) for inserting anchoring tube 10 in the hole formed in proximal humerus 15;

(iii) a hoop guide 135 (FIG. 16) for providing information about the disposition of holes 50 in anchoring tube 10 when anchoring tube 10 is disposed in proximal humerus 15;

(iv) a crossbore aimer 140 (FIGS. 17-19) for forming crossbores through proximal humerus 15; and (v) a suture retriever 145 (FIG. 20) for pulling suture through anchoring tube 10.

Figure 10:
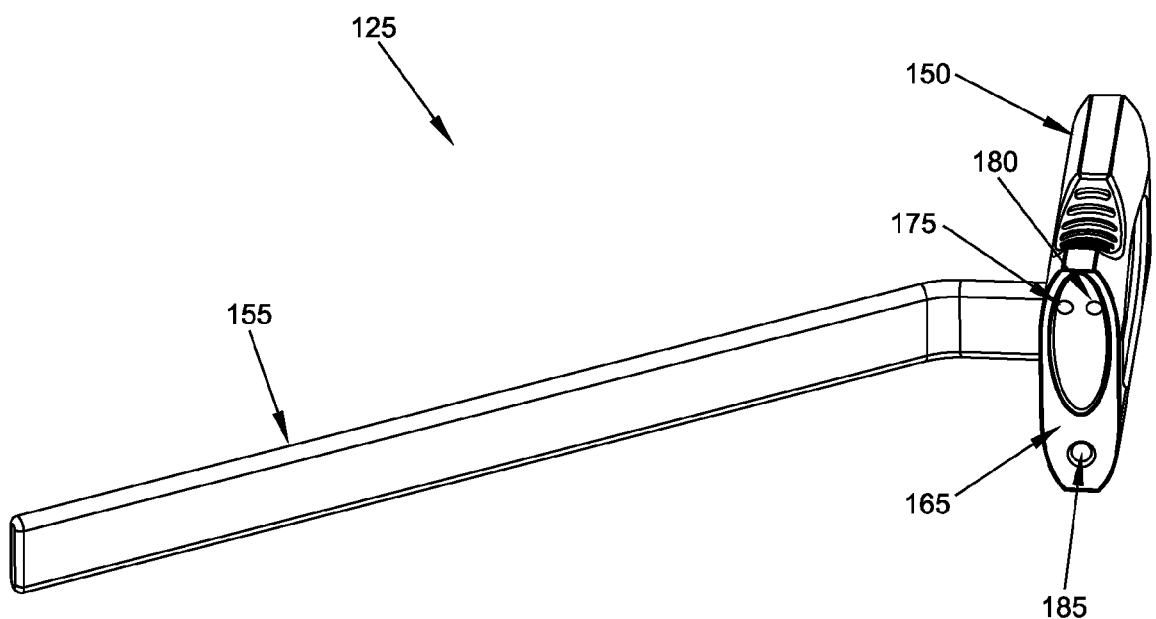
FIGS. 10-12 are schematic views showing a lateral entry drill guide which may be used in conjunction with the novel fracture fixation apparatus shown in FIG. 1.
Figure 11:
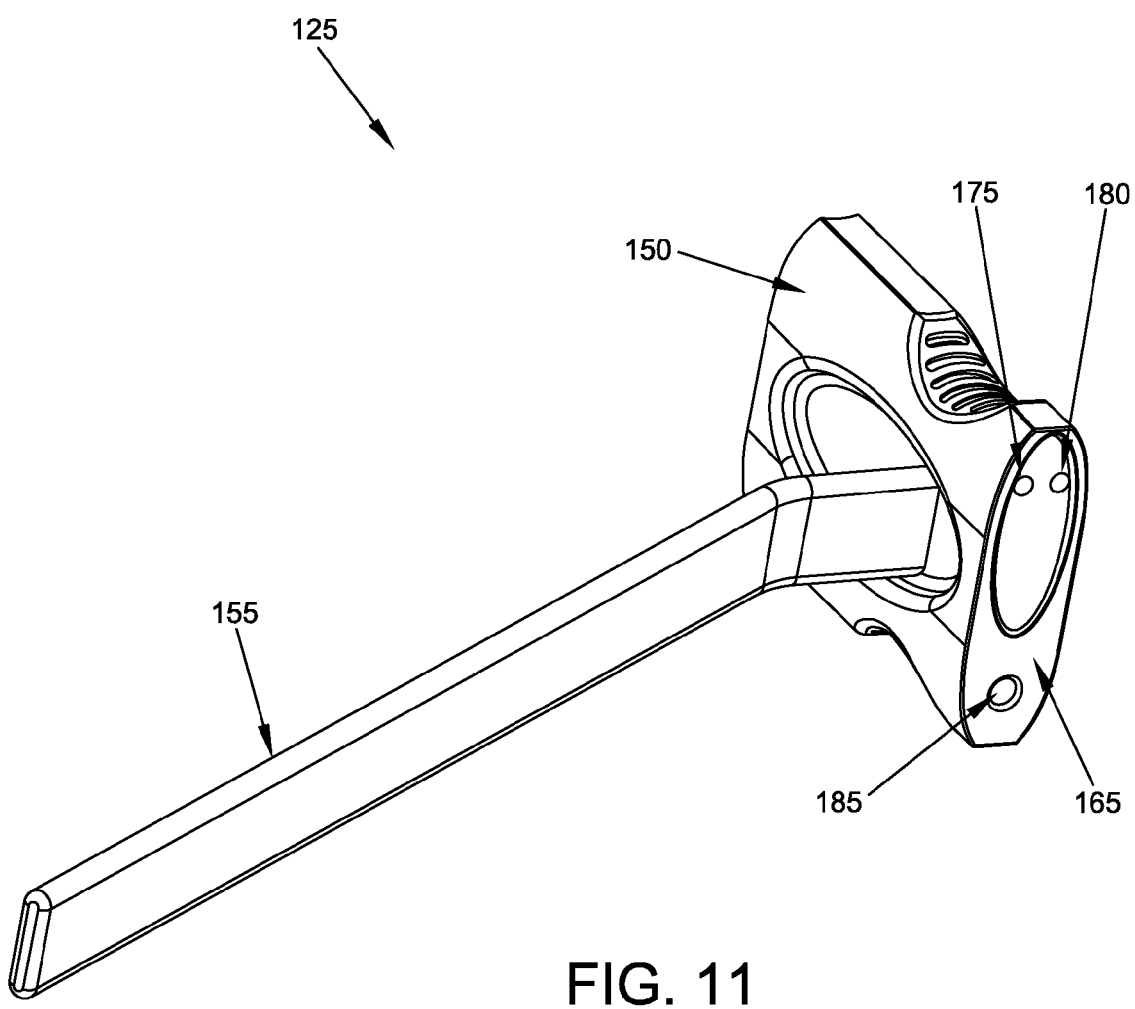
Figure 12:
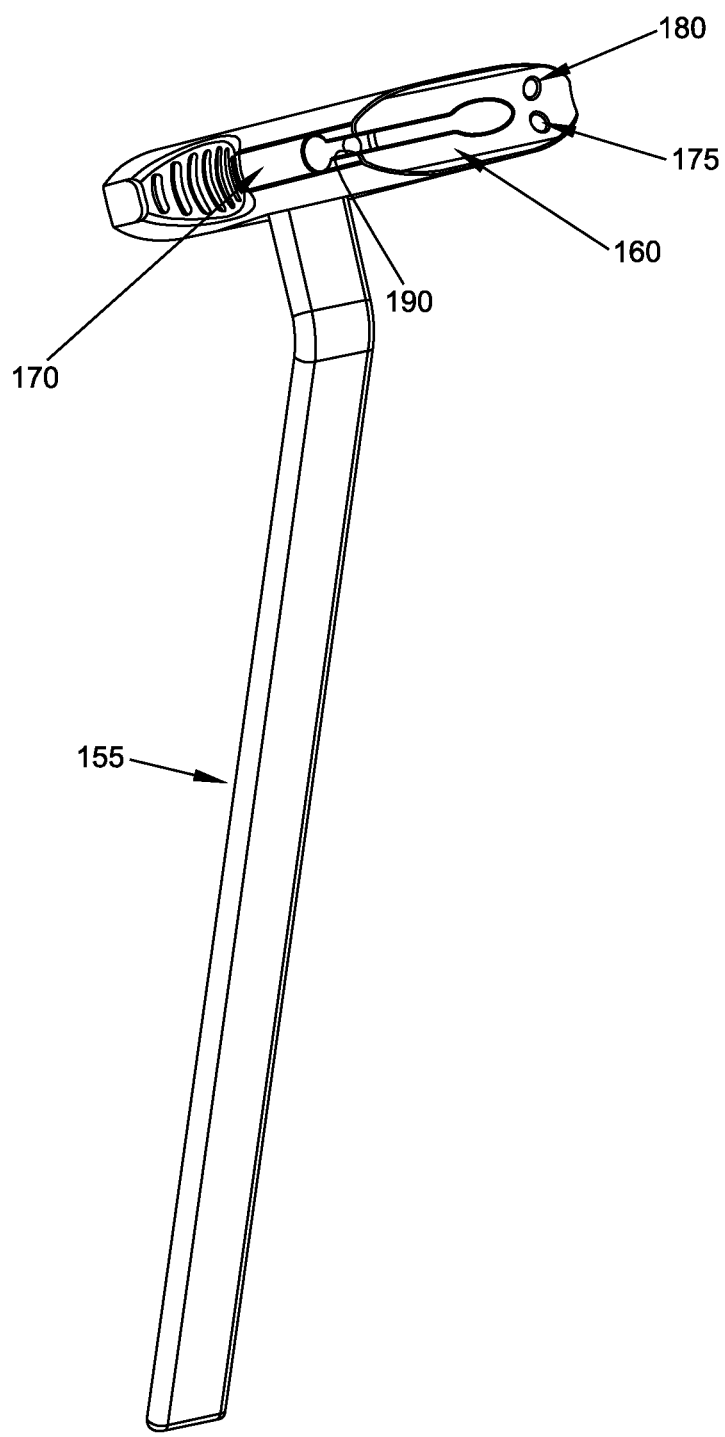

Lateral entry drill guide 125 is shown in detail in FIGS. 10-12. Lateral entry drill guide 125 generally comprises a body 150 and a handle 155 for manipulating body 150. Body 150 comprises a concave distal surface 160, a proximal surface 165 and a surface 170 extending therebetween. Three holes 175, 180 and 185 extend from proximal surface 165 to distal surface 160. A transverse hole 190 extends between surface 170 and distal surface 160. Holes 175, 180 and 190 are positioned such that holes 175 and 180 straddle, but do not intersect, hole 190. Holes 185 and 190 are positioned such that hole 190 opens on distal surface 160 of body 150 laterally spaced from where hole 185 opens on distal surface 160.

Figure 13:
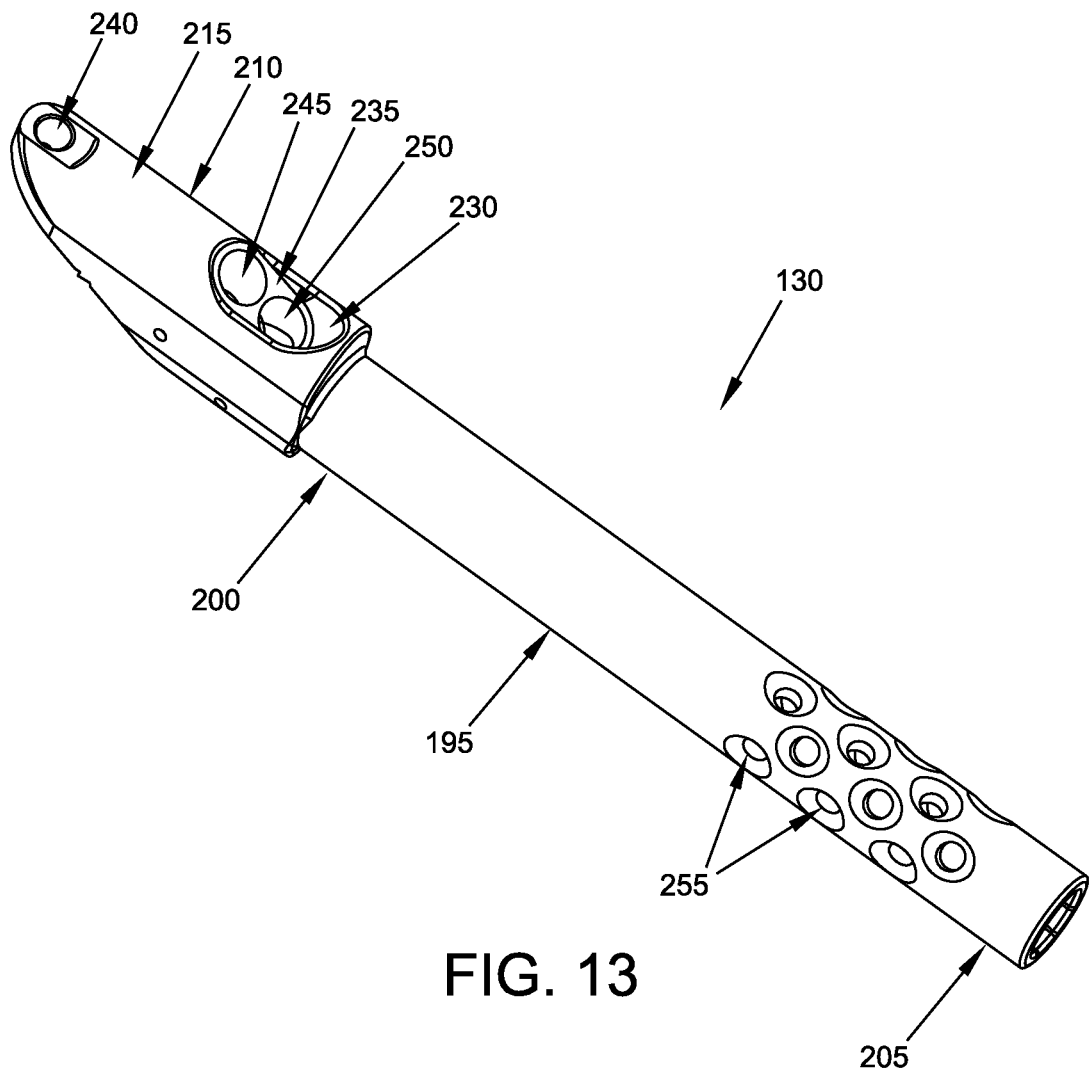
FIGS. 13-15 are schematic views showing an inserter which may be used in conjunction with the novel fracture fixation apparatus shown in FIG. 1.
Figure 14:
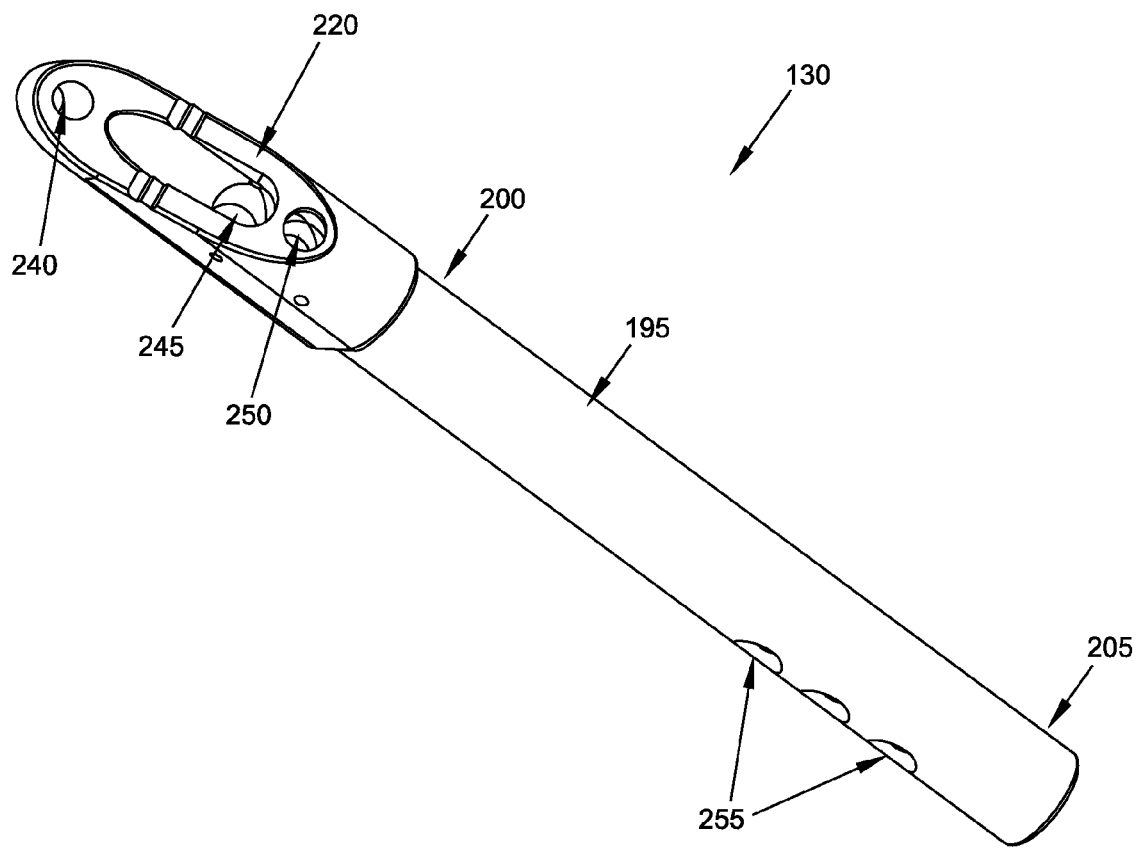
Figure 15:
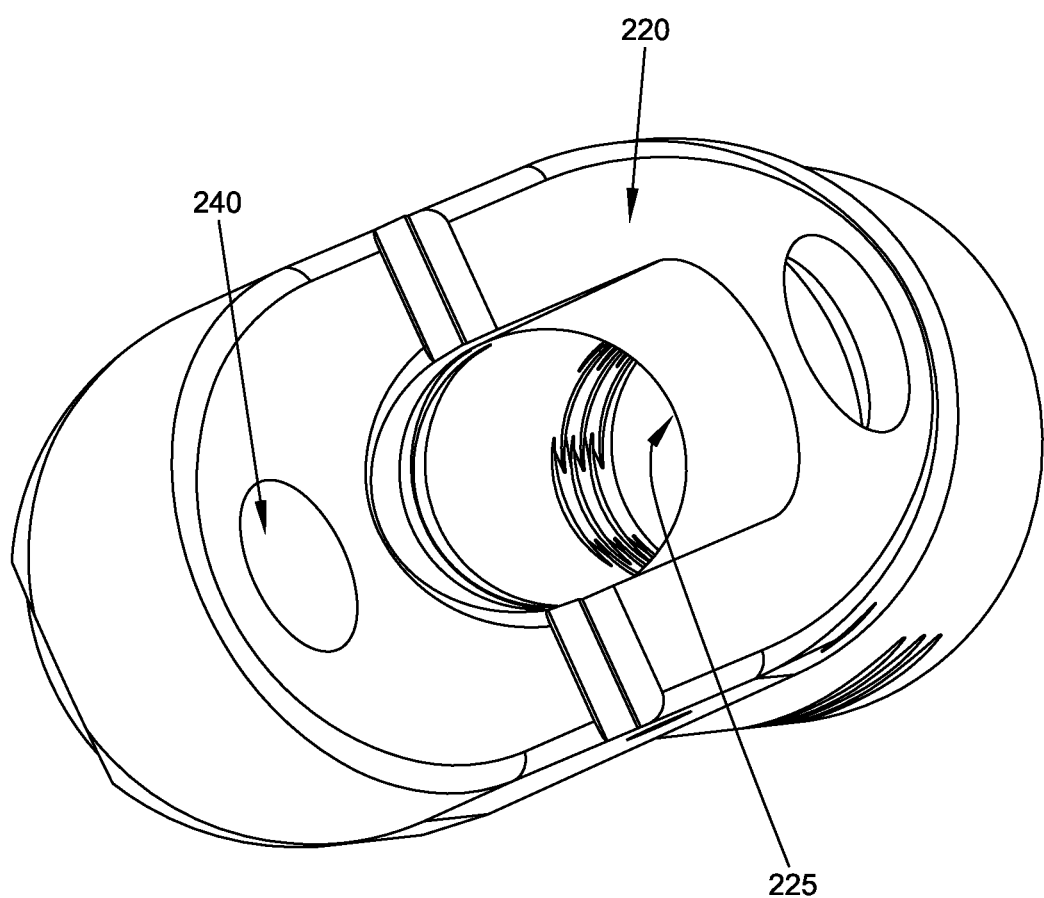

Inserter 130 is shown in detail in FIGS. 13-15. Inserter 130 generally comprises an elongated shaft 195 having a distal end 200 and a proximal end 205. A mount 210 is formed at the distal end of elongated shaft 195. In one form of the invention, mount 210 is formed integral with elongated shaft 195. Mount 210 comprises a top surface 215 and a substantially flat inclined surface 220 diametrically opposed to top surface 215. A lumen 225 opens on inclined surface 220 of mount 210 and extends along the length of elongated shaft 195. Mount 210 comprises a recess 230 in its top surface 215. Recess 230 comprises a floor 235. A hole 240 extends between top surface 215 and inclined surface 220. Two holes 245, 250 extend from floor 235 of recess 230 to inclined surface 220. A plurality of holes 255 are formed on the proximal end of elongated shaft 195. Holes 255 are formed in a pattern which corresponds to the pattern of holes 50 formed on the distal end of hollow elongated shaft 25 of anchoring tube 10, such that when anchoring tube 10 is mounted to inserter 130, holes 255 in elongated shaft 195 of inserter 130 can be used to determine the disposition of holes 50 in hollow elongated shaft 25 of anchoring tube 10, as will hereinafter be discussed in further detail.

Figure 16:
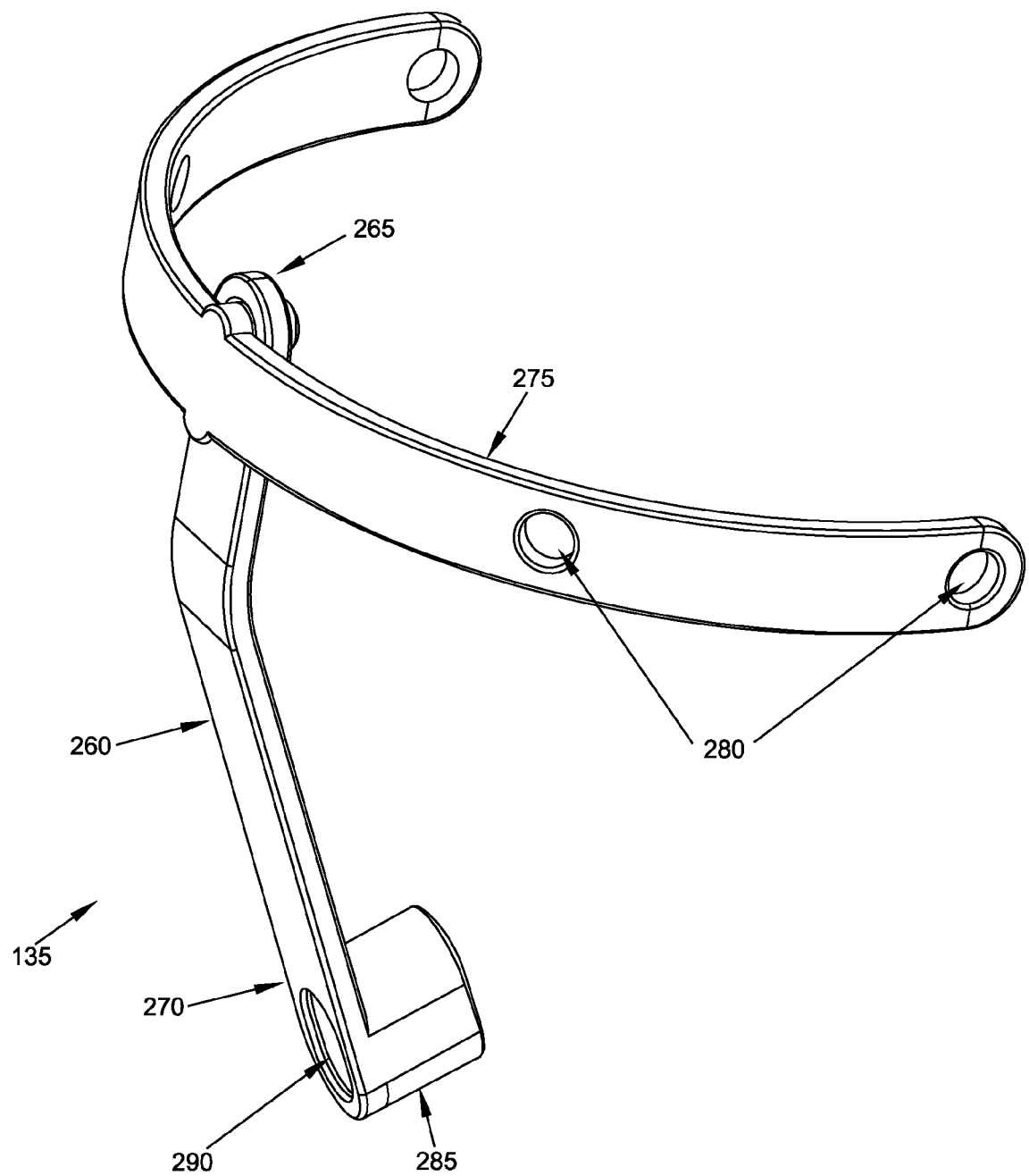
FIG. 16 is a schematic view showing a hoop guide which may be used in conjunction with the novel fracture fixation apparatus shown in FIG. 1.

Hoop guide 135 is shown in detail in FIG. 16. Hoop guide 135 generally comprises an elongated body 260 having a distal end 265 and a proximal end 270. A hoop member 275 is connected to the distal end 265 of elongated body 260. Hoop member 275 has a generally arcuate configuration sized to extend around the soft tissue surrounding proximal humerus 15, and comprises a plurality of holes 280 formed therein. A mount 285 is connected to proximal end 270 of elongated body 260. Mount 285 comprises a slot 290 formed therein.

Figure 17:
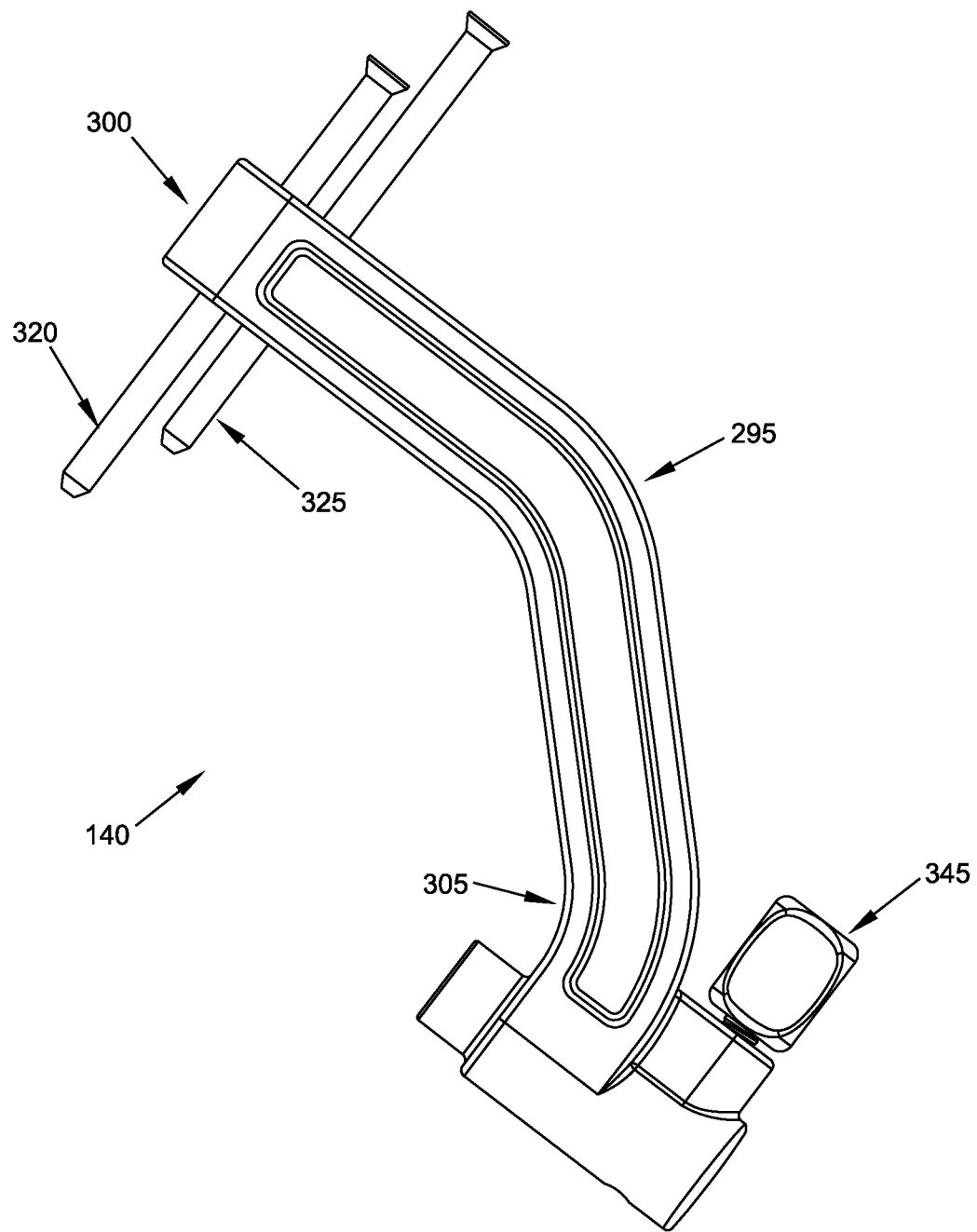
FIGS. 17-19 are schematic views showing a crossbore aimer which may be used in conjunction with the novel fracture fixation apparatus shown in FIG. 1.
Figure 18:
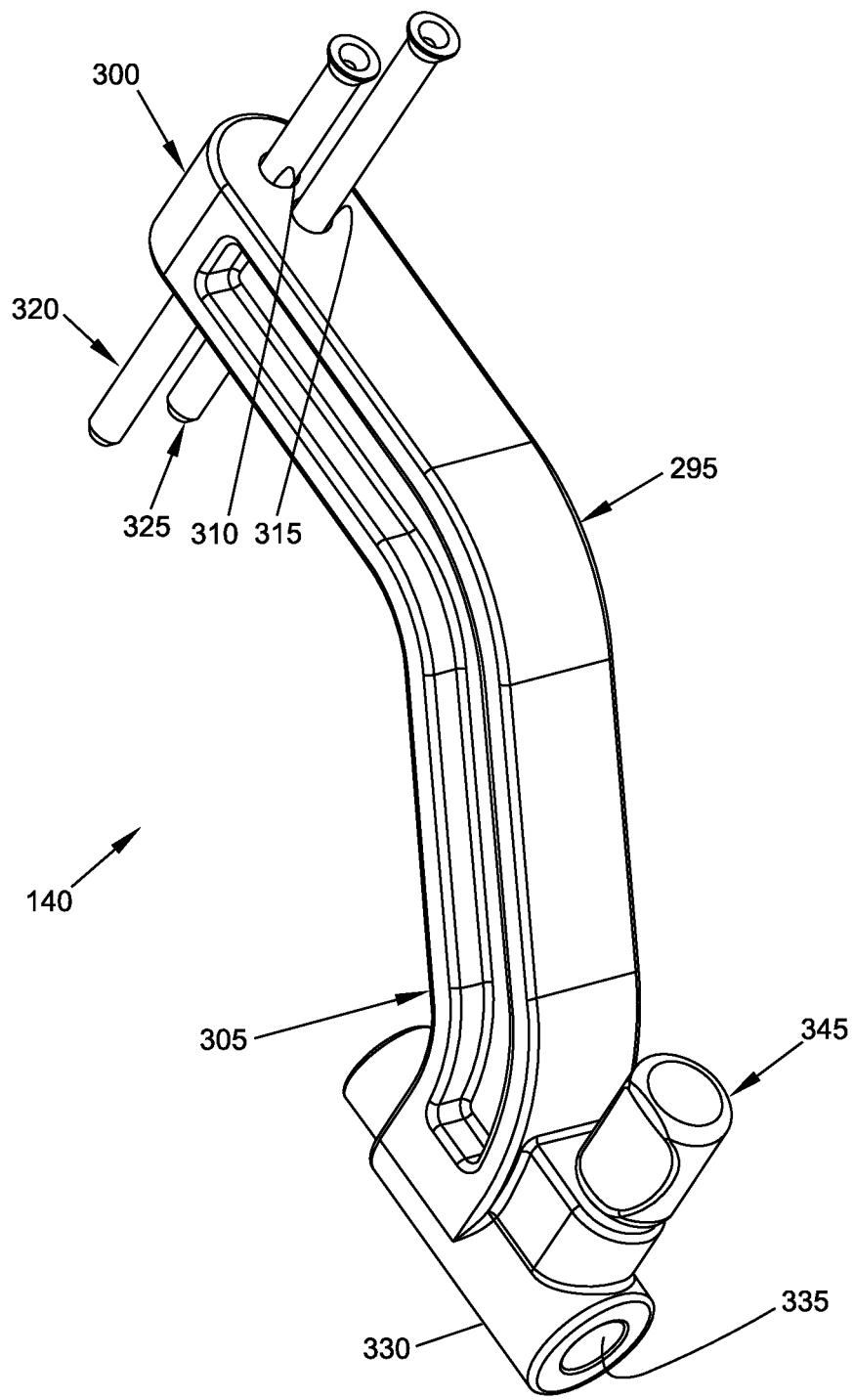
Figure 19:
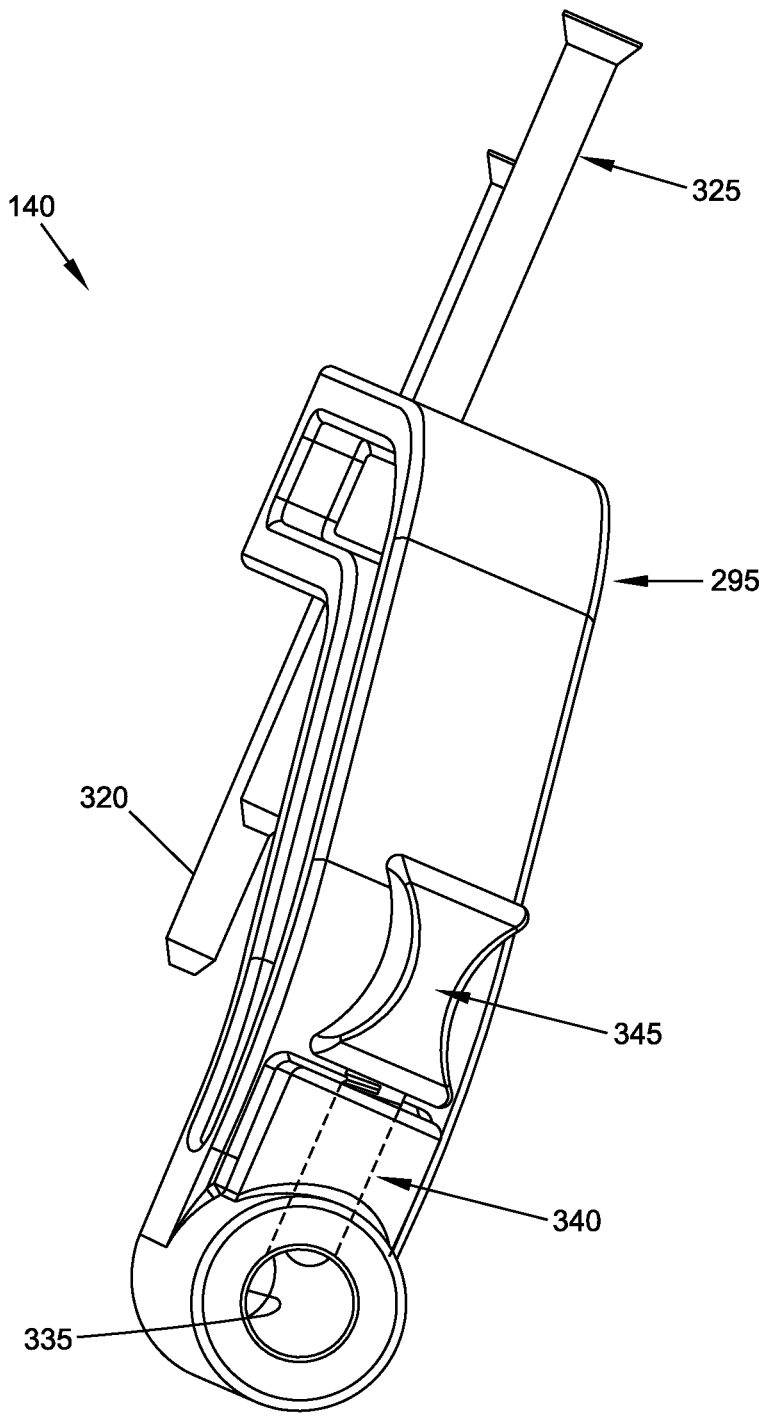

Crossbore aimer 140 is shown in detail in FIGS. 17-19. Crossbore aimer 140 comprises an outrigger 295 having a distal end 300 and a proximal end 305. Distal end 300 of outrigger 295 comprises a pair of parallel holes 310, 315 for receiving drill sleeves 320, 325 therein. Proximal end 305 of outrigger 295 comprises a hollow mount 330 having a lumen 335 extending therethrough. Hollow mount 330 includes a transverse hole 340 which communicates with lumen 335 of hollow mount 330. Transverse hole 340 receives a set screw 345, such that set screw 345 can selectively intrude across lumen 335. Transverse hole 340 in hollow mount 330 extends parallel to parallel holes 310, 315 formed in distal end 300 of outrigger 295.

Figure 20:
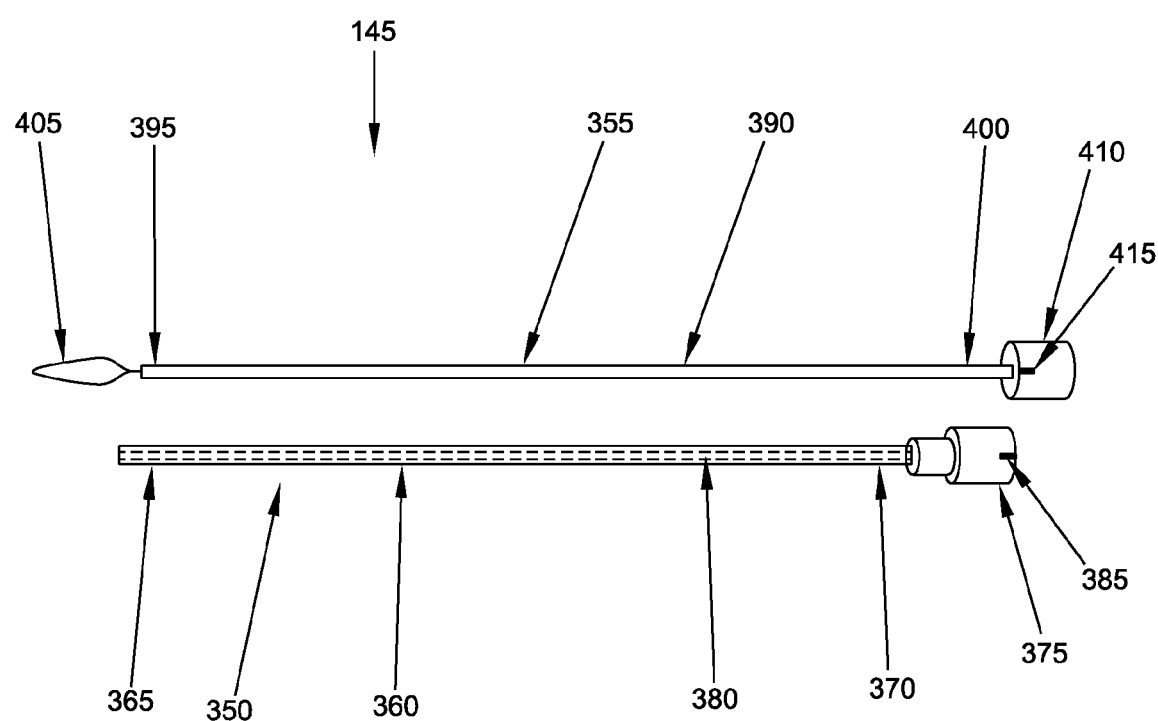
FIG. 20 is a schematic view showing a suture retriever which may be used in conjunction with the novel fracture fixation apparatus shown in FIG. 1.

Suture retriever 145 is shown in detail in FIG. 20. Suture retriever 145 comprises an outer tube assembly 350 and an inner eyelet assembly 355. Outer tube assembly 350 comprises an elongated tube 360 having a distal end 365 and a proximal end 370, and a handle 375 secured to proximal end 370 of elongated tube 360. A lumen 380 extends from distal end 365 of elongated tube 360 to handle 375. A marking 385 is disposed on handle 375. Inner eyelet assembly 355 comprises a shaft 390 having a distal end 395 and a proximal end 400, a flexible loop 405 secured to distal end 395 of shaft 390, and a handle 410 secured to proximal end 400 of shaft 390. Flexible loop 405 preferably has a substantially planar configuration. A marking 415 is disposed on handle 410. Marking 415 on handle 410 is set at a right angle to the plane of flexible loop 405, such that the orientation of flexible loop 405 may be determined by observing the orientation of marking 415 on handle 410. Outer tube assembly 350 and inner eyelet assembly 355 are sized such that shaft 390 of inner eyelet assembly 355 may be slidably received within lumen 380 of outer tube assembly 350. Furthermore, outer tube assembly 350 and inner eyelet assembly 355 are sized such that when shaft 390 of inner eyelet assembly 355 is received within lumen 380 of outer tube assembly 350, and when handle 410 of inner eyelet assembly 355 abuts handle 375 of outer tube assembly 350, flexible loop 405 will protrude out of the distal end of outer tube assembly 350.

Fracture fixation apparatus 5 may be used for treating bone fractures in general, and for treating proximal humeral fractures in particular. Such treatment generally comprises:

(a) preparing a seat in proximal humerus 15 to receive anchoring tube 10;

(b) positioning anchoring tube 10 in proximal humerus 15;

(c) preparing at least one crossbore in proximal humerus 15 to receive the suture 90 of at least one suture assembly 20; and (d) positioning the at least one suture assembly 20 so that its buckle 85 bears against the outer surface of a bone fragment and its suture 90 extends through the at least one crossbore and through anchoring tube 10, whereby to secure the bone fragment to anchoring tube 10 and, as a result, secure the bone fragment to proximal humerus 15.

(A) Preparing a Seat in Proximal Humerus 15 to Receive Anchoring Tube 10.

Figure 21:
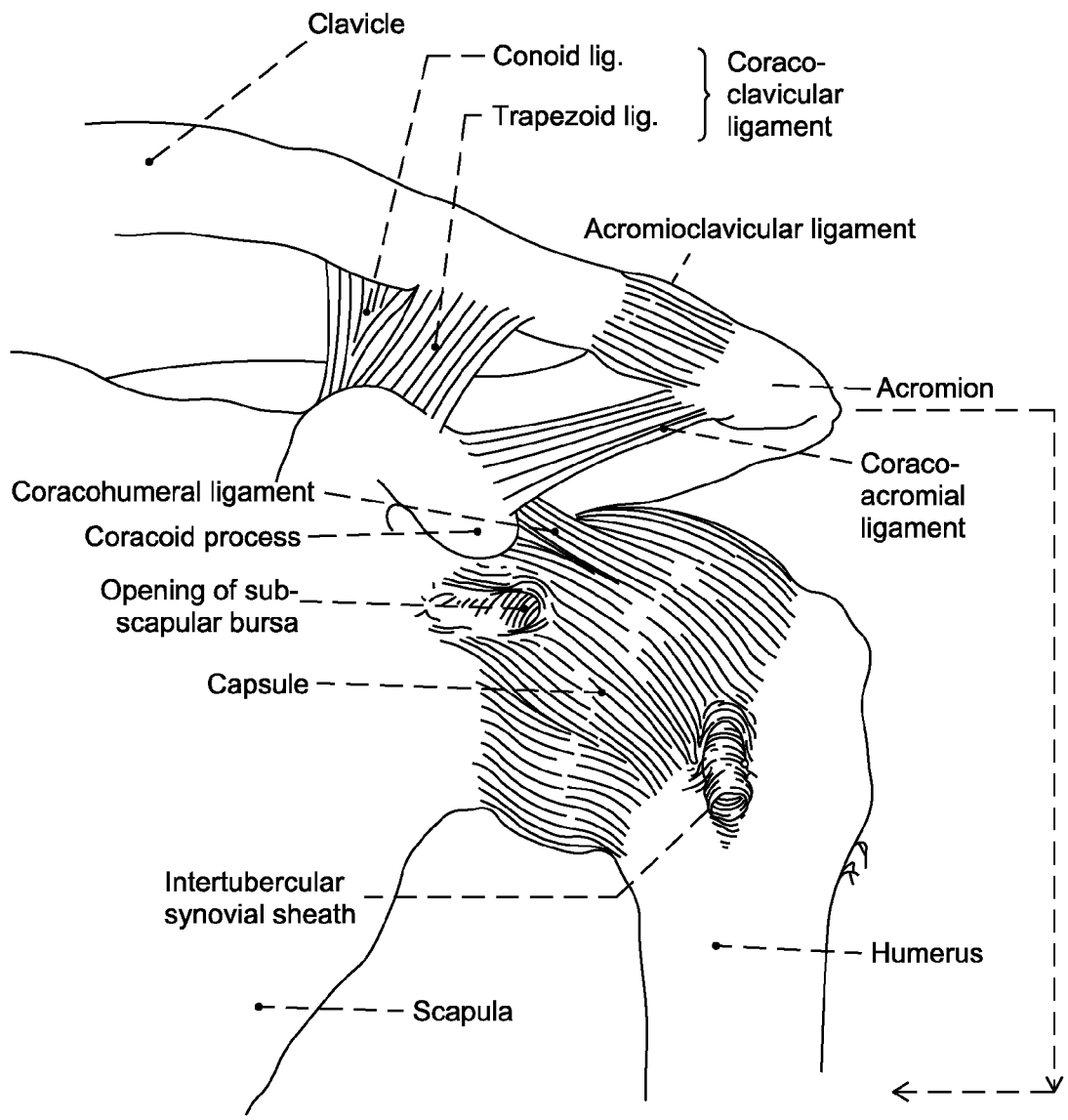
FIGS. 21-43 are schematic views showing fracture fixation in the proximal humerus using the novel fracture fixation apparatus shown in FIG. 1.
Figure 22:
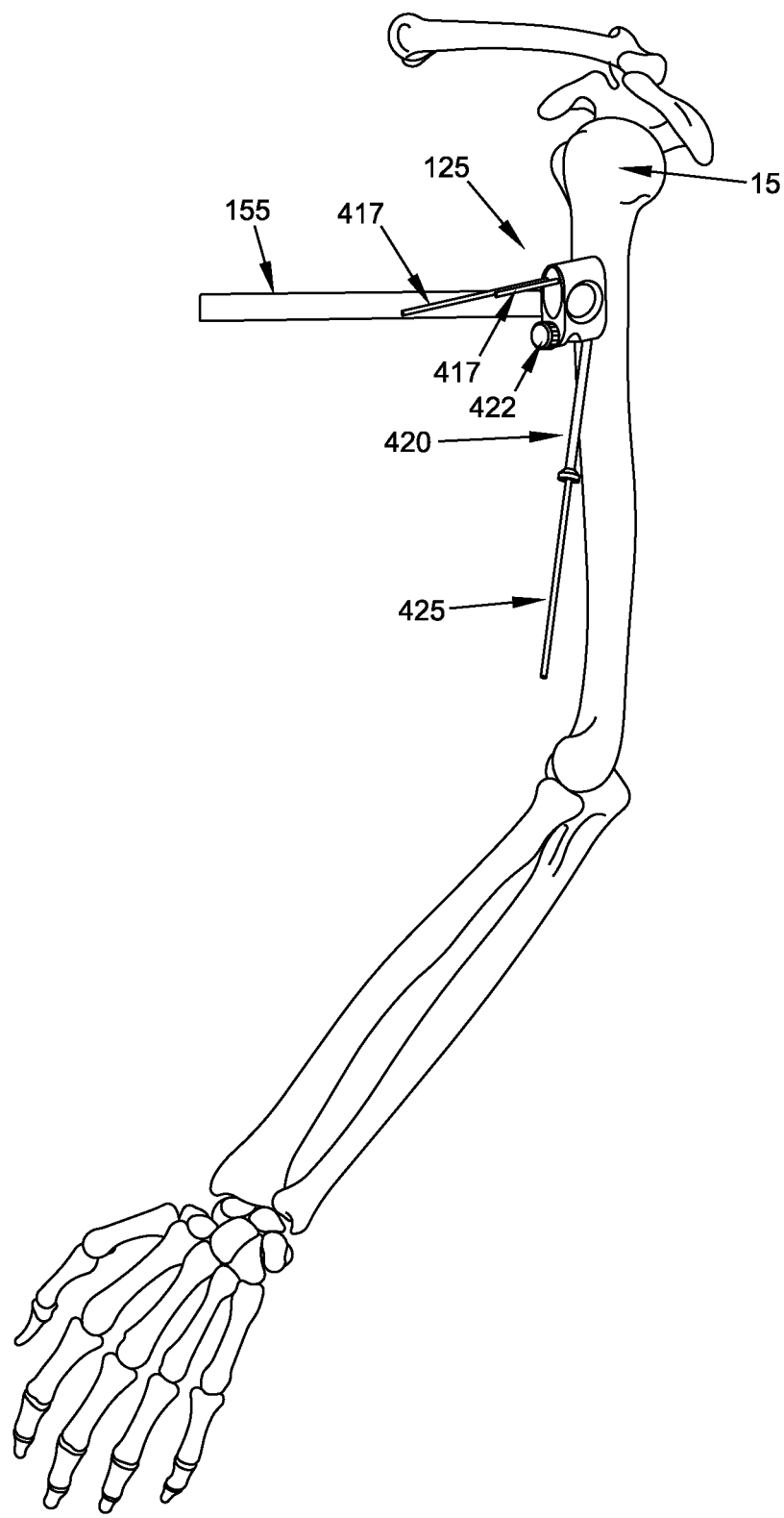
Figure 23:
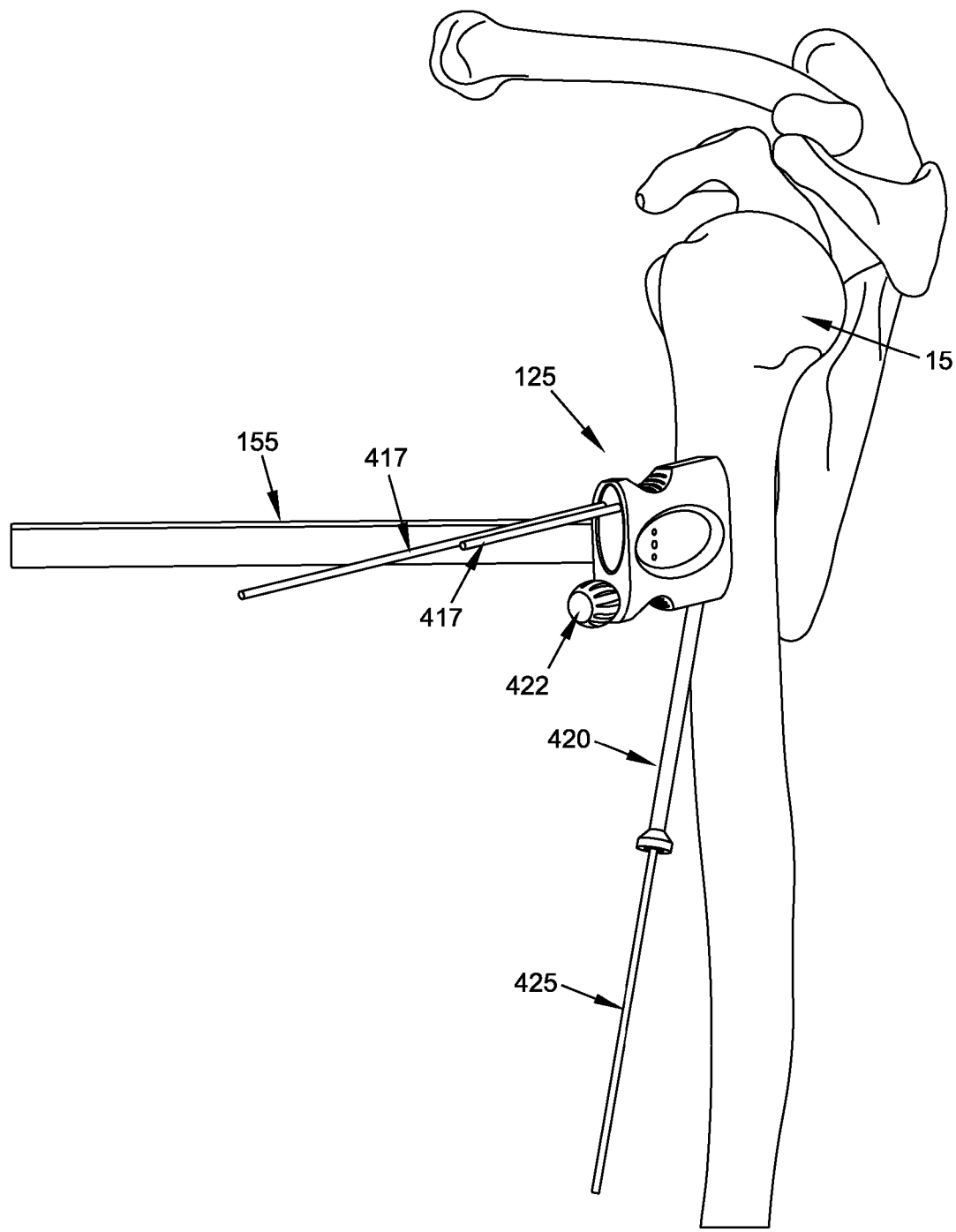
Figure 24:
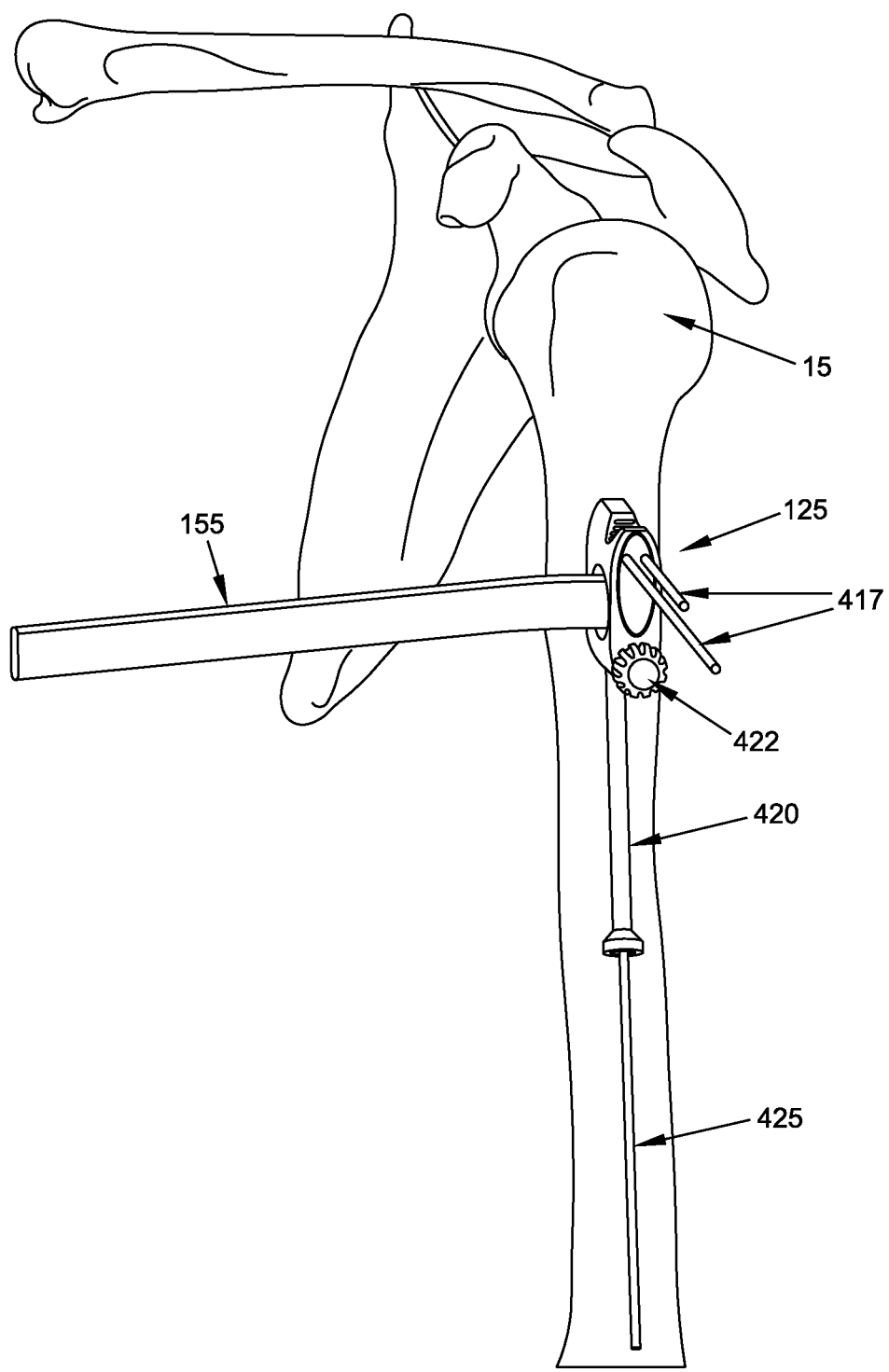
Figure 25:
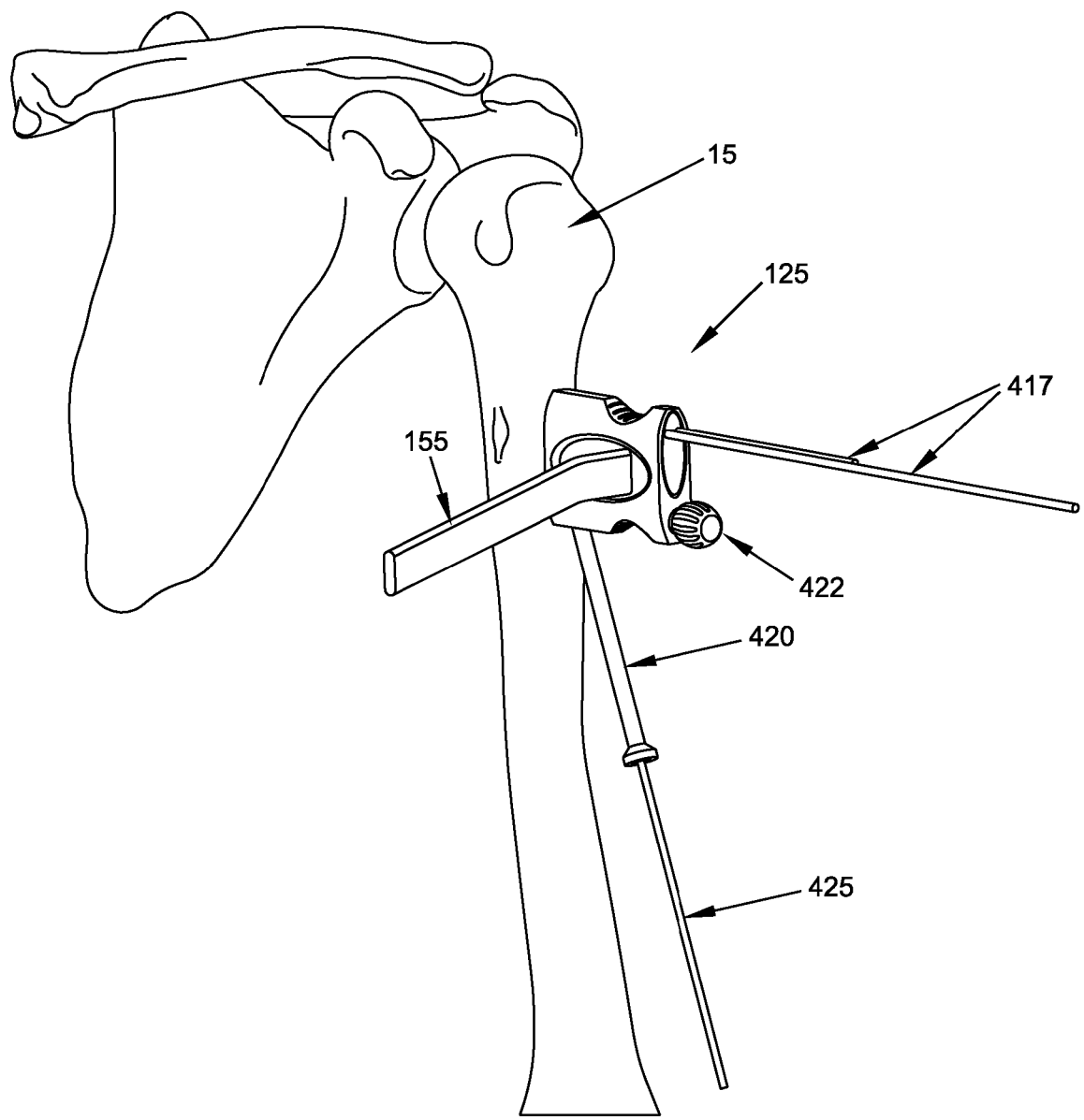

1. As seen in FIG. 21, an insertion location is identified approximately 10 cm below the lateral aspect of the acromion.

2. As seen in FIGS. 22-25, lateral entry drill guide 125 has its concave distal surface 160 positioned against proximal humerus 15 at the insertion location so that body 150 of lateral entry drill guide 125 is aligned with the humeral shaft while handle 155 is in line with the radius. This will cause hole 190 of lateral entry drill guide 125 to be directed toward the humeral head with an inferior-lateral aspect. With lateral entry drill guide 125 positioned in this manner, the lateral entry drill guide is secured to proximal humerus 15 using drilled guide pins 417 which extend through holes 175 and 180 of the lateral entry drill guide and into proximal humerus 15.

3. A drill sleeve 420 is positioned in hole 190 of lateral entry drill guide 125. A set screw 422 is inserted through hole 185 in lateral entry drill guide 125 so as to secure drill sleeve 420 in position relative to lateral entry drill guide 125. Then a guidewire 425 is drilled through drill sleeve 420, along the proximal humerus and up into the humeral head.

4. Drill sleeve 420 is removed from hole 190, lateral entry drill guide 125 is removed from proximal humerus 15, and a cannulated drill (not shown) is advanced over guidewire 425 and up into proximal humerus 15.

Figure 26:
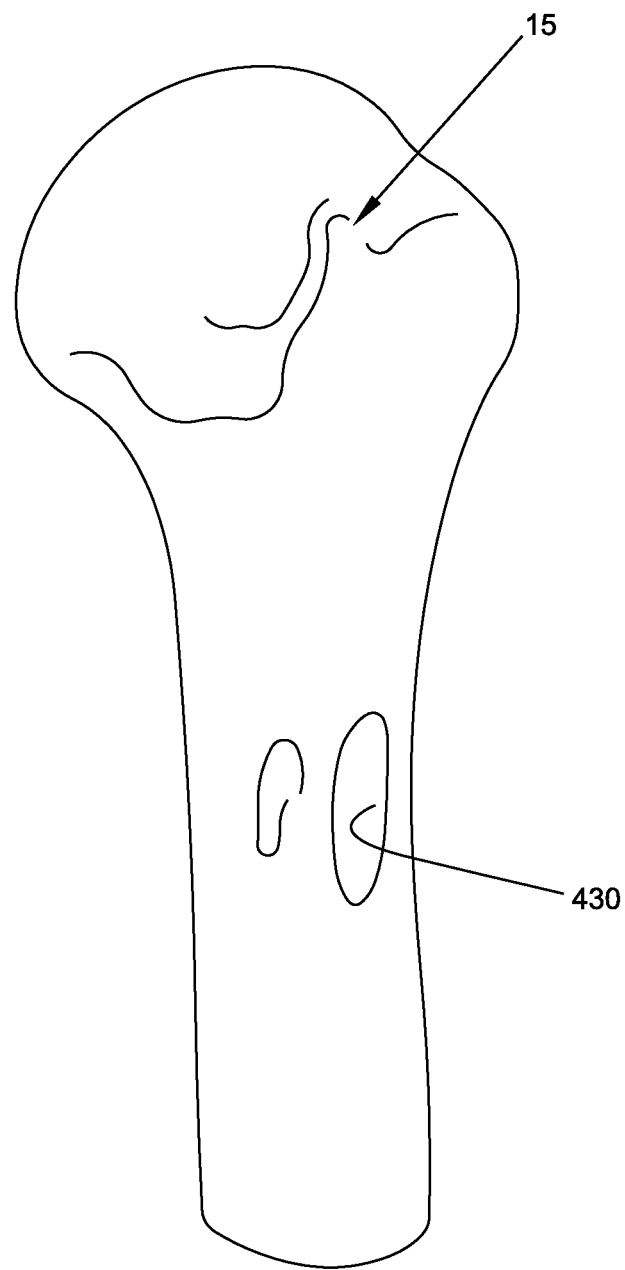

5. The cannulated drill and guidewire 425 are removed from proximal humerus 15, leaving a hole 430 formed in the proximal humerus, as seen in FIG. 26. Note that this hole is offset from the intramedullary canal of proximal humerus 15 and opens on the inferior-lateral aspect of the proximal humerus.

At this point, an appropriate seat has been prepared in proximal humerus 15 to receive anchoring tube 10.

(B) Positioning Anchoring Tube 10 in Proximal Humerus 15.

Figure 27:
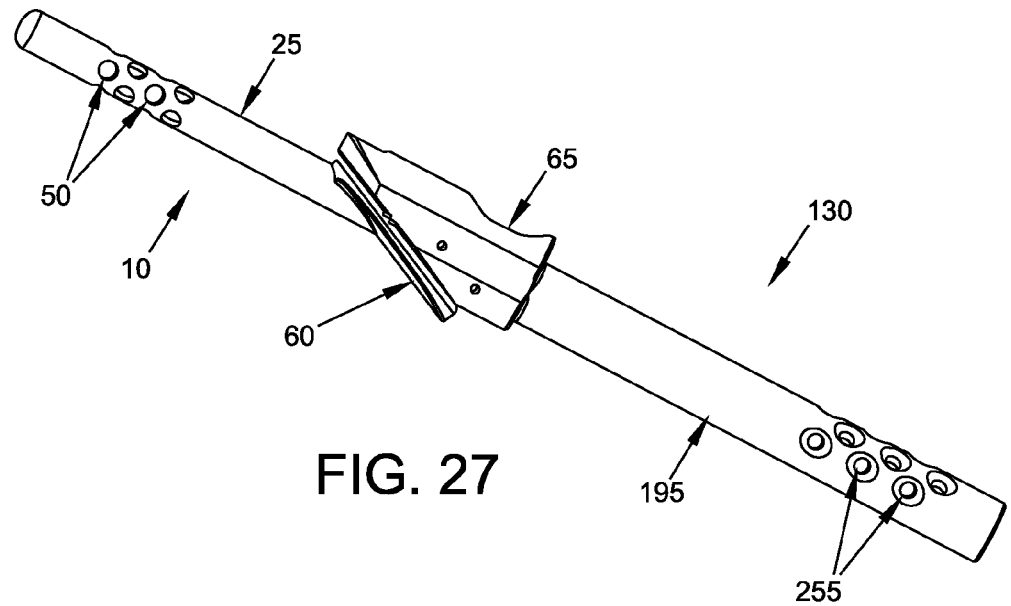
Figure 28:
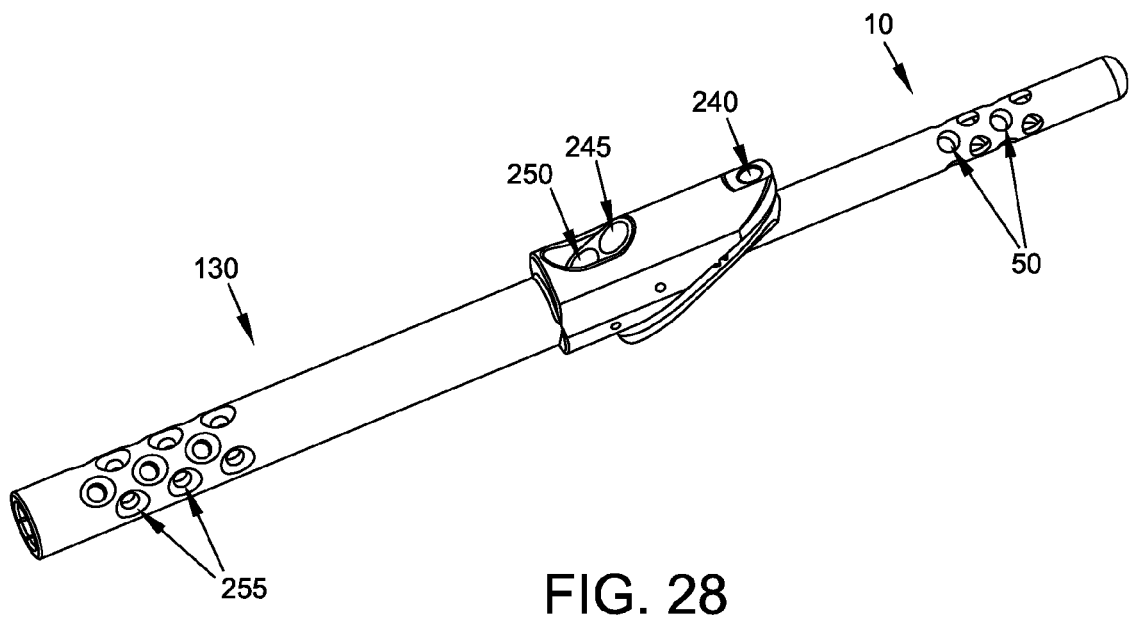
Figure 29:
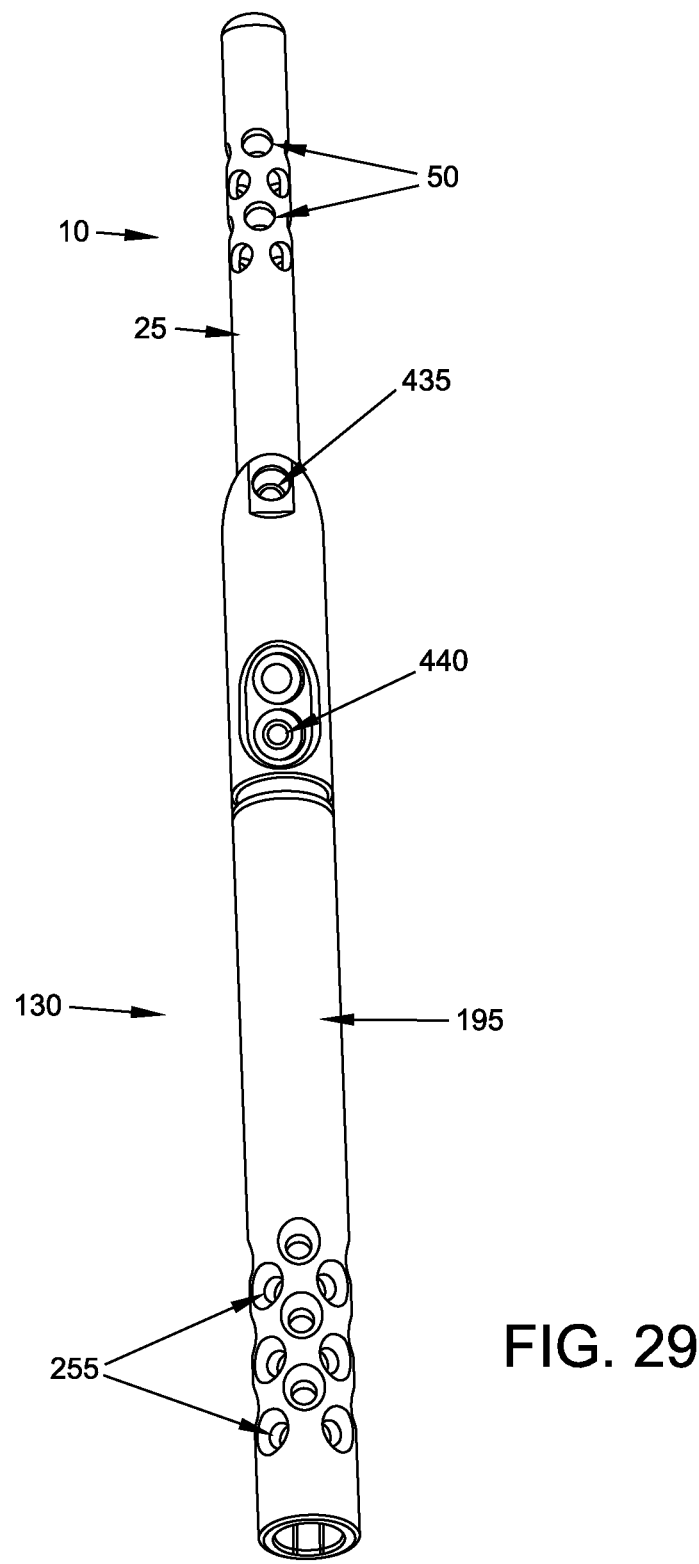

6. As seen in FIGS. 27-29, anchoring tube 10 is mounted to inserter 130, i.e., by positioning inclined surface 220 of inserter 130 against upper surface 55 of anchoring tube 10, by passing a screw 435 through hole 240 in inserter 130 and into hole 80 in anchoring tube 10, and by passing a screw 440 through hole 250 in inserter 130 and into hole 170 in anchoring tube 10. As a result, anchoring tube 10 and inserter 130 may thereafter be manipulated as a single unit. It will be appreciated that when anchoring tube 10 is so mounted to inserter 130, lumen 40 of anchoring tube 10 communicates with, and is coaxial with, lumen 225 of inserter 130. Furthermore, it will be appreciated that when anchoring tube 10 is so mounted to inserter 130, holes 255 of inserter 130 correspond to holes 50 of anchoring tube 10, such that holes 255 in inserter 130 can be used to determine the disposition of holes 50 in anchoring tube 10.

Figure 30:
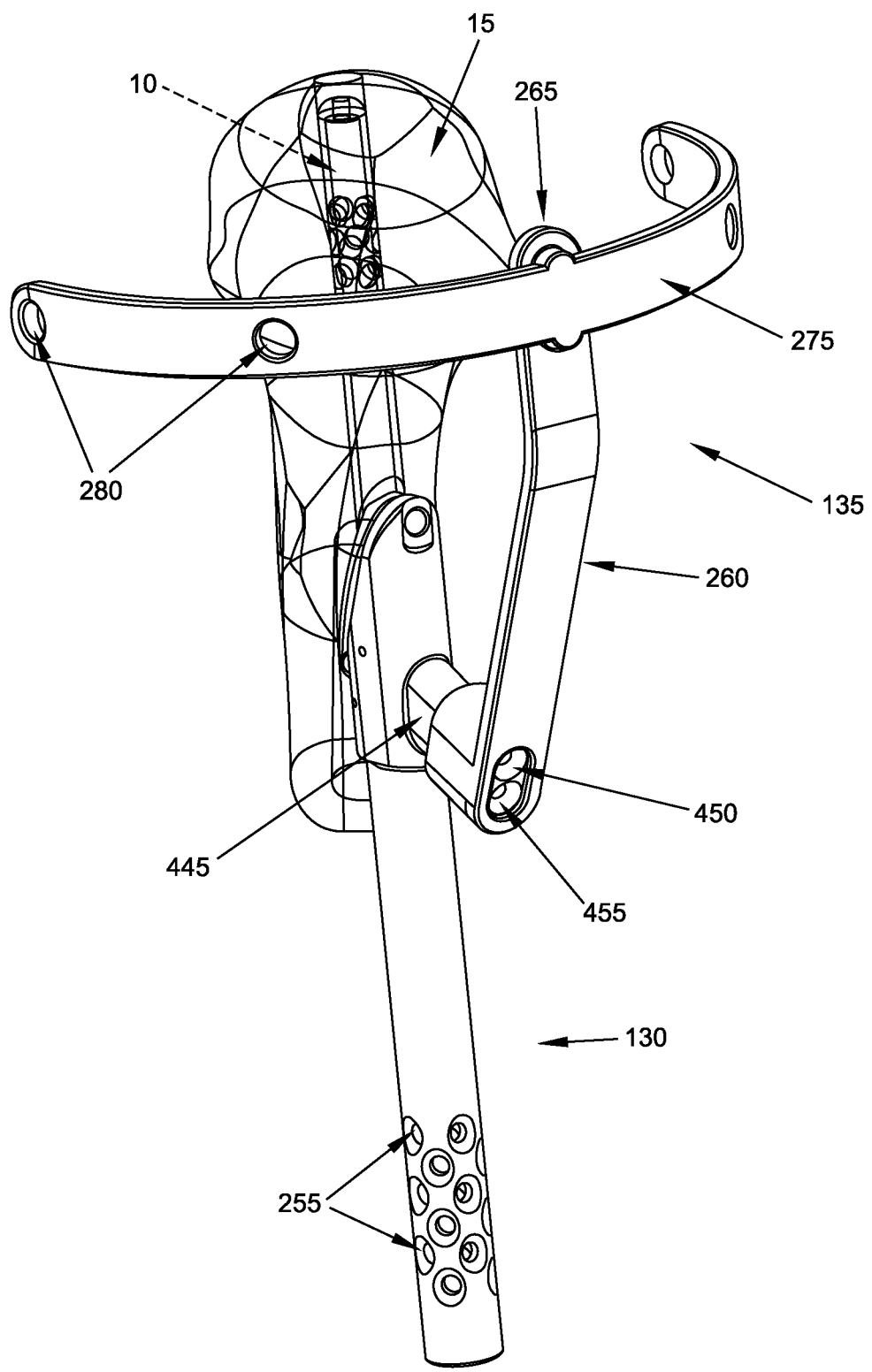

7. Inserter 130 is used to advance anchoring tube 10 into hole 430 formed in proximal humerus 15. Anchoring tube 10 is advanced into proximal humerus 15 until convex lower surface 60 of plate 45 of anchoring tube 10 seats against the outer surface of the proximal humerus. Note that the plane of plate 45 of anchoring tube 10 will be generally aligned with the outer surface of proximal humerus 15. Either before anchoring tube 10 is advanced into hole 430 in proximal humerus 15, or after anchoring tube 10 has been advanced into hole 430 of proximal humerus 15, hoop guide 135 is secured to inserter 130 so that hoop member 275 extends around the soft tissue surrounding proximal humerus 15. See FIG. 30. Significantly, when hoop guide 135 is secured to inserter 130, holes 280 in hoop guide 135 are aligned with holes 50 in anchoring tube 10. Thus, the disposition of holes 280 in hoop guide 135 can be used to determine the disposition of holes 50 in anchoring tube 10. Preferably a drill guide 445 is interposed between inserter 130 and hoop guide 135 when hoop guide 135 is mounted to inserter 130, with a hole 450 in drill guide 445 being aligned with hole 245 in inserter 130 and with a hole 455 in drill guide 445 being aligned with hole 250 in inserter 130.

8. Using holes 280 in hoop guide 135 as a visual guide, the physician uses inserter 130 to rotate anchoring tube 10 as needed so as to ensure that holes 280 in hoop guide 135, and hence holes 50 in anchoring tube 10, are aligned with a bone fragment which is to be secured to the anchoring tube (and hence to proximal humerus 15). Significantly, convex lower surface 60 of plate 45 allows for at least 30 degrees of anchoring tube rotation, while still providing a stable footing for anchoring tube 10 against proximal humerus 15, thereby allowing the physician to properly align one or more of the holes 50 in anchoring tube 10 with a bone fragment which is to be secured to the anchoring tube (and hence to proximal humerus 15).

Figure 31:
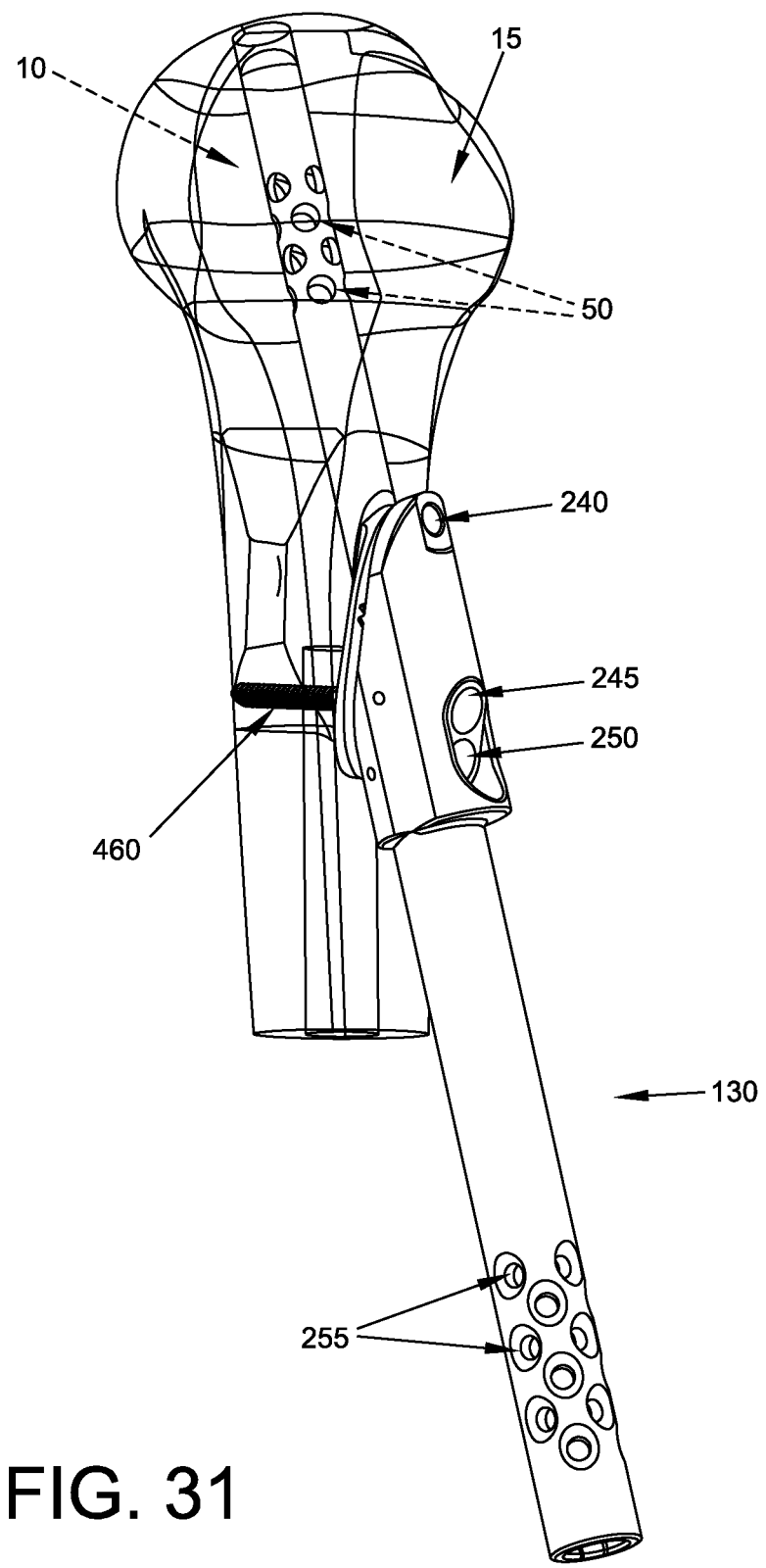

9. After optimal positioning of anchoring tube 10 has been determined, hole 450 in drill guide 445 is used to form a hole in proximal humerus 15, and then a screw 460 is used to secure anchoring tube 10 to proximal humerus 15. See FIG. 31. Note that by forming hole 245 in inserter 130 with a larger diameter than hole 75 in anchoring tube 10, screw 460 is able to pass through inserter 130 without directly coupling inserter 130 to proximal humerus 15. Then hoop guide 135 and drill guide 445 may be removed.

At this point, anchoring tube 10 has been appropriately positioned in proximal humerus 15. Note that anchoring tube 10 is set in proximal humerus 15 in a position which is not aligned with the intramedullary canal of the proximal humerus. It should be appreciated that by positioning anchoring tube 10 in proximal humerus 15 in the foregoing manner, deployment of the anchoring tube is achieved via a minimally invasive procedure, thereby minimizing trauma to the soft tissue surrounding the proximal humerus. Moreover, by preserving the outer layer of cortical bone, bone loss is minimized. In addition, blood loss during the surgical procedure is also minimized. Finally, by positioning anchoring tube 10 in hole 430 formed in proximal humerus 15, rather than in the intramedullary canal of the proximal humerus, the intramedullary canal is preserved, thereby maintaining bone structure and function.

(C) Preparing at Least One Crossbore in Proximal Humerus 15 to Receive the Suture 90 of at Least One Suture Assembly 20.

Figure 32:
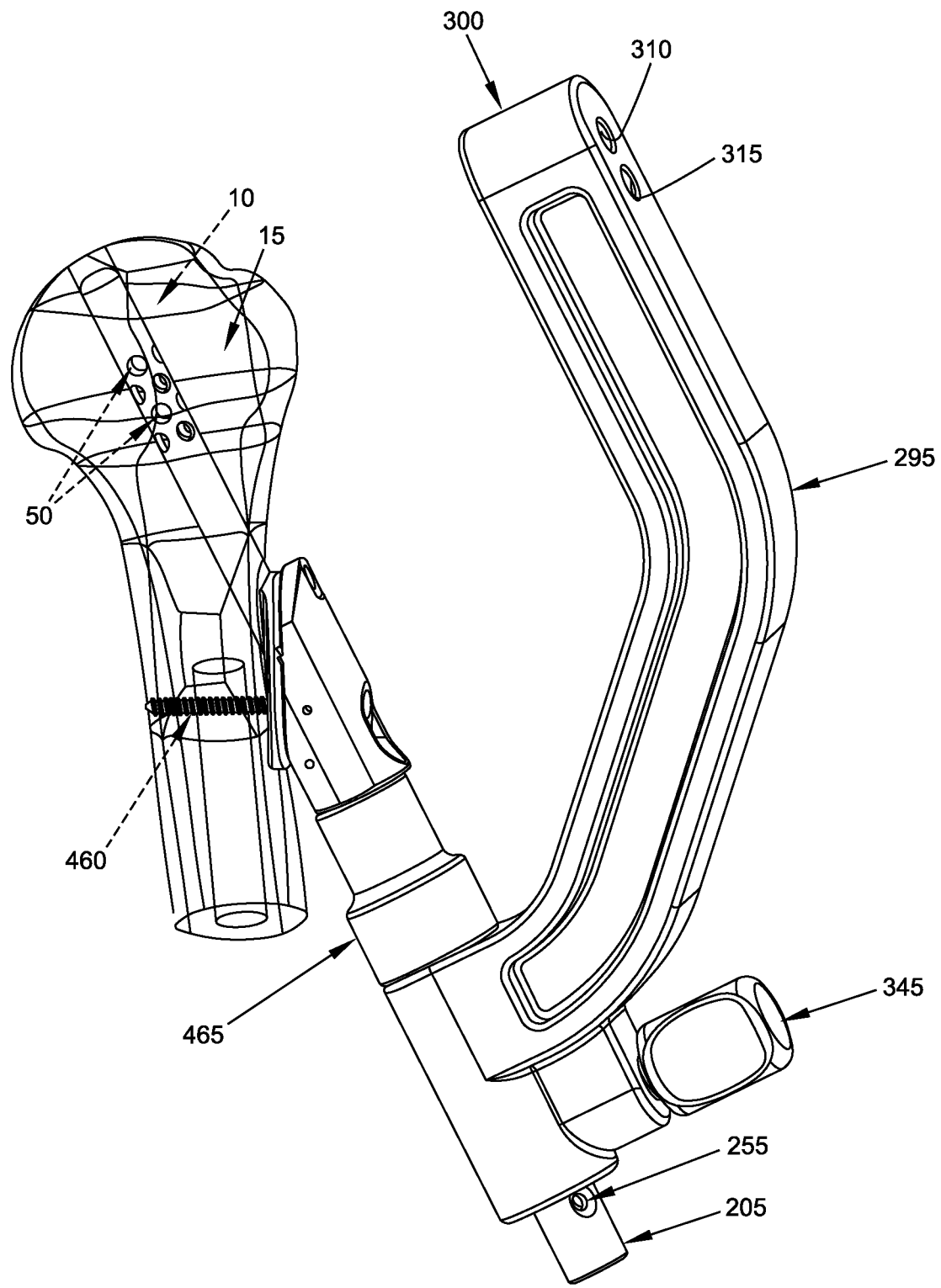

10. As seen in FIG. 32, crossbore aimer 140 is mounted on inserter 130, i.e., by fitting hollow mount 330 of crossbore aimer 140 over elongated shaft 195 of inserter 130. A spacer 465 may be interposed between mount 210 of inserter 130 and hollow mount 330 so as to properly position crossbore aimer 140 on inserter 130. Then crossbore aimer 140 is rotated about inserter 130 so that transverse hole 340 formed in hollow mount 330 of crossbore aimer 140 is aligned with one of the holes 255 in inserter 130 (and, hence, parallel holes 310, 315 formed in distal end 300 of outrigger 295 are aligned with one or more of the holes 50 in anchoring tube 10). Note that this alignment of holes 310, 315 in crossbore aimer 140 is reliably achieved even though holes 50 in anchoring tube 10 are hidden from sight within the interior of proximal humerus 15. Then set screw 345 is advanced along transverse hole 340 in crossbore aimer 140 and into one of the holes 255 formed in inserter 130, whereby to ensure that holes 310, 315 in crossbore aimer 140 are locked in alignment with one or more of the holes 50 in anchoring tube 10.

Figure 33:
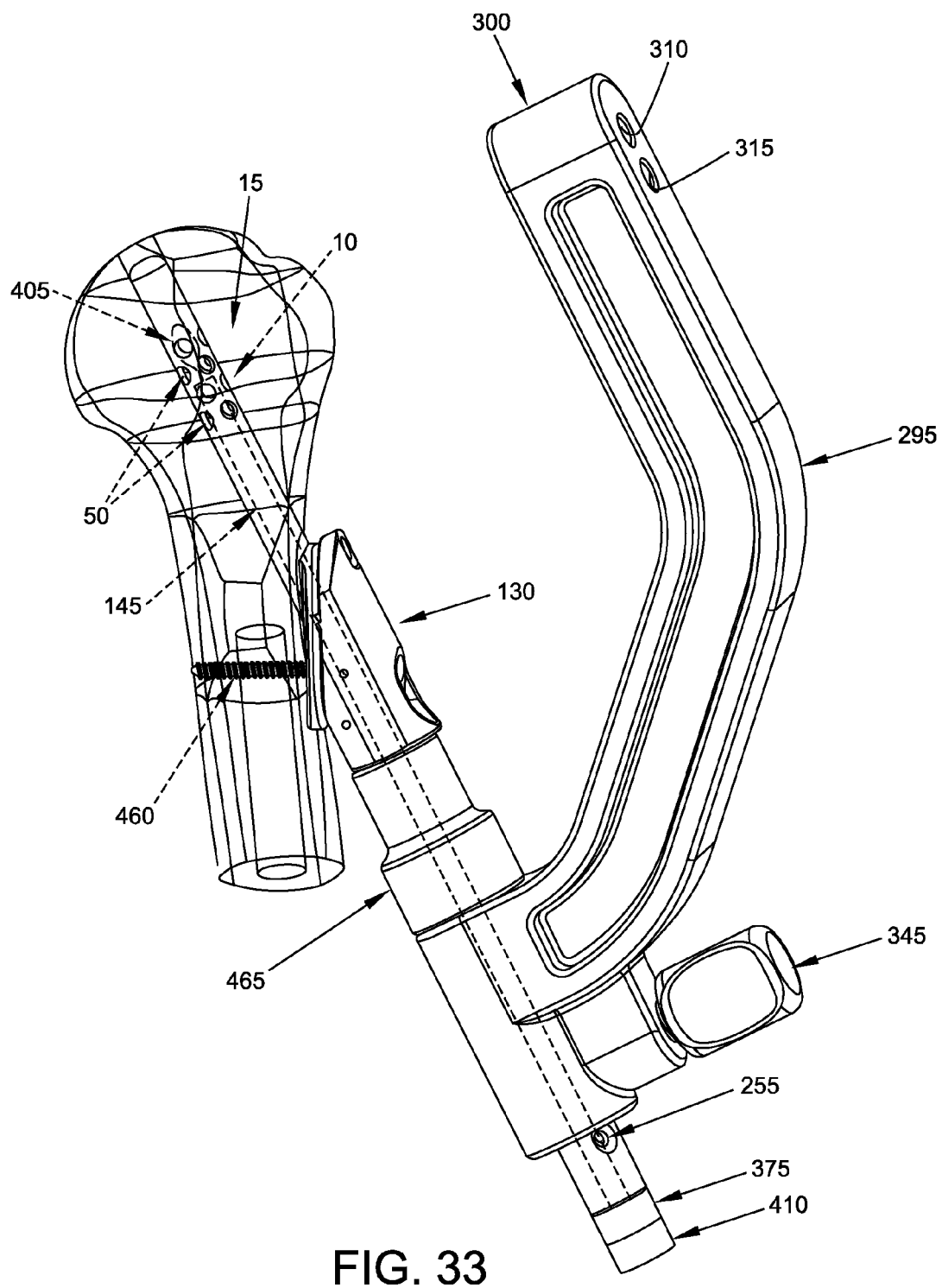
Figure 34:
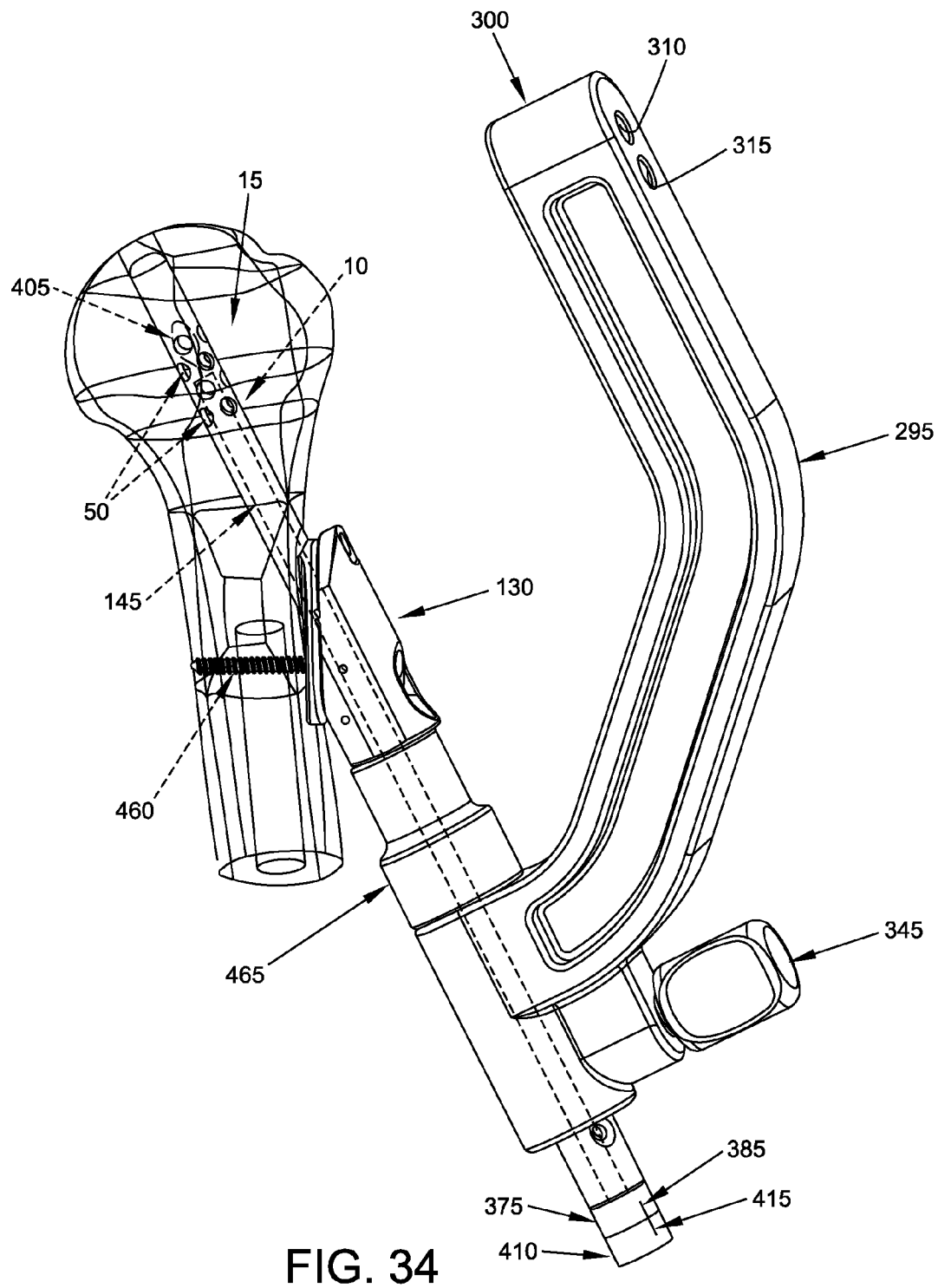

11. As seen in FIGS. 33 and 34, suture retriever 135 is advanced up lumen 225 of inserter 130 and lumen 40 of anchoring tube 10 so that flexible loop 405 extends across the axes of holes 310, 315 of crossbore aimer 140 (and hence across the axis/axes of one or more of the holes 50 in anchoring tube 10). Using markings 385, 415 of suture retriever 145, flexible loop 405 is turned as necessary so that the plane of flexible loop 405 is set at a right angle to holes 310, 315 of crossbore aimer 140.

Figure 35:
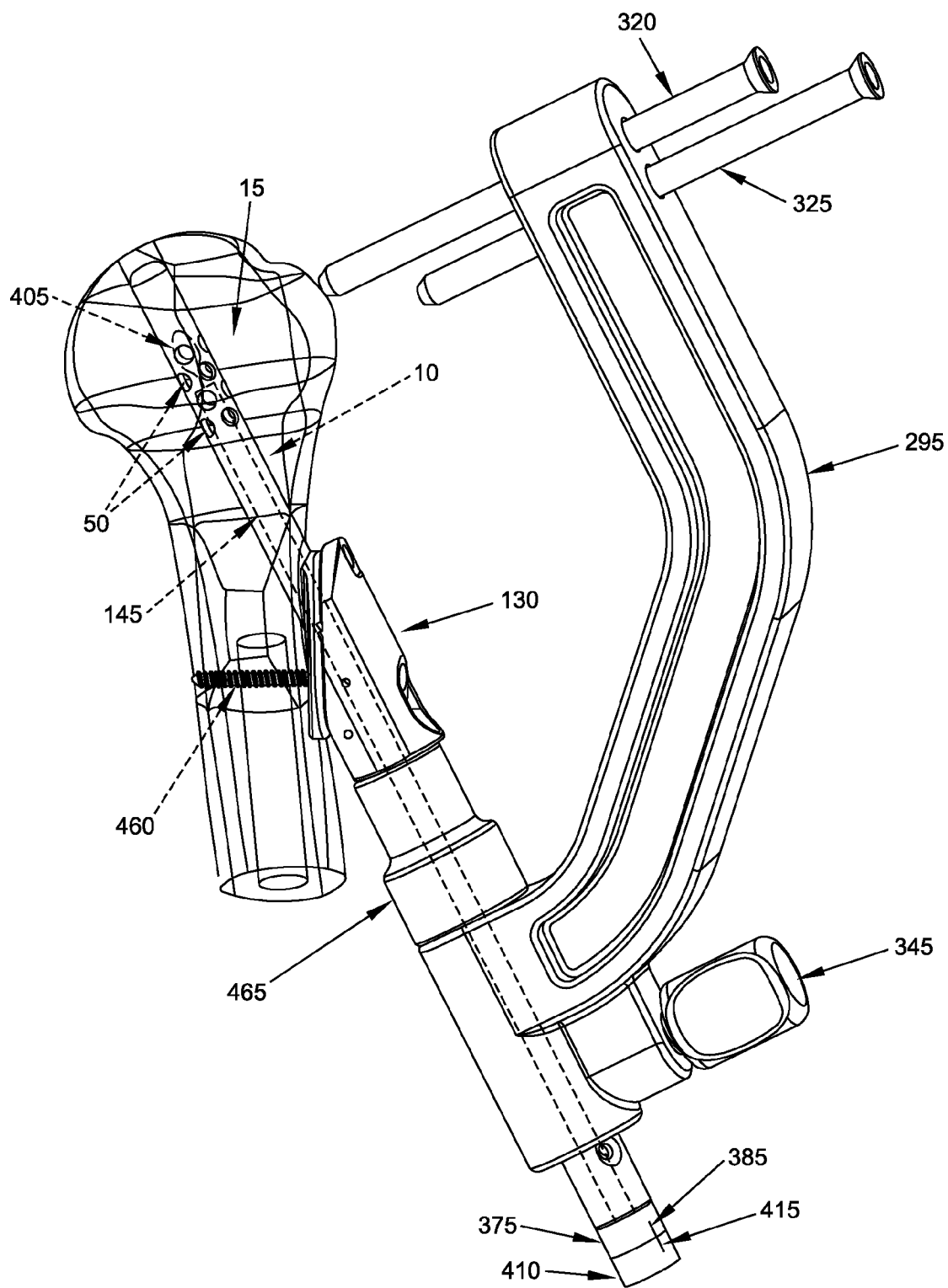

12. As seen in FIG. 35, one or both of the drill sleeves 320, 325 are positioned in holes 310, 315 of crossbore aimer 140, respectively.

Figure 36:
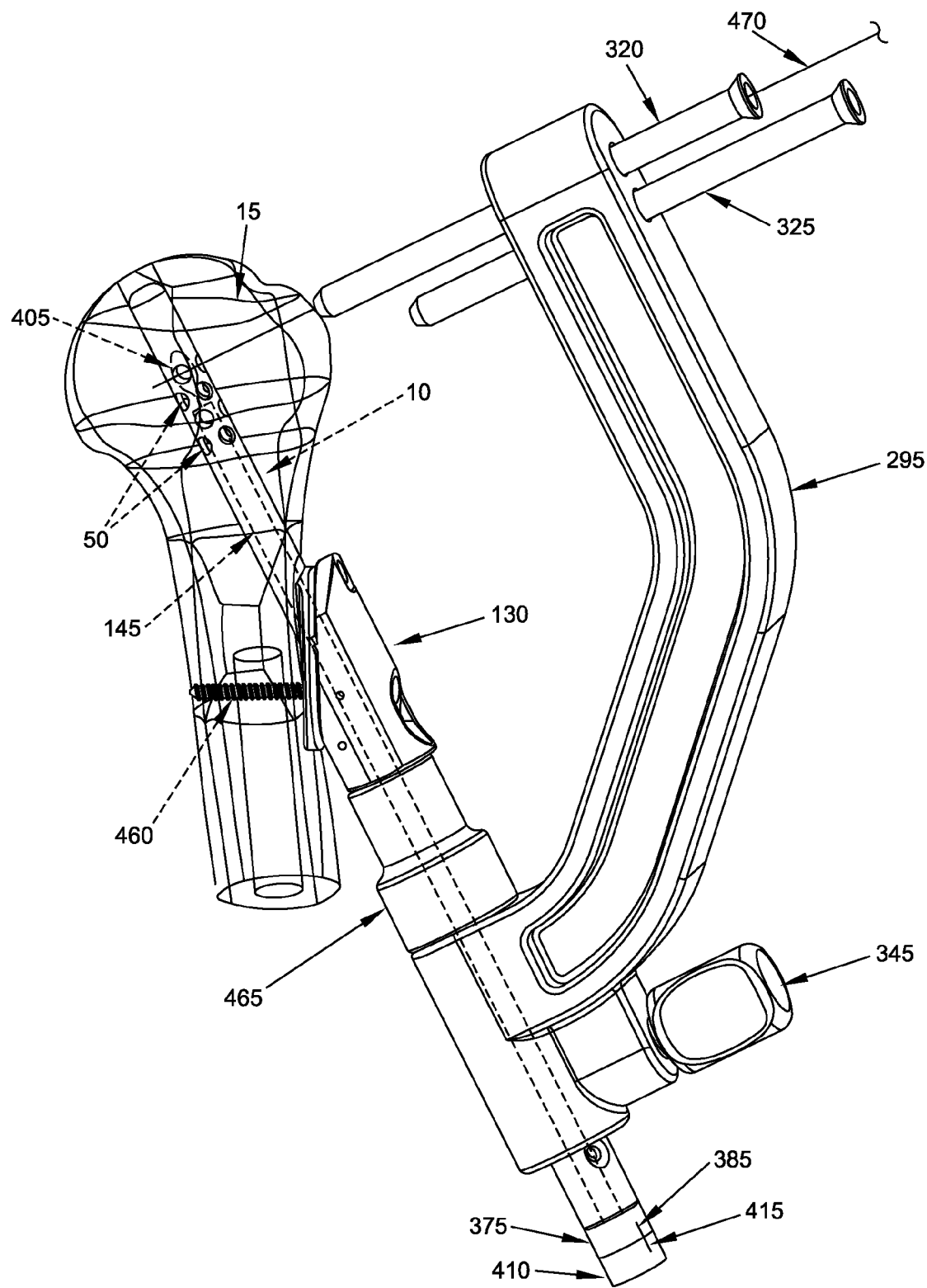

13. A guidewire 470 is drilled through one of the drill sleeves 320, 325 so as to pass through two diametrically-opposing holes 50 of anchoring tube 10, passing through flexible loop 405 of suture retriever 145 in the process (FIG. 36).

Figure 37:
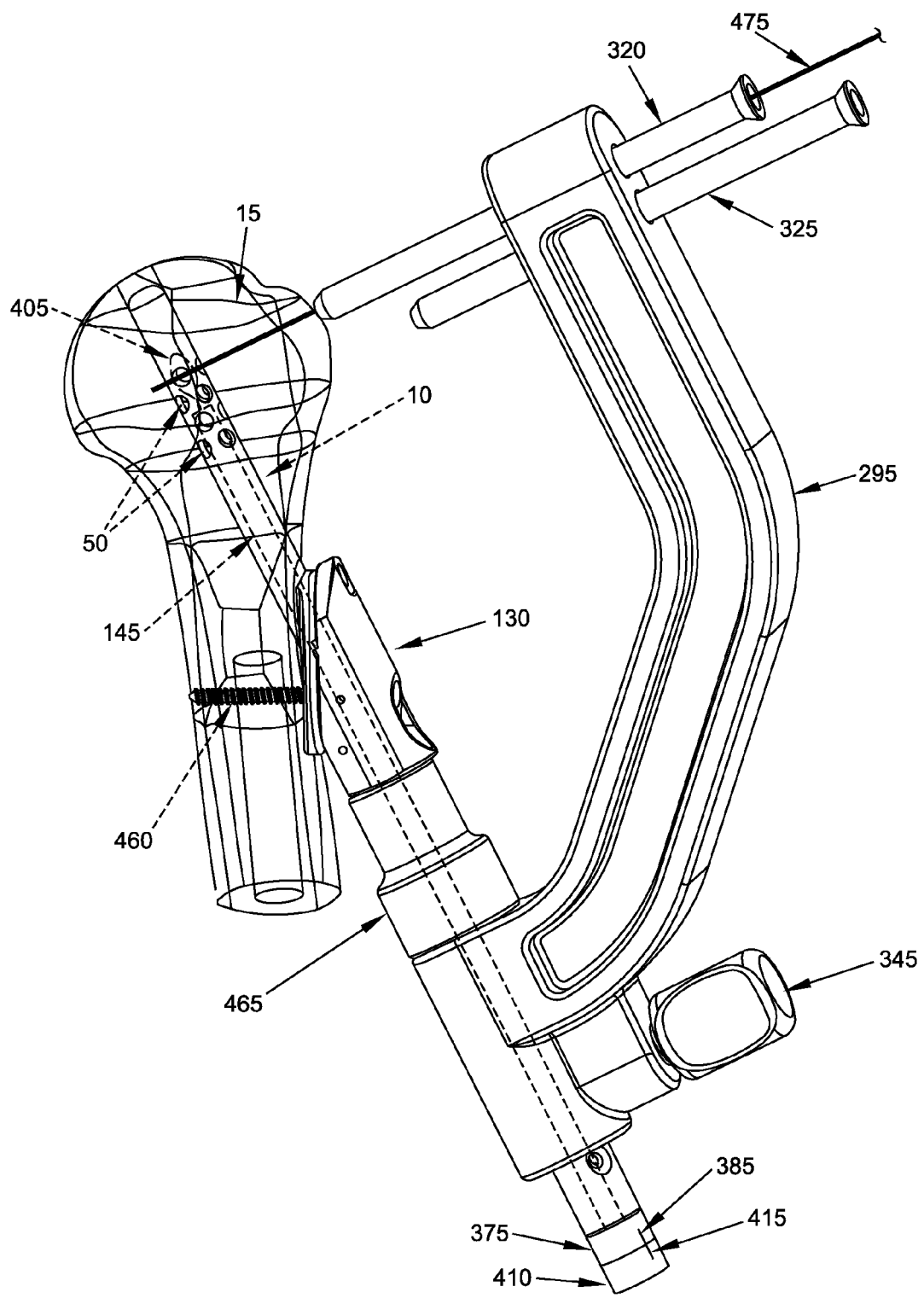

14. A cannulated drill 475 is passed along guidewire 470 so that the cannulated drill passes through two diametrically-opposing holes 50 of anchoring tube 10, and through flexible loop 405 of suture retriever 145 (FIG. 37).

At this point, at least one crossbore has been formed in proximal humerus 15 to receive the suture 90 of at least one suture assembly 20.

(D) Positioning the at Least One Suture Assembly 20 So that its Buckle 85 Bears Against the Outer Surface of a Bone Fragment and its Suture 90 Extends Through the at Least One Crossbore and Through Anchoring Tube 10, Whereby to Secure the Bone Fragment to Anchoring Tube 10 and, as a Result, Secure the Bone Fragment to Proximal Humerus 15.

Figure 38:
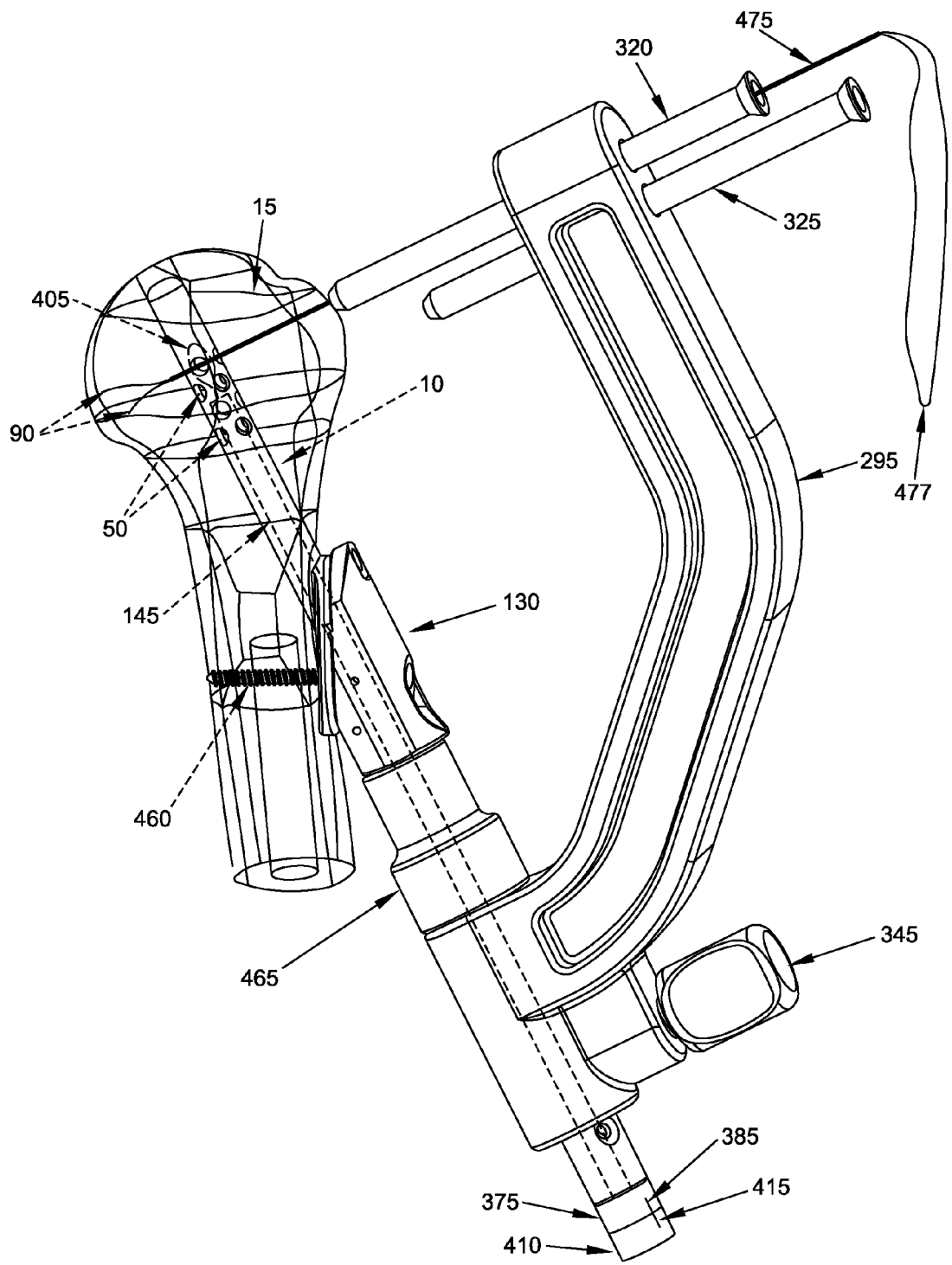

15. Guidewire 470 is removed from cannulated drill 475, and the two free ends of suture 90 of a suture assembly 20 are fed through the lumen of cannulated drill 475, so that the two free ends of suture 90 pass through two diametrically-opposing holes 50 of anchoring tube 10, and through flexible loop 405 of suture retriever 145 (FIG. 38). At this point, the closed loop 477 of suture 90 will reside outside cannulated drill 475.

Figure 39:
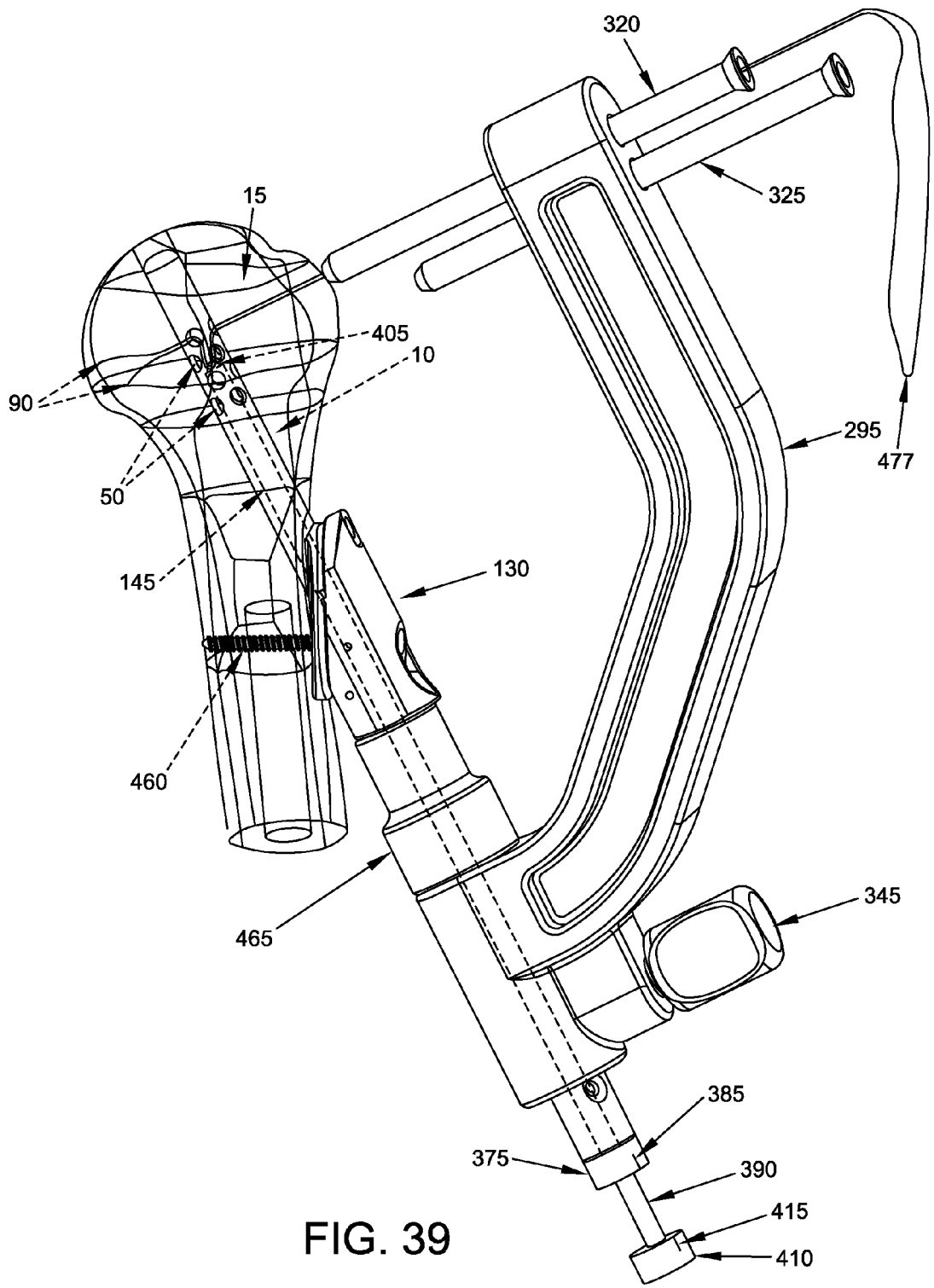

16. Cannulated drill 475 is removed from anchoring tube 10 as inner eyelet assembly 355 is pulled proximally, thereby reducing the portion of flexible loop 405 extending out of elongated tube 360, whereby to capture the two free ends of suture 90 of suture assembly 20 to the distal end of suture retriever 145 (FIG. 39).

Figure 40:
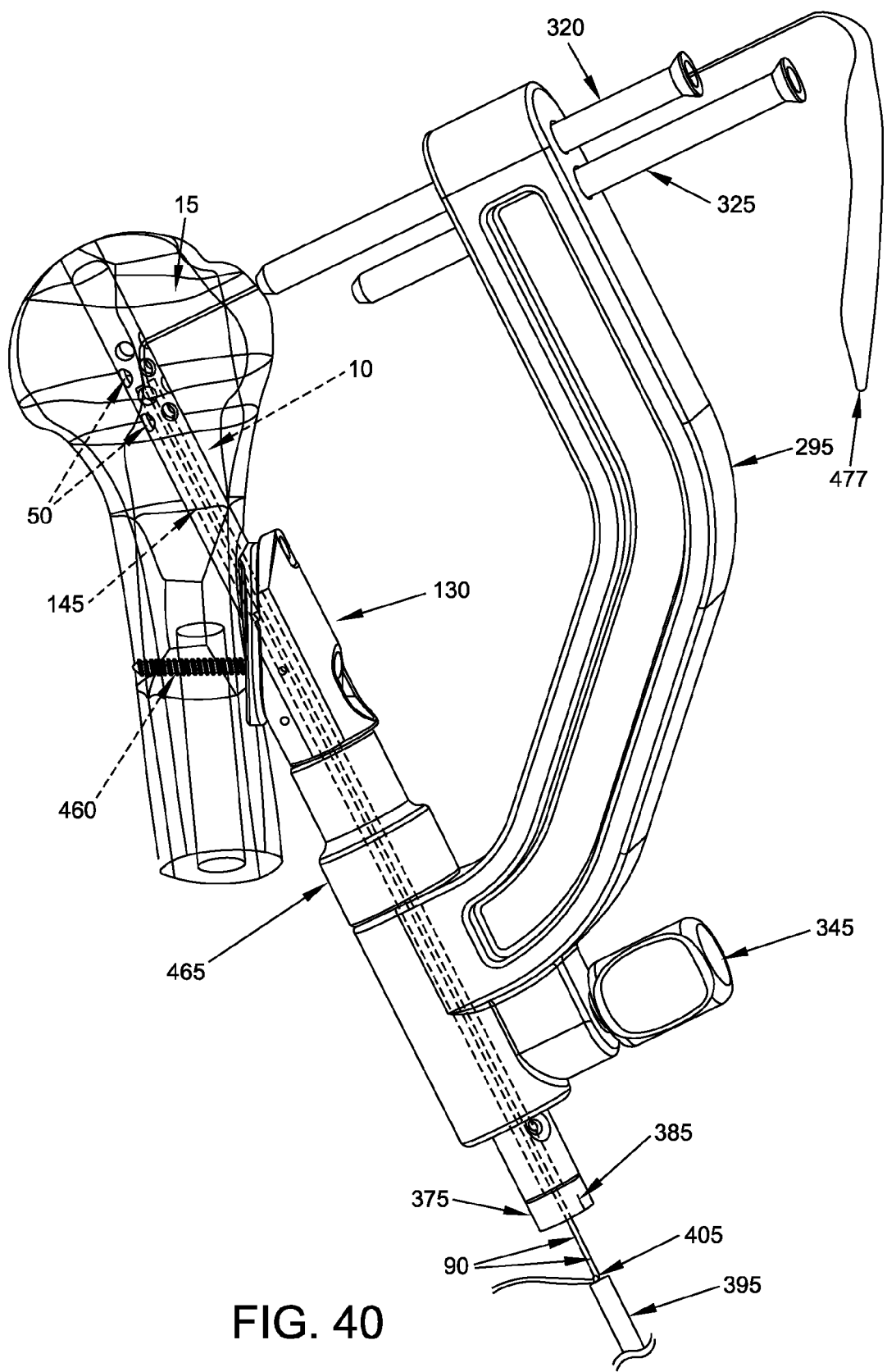

17. Suture retriever 145 is withdrawn from anchoring tube 10 and inserter 130 (FIG. 40), whereby to cause the two free ends of suture 90 to extend through proximal humerus 15, down anchoring tube 10 and out inserter 130. The closed loop 477 of suture 90 will remain protruding from the proximal end of a drill sleeve.

Figure 41:
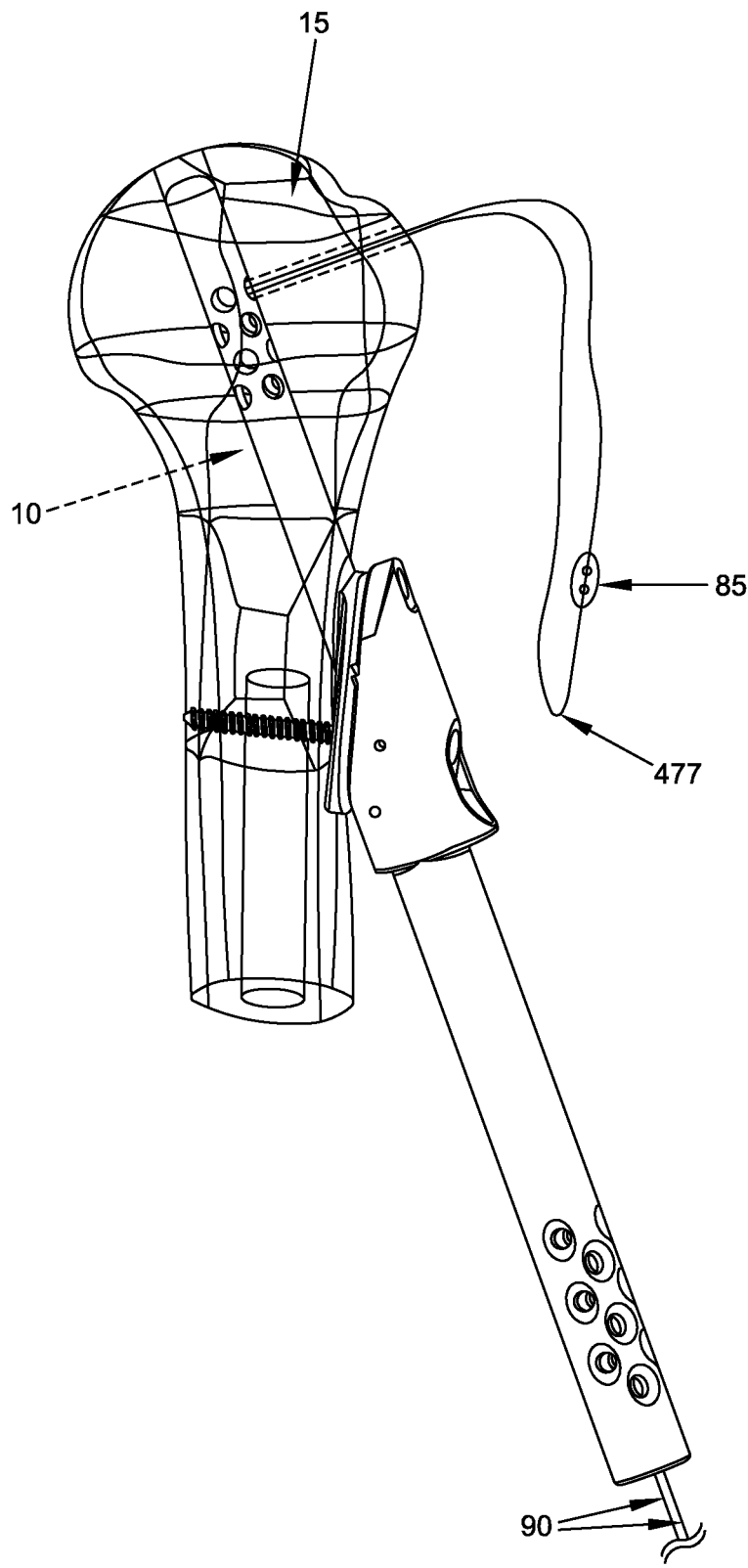

18. Drill sleeves 320, 325 are removed from crossbore aimer 140, and crossbore aimer 140 is removed from inserter 130 (FIG. 41). Buckle 85 can then be attached to the portion of closed loop 477 of suture 90 which extends out of proximal humerus 15. This may be done by passing closed loop 477 of suture 90 through first hole 110 of buckle 85. After passing closed loop 477 through first hole 110 of buckle 85, closed loop 477 is then passed over bridge 120 of buckle 85 and through second hole 115 of buckle 85. Next, closed loop 477 is passed over second end 105 of buckle 85, so that one strand of closed loop 477 slides along each side of buckle 85. Finally, closed loop 477 is passed over first end 100 of buckle 85, and the suture is pulled taut, thereby securing buckle 85 to closed loop 477. See FIG. 41.

Figure 42:
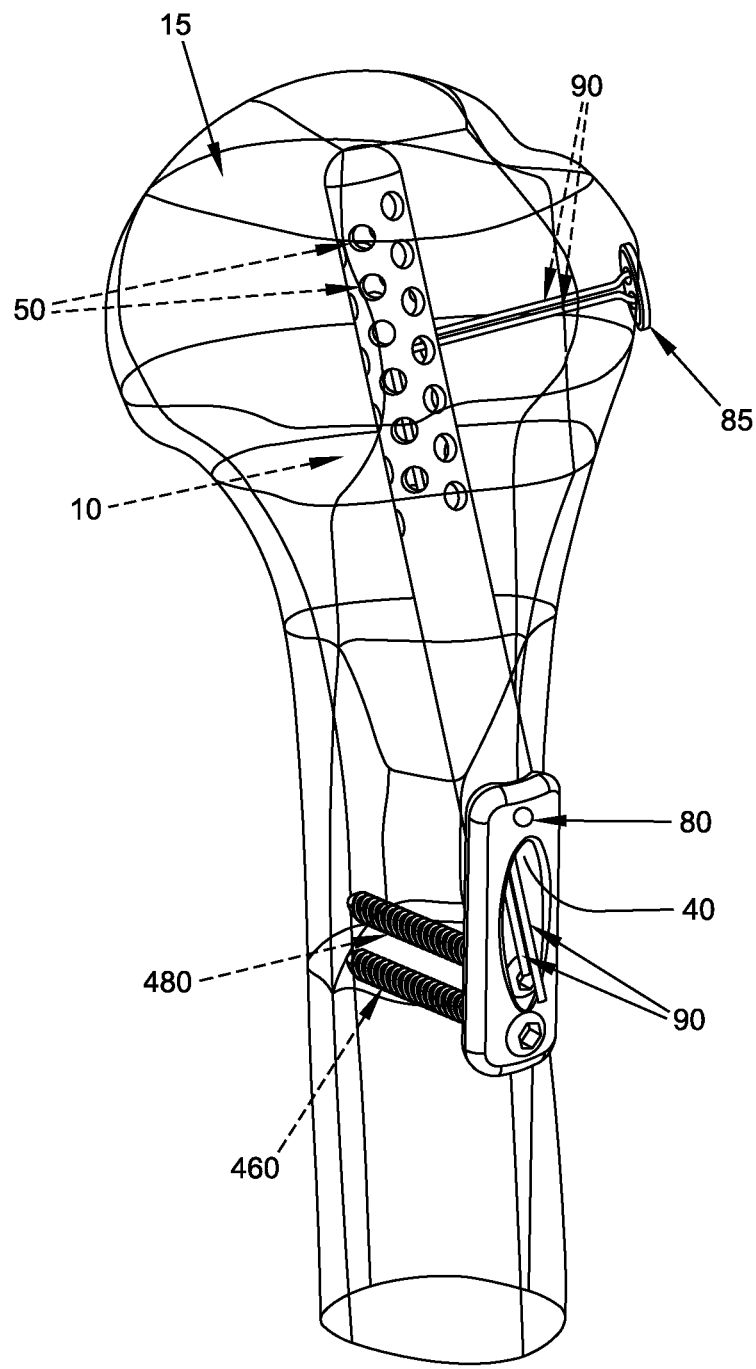

19. After buckle 85 has been mounted to suture 90, inserter 130 is removed from anchoring tube 10 (alternatively, inserter 130 may be removed from anchoring tube 10 before buckle 85 is mounted to suture 90). Then the two free ends of suture 90 are pulled taut so as to pull buckle 85 of the suture assembly against the outer surface of the bone fragment, and a screw 480 is passed through hole 70 in anchoring tube 10, with screw 480 securing the two free ends of suture 90 to the anchoring tube under tension (FIG. 42). As a result of the foregoing, the tensioned suture assembly 20 will secure the bone fragment to anchoring tube 10 and, as a result, will secure the bone fragment to proximal humerus 15.

Figure 43:
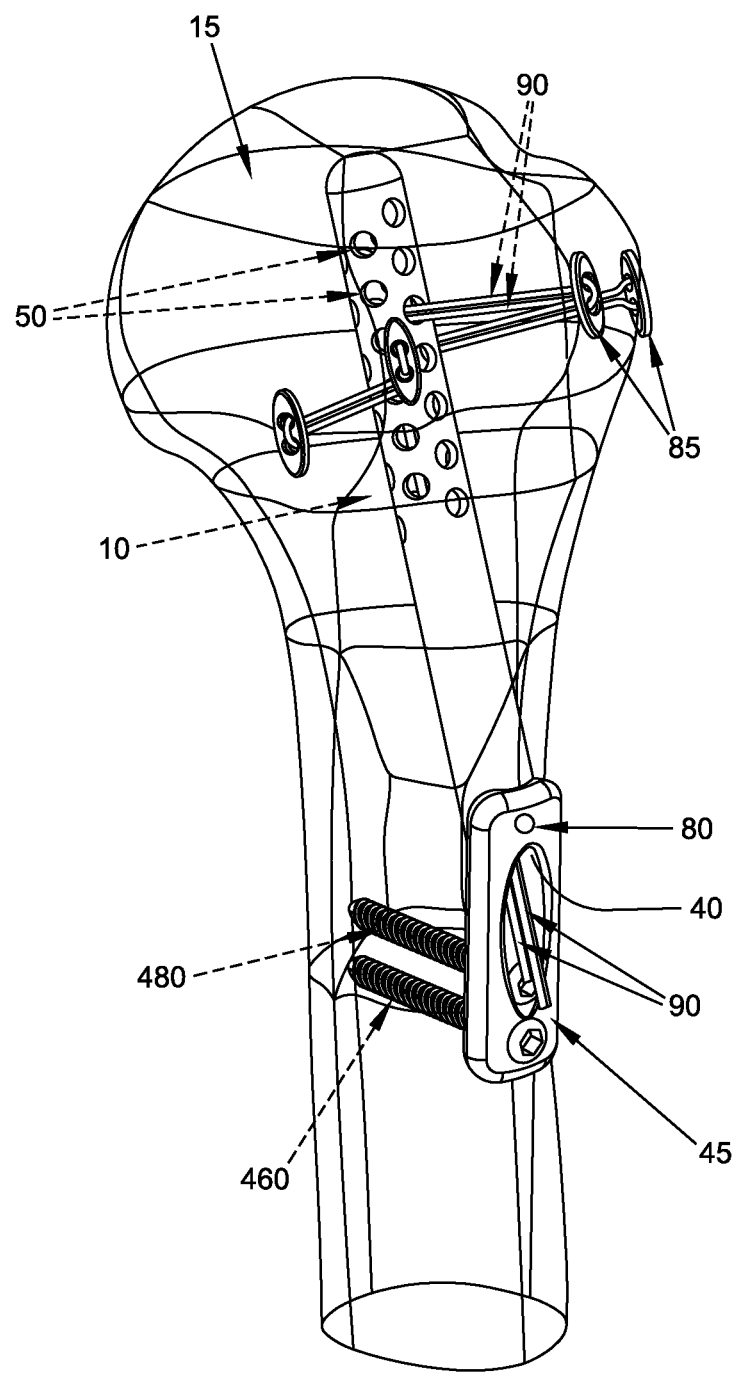

If desired, the foregoing procedure may be used to position multiple suture assemblies 20 in proximal humerus 15 (FIG. 43), thereby providing the opportunity to fix multiple bone fragments to proximal humerus 15.

Alternative Suture Assembly

Figure 44:
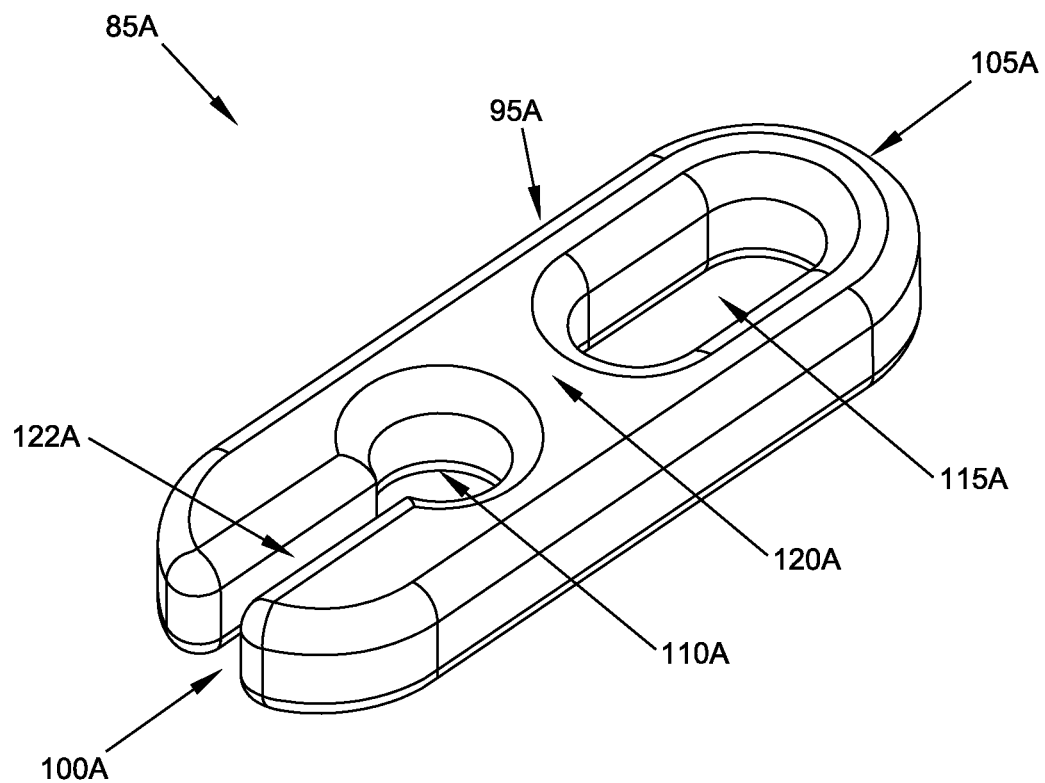
FIG. 44 is a schematic view showing an alternative suture assembly buckle formed in accordance with the present invention.
Figure 45:
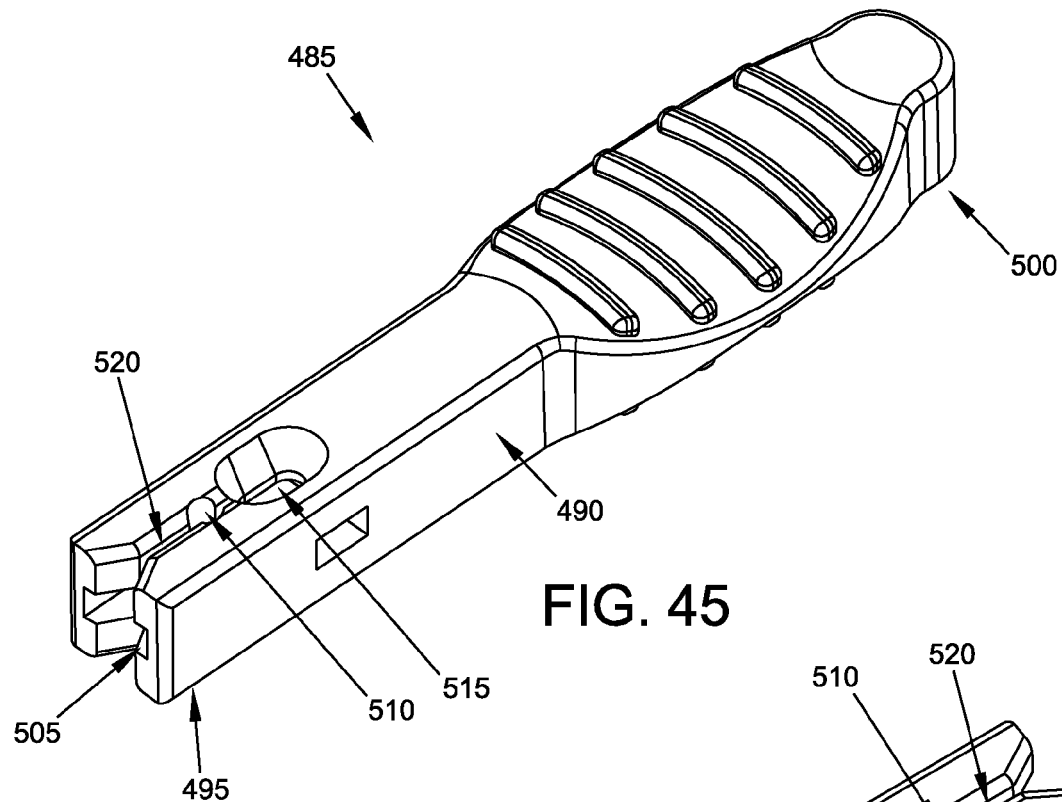
FIGS. 45-47 are schematic views showing a buckle holder which may be used in conjunction with the suture assembly buckle shown in FIG. 44.
Figure 46:
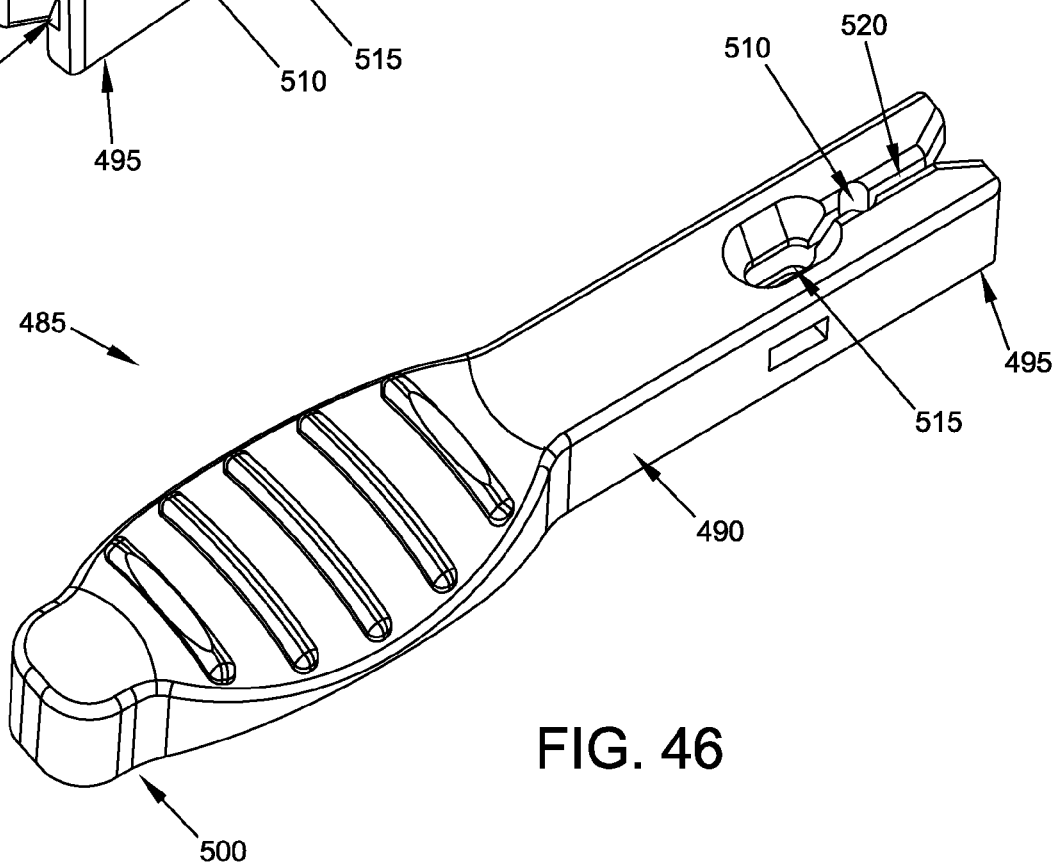
Figure 47:
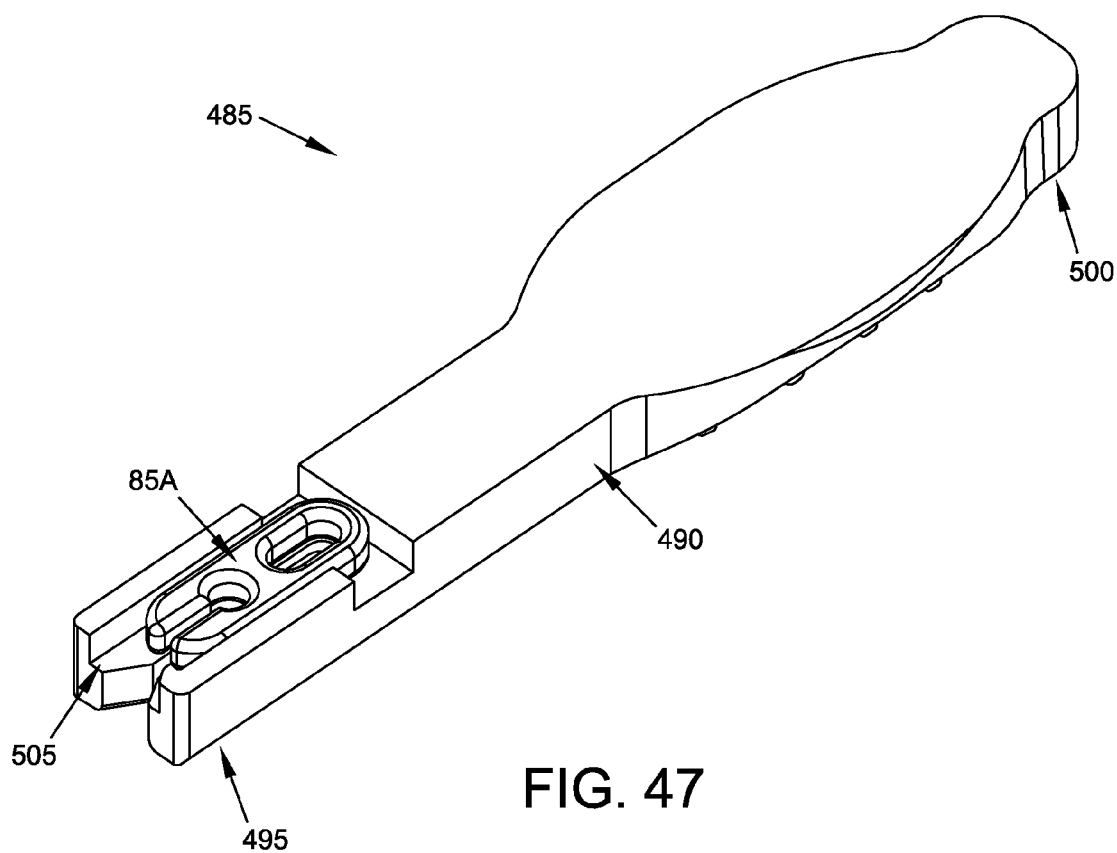

If desired, a novel buckle 85A (FIG. 44) may be utilized, together with a novel buckle holder 485 (FIGS. 45-47).

Buckle 85A comprises an elongated body 95A having a first end 100A and a second end 105A, and a first hole 110A and a second hole 115A. A bridge 120A is disposed between first hole 110A and second hole 115A. A slot 122A connects first hole 110A with first end 100A.

Novel buckle holder 485 comprises a shaft 490 having a distal end 495 and proximal end 500. A horizontal slot 505 opens on distal end 495 and extends into buckle holder 485. Horizontal slot 505 (FIG. 45) is sized so as to receive buckle 85A therein (FIG. 47). A first hole 510 and a second hole 515 extend from one side of buckle holder 485 to the other side of buckle holder 485, passing through slot 505. A vertical slot 520 opens on distal end 495 and extends into buckle holder 485. Vertical slot 520 intersects both first hole 510 and second hole 515.

Figure 48:
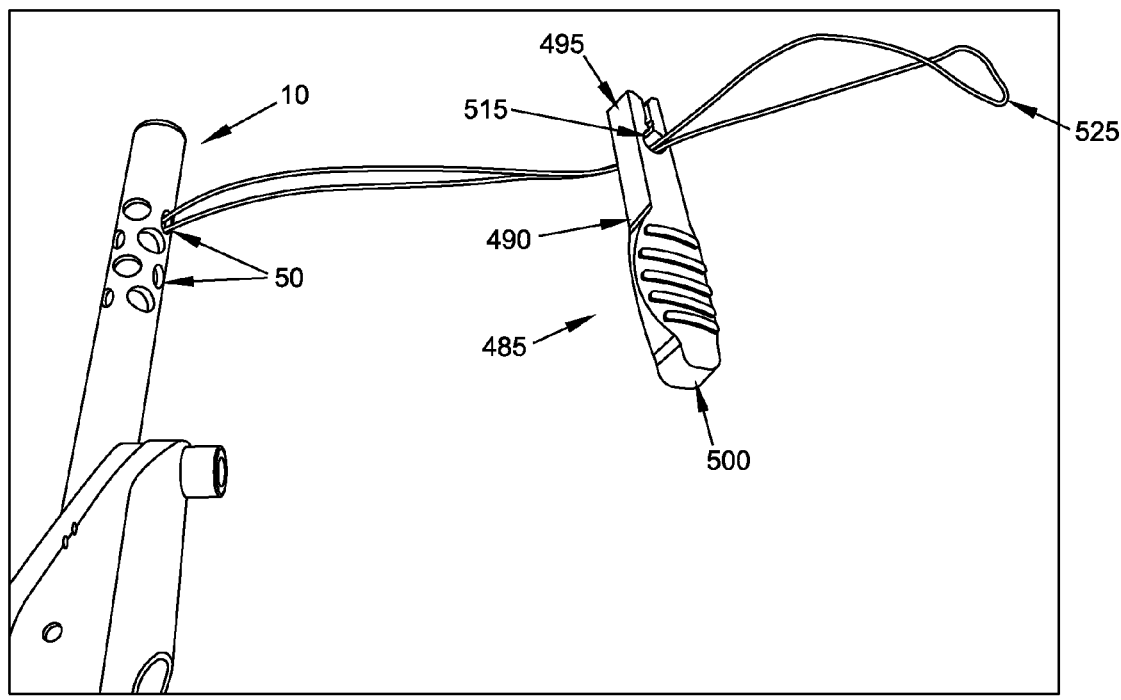
FIGS. 48-56 are schematic views showing a suture being mounted to the suture assembly buckle shown in FIG. 44 using the buckle holder shown in FIGS. 45-47.
Figure 49:
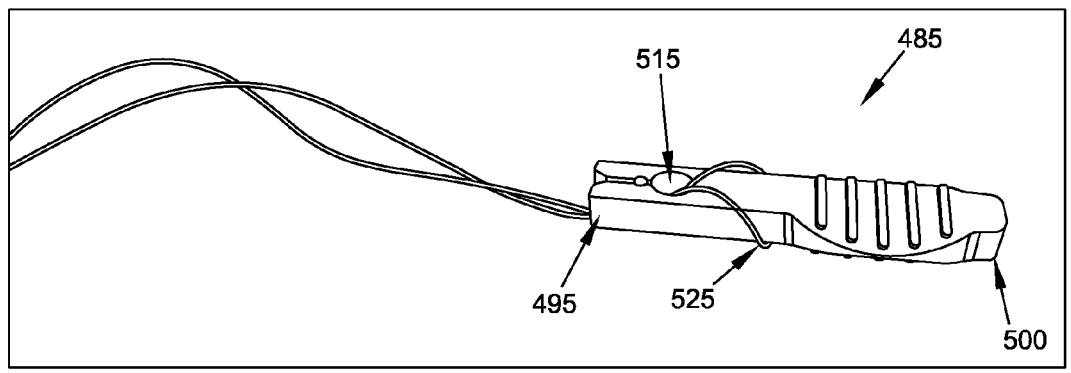
Figure 50:
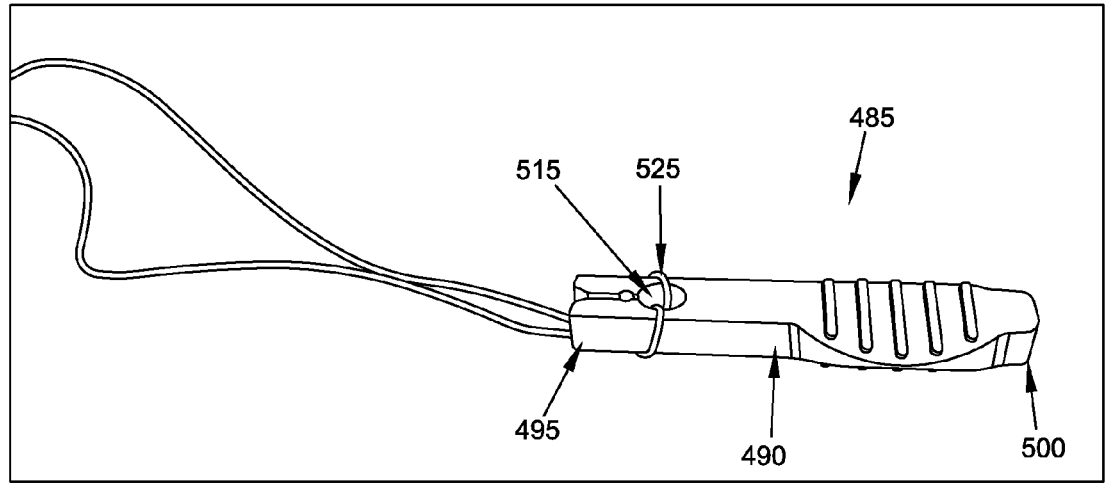
Figure 51:
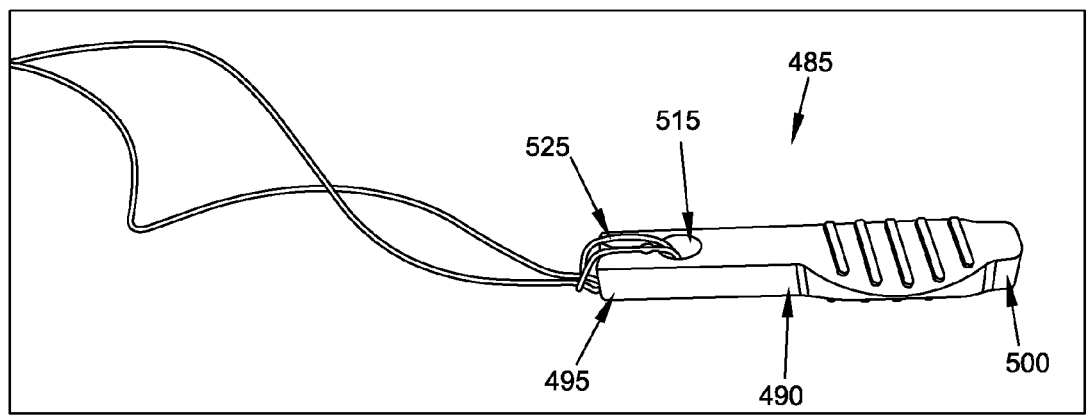
Figure 52:
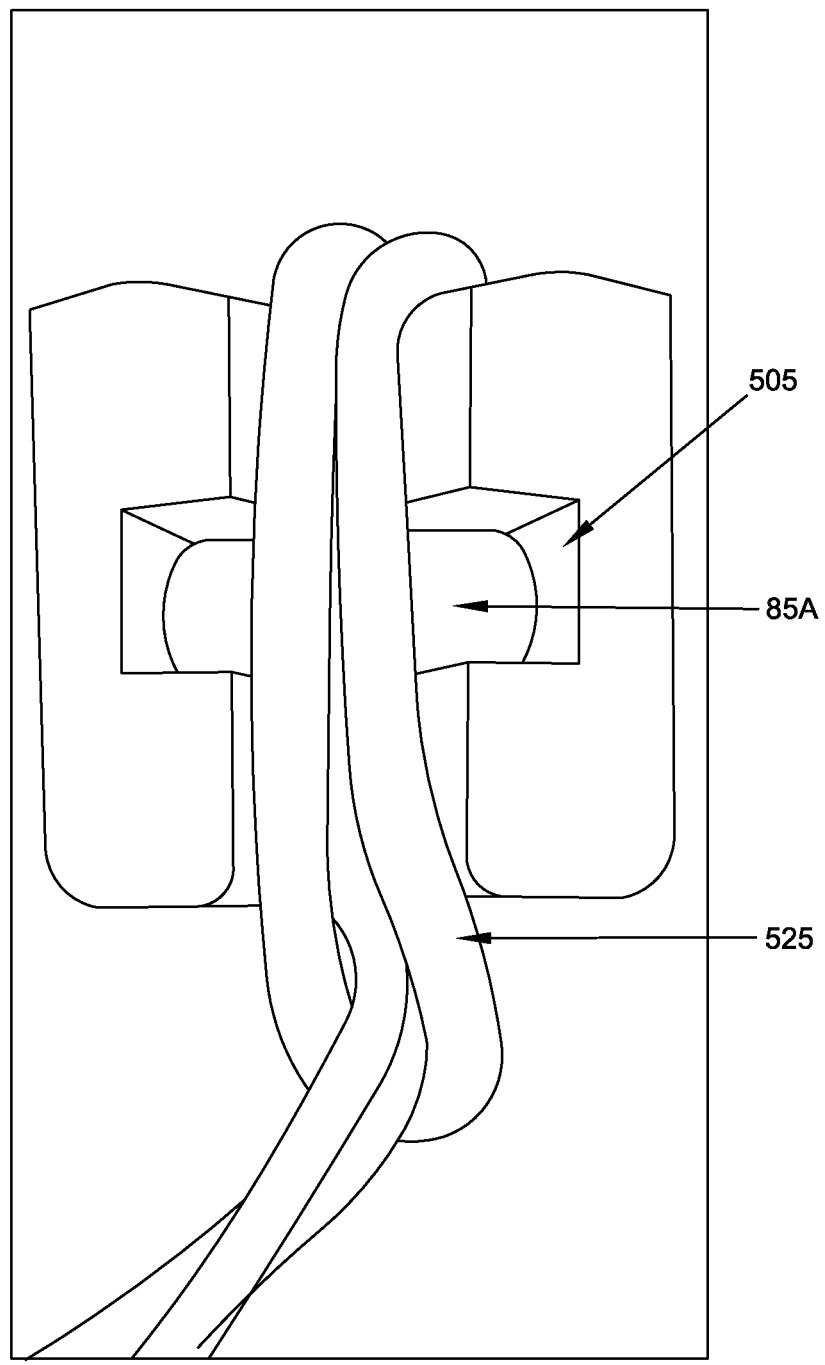
Figure 53:
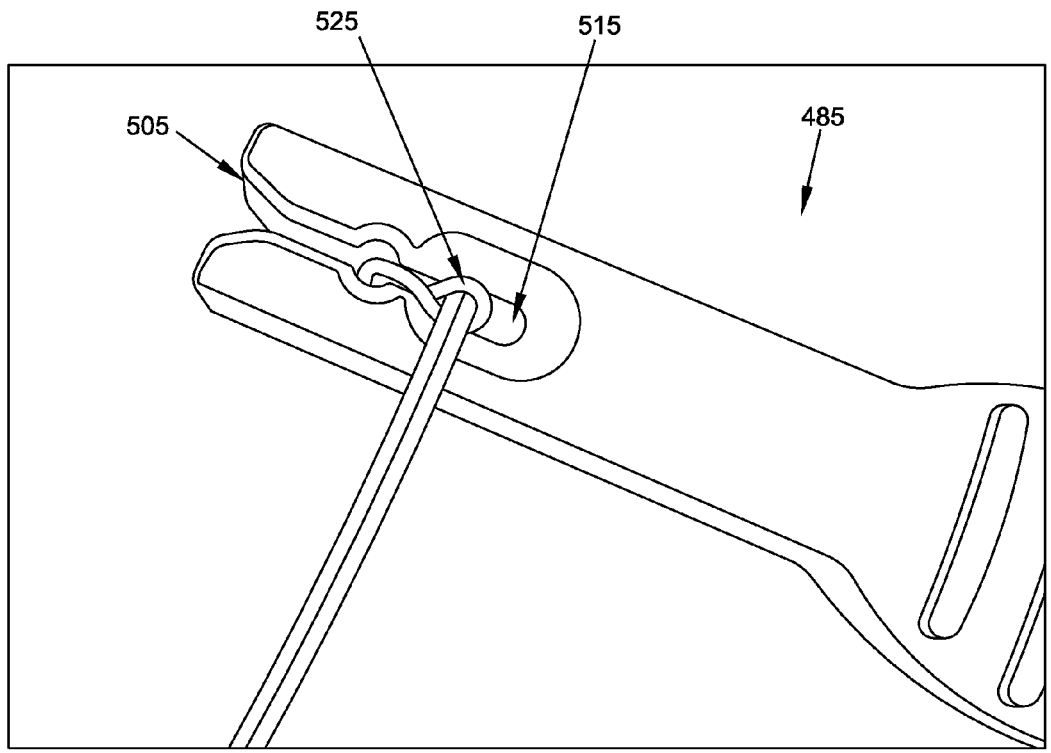
Figure 54:
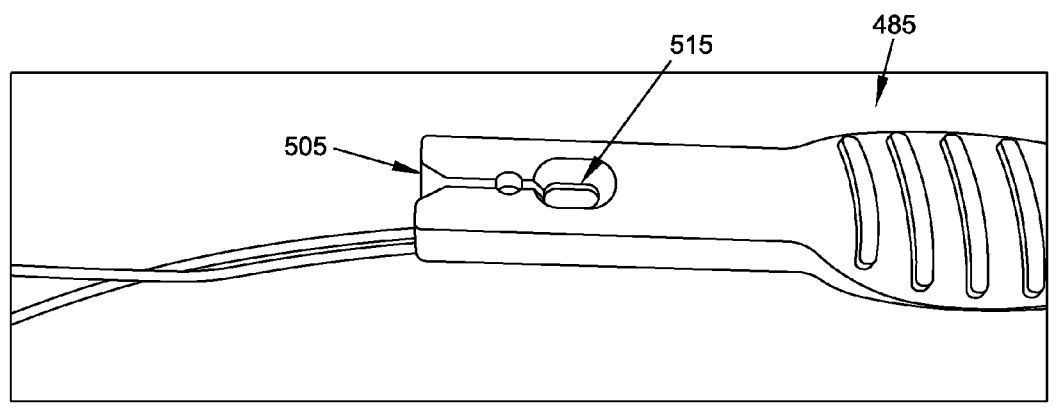
Figure 55:
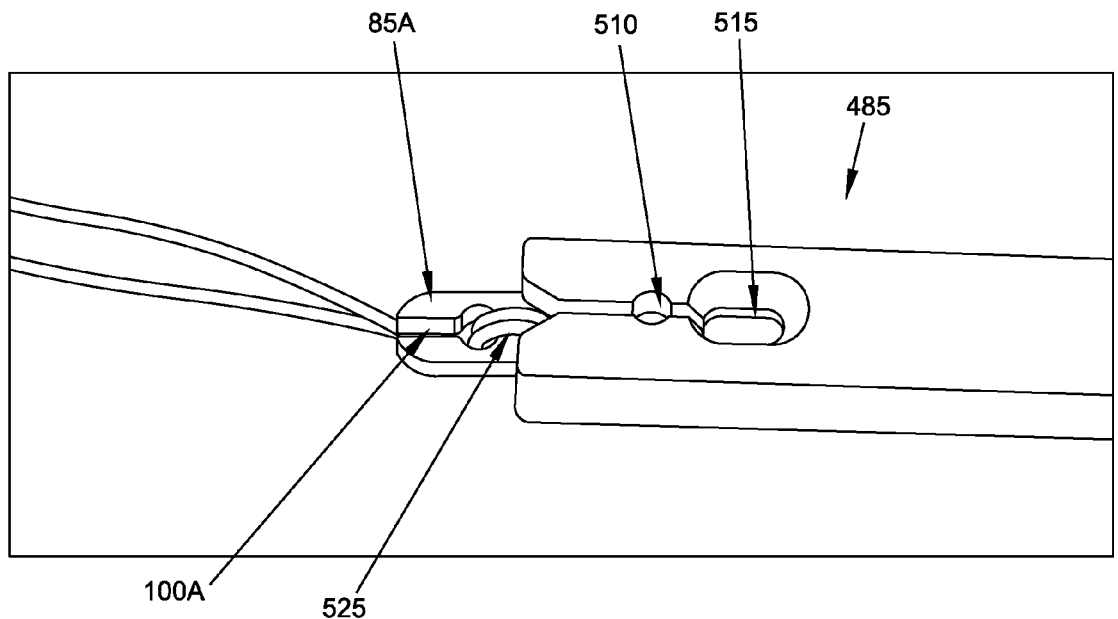
Figure 56:
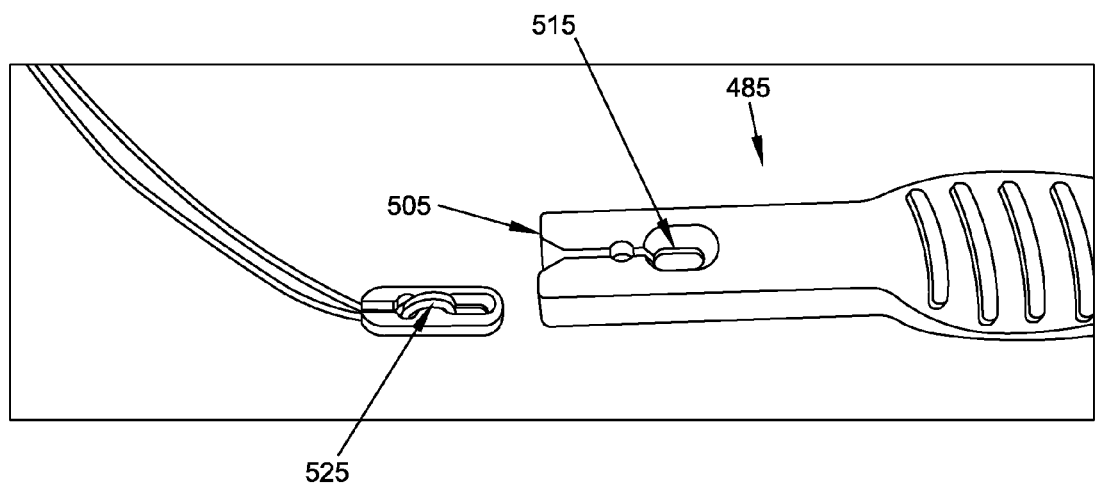

Looking now at FIGS. 47-56, buckle 85A may be loaded onto a suture 90 (which has already been threaded through proximal humerus 15, anchoring tube 10 and inserter 130) in the following manner. First, buckle 85A is loaded into horizontal slot 505 of buckle holder 485 so that first hole 110A of buckle 85A is aligned with first hole 510 of buckle holder 485, second hole 115A of buckle 85A is aligned with second hole 515 of buckle holder 485, and slot 122A of buckle 85A is aligned with vertical slot 520 in buckle holder 485 (FIG. 47). Then the loop 525 emanating from anchoring tube 10 and proximal humerus 15 is passed through second hole 515 of buckle holder 485 and second hole 115A of buckle 85A (FIG. 48). Loop 525 is looped around the proximal end 500 of shaft 490 of buckle holder 485 (FIG. 49) and moved along the body of shaft 490 (FIG. 50) to a point distal to distal end 495 (FIGS. 51 and 52). The two free ends of suture 90 are then tensioned, drawing loop 525 along vertical bore 520 and into second hole 515 of buckle holder 485 (FIGS. 53 and 54). At this point, suture 90 is wound around bridge 120A of buckle 85A. Then buckle 85A may be pulled free from buckle holder 485 by pulling on the two free ends of suture 90, which slides buckle 85A out of horizontal slot 505 in buckle holder 485 (FIGS. 55 and 56), thereby completing the task of uniting buckle 85A and suture 90.

Fracture Fixation with Threaded Pins

Figure 57:
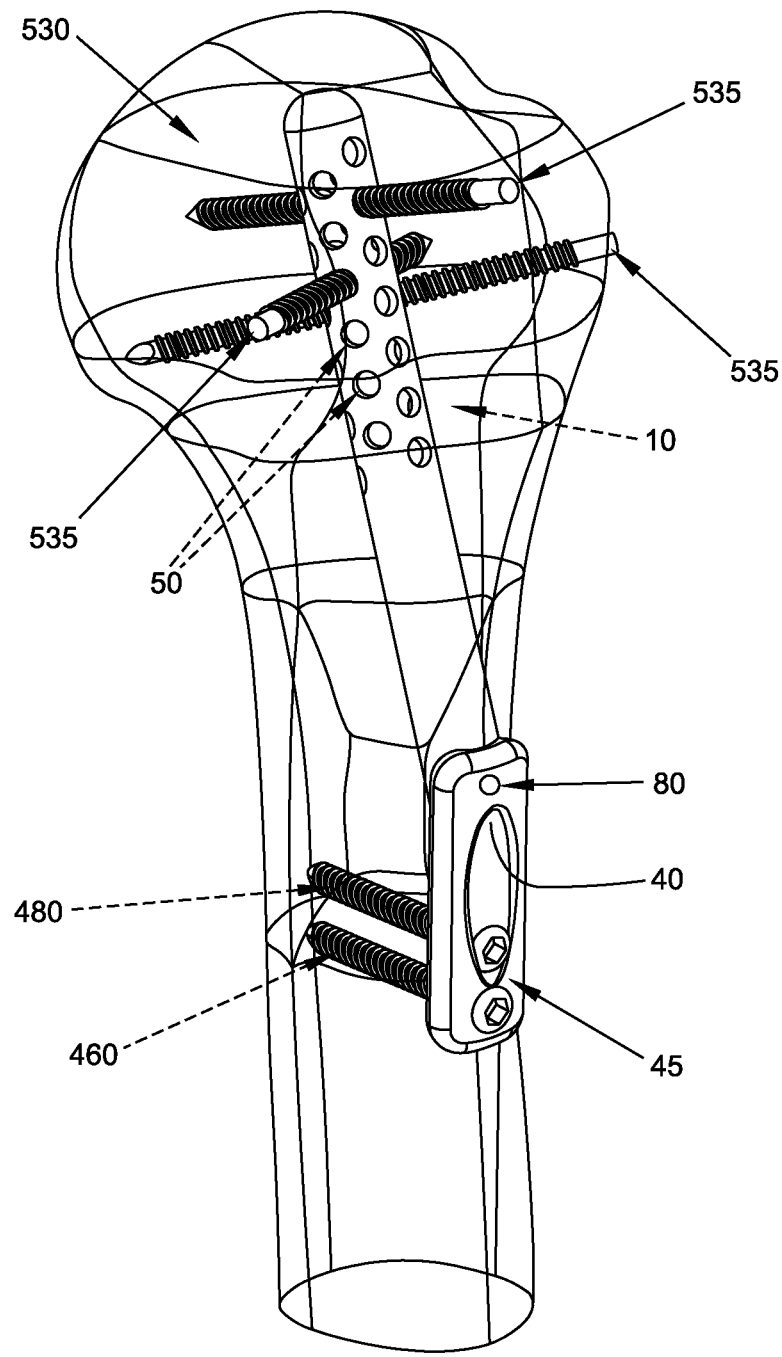
FIG. 57 is a schematic view showing fracture fixation in the proximal humerus using another novel fracture fixation apparatus formed in accordance with the present invention.

Looking next at FIG. 57, there is shown novel fracture fixation apparatus 530 for treating bone fractures in general, and for treating proximal humeral fractures in particular. As seen in FIG. 57, novel fracture fixation apparatus 530 generally comprises the aforementioned anchoring tube 10 for disposition in proximal humerus 15, and one or more threaded pins 535 for securing bone fragments to anchoring tube 10 and, as a result, for securing bone fragments to proximal humerus 15. Except as will otherwise be described below, novel fracture fixation apparatus 530 is identical to novel fracture fixation apparatus 5 discussed above.

Figure 58:
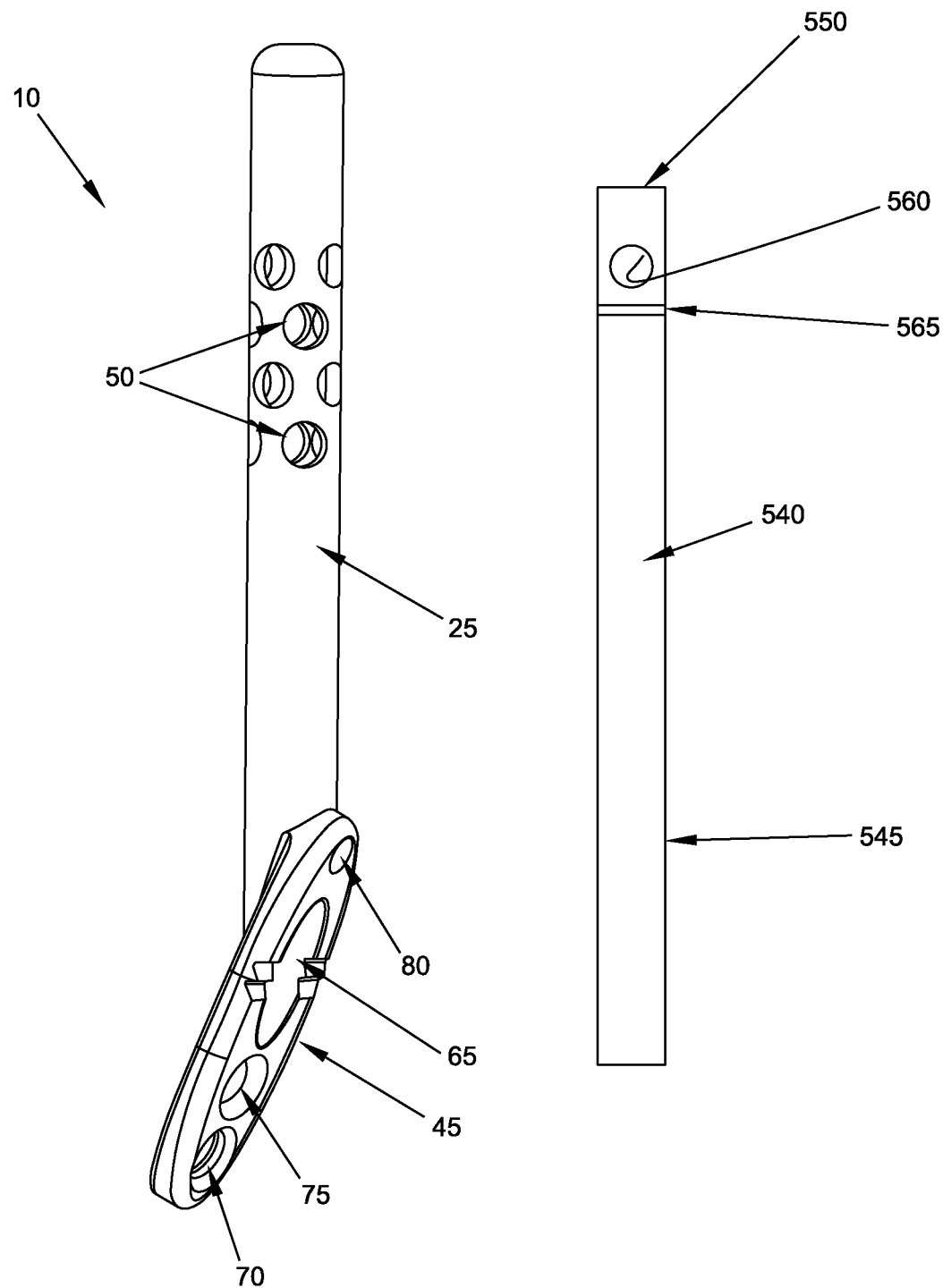
FIG. 58 is a schematic view showing apparatus for use with the novel fracture fixation apparatus shown in FIG. 57.

The primary differences between novel fracture fixation apparatus 530 and novel fracture fixation apparatus 5 are (i) the substitution of threaded pins 535 in place of suture assemblies 20, and (ii) the provision of a breakaway rod 540 (FIG. 58) for use in conjunction with threaded pins 535. Breakaway rod 540 comprises a shaft 545 having a distal end 550 and a proximal end 555, at least one transverse hole 560 extending through distal end 550, and a breakaway section 565 located proximal to the at least one transverse hole 560.

Figure 59:
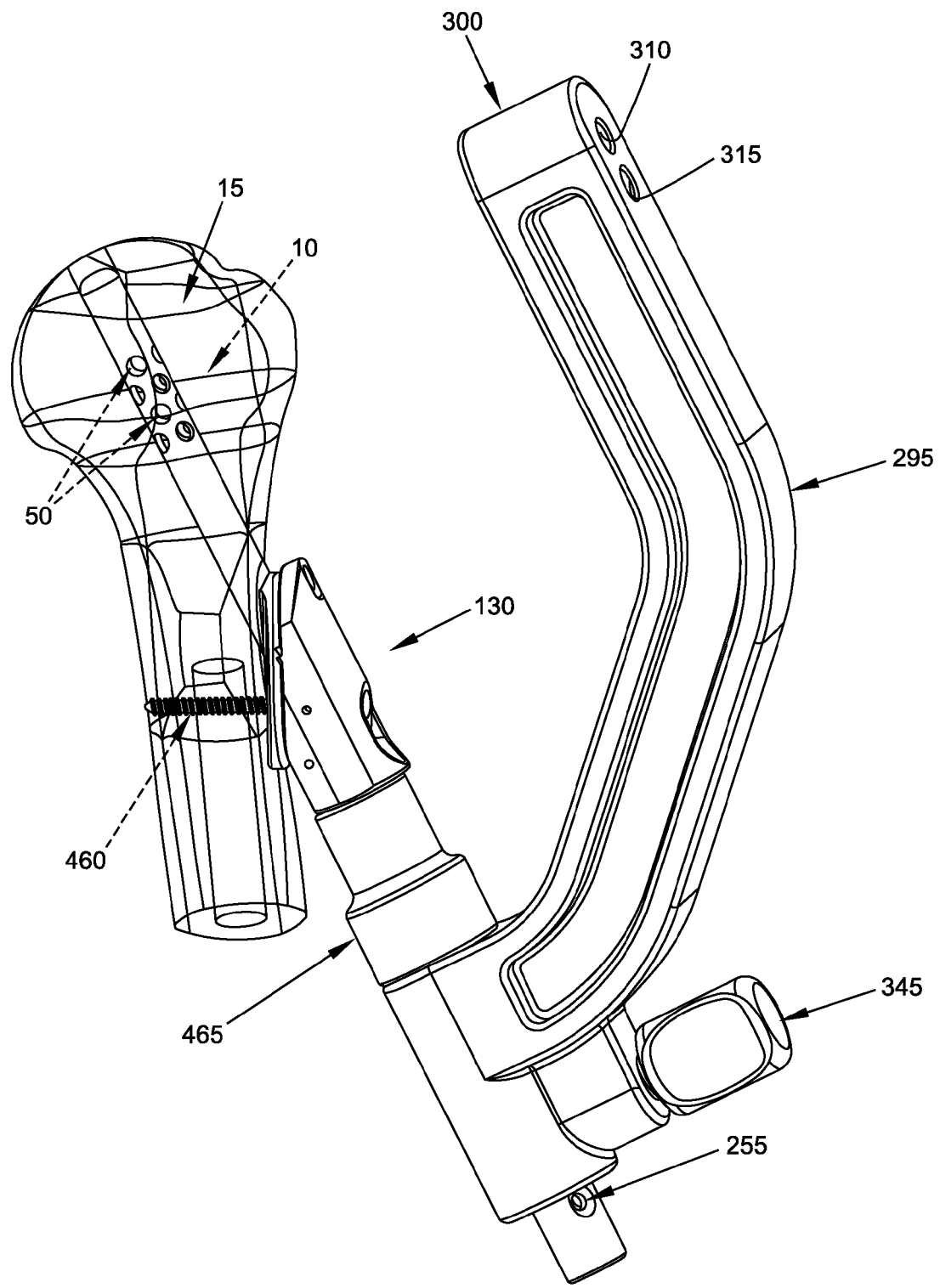
FIGS. 59-66 are schematic views showing fracture fixation in the proximal humerus using the novel fracture fixation apparatus shown in FIG. 57.
Figure 60:
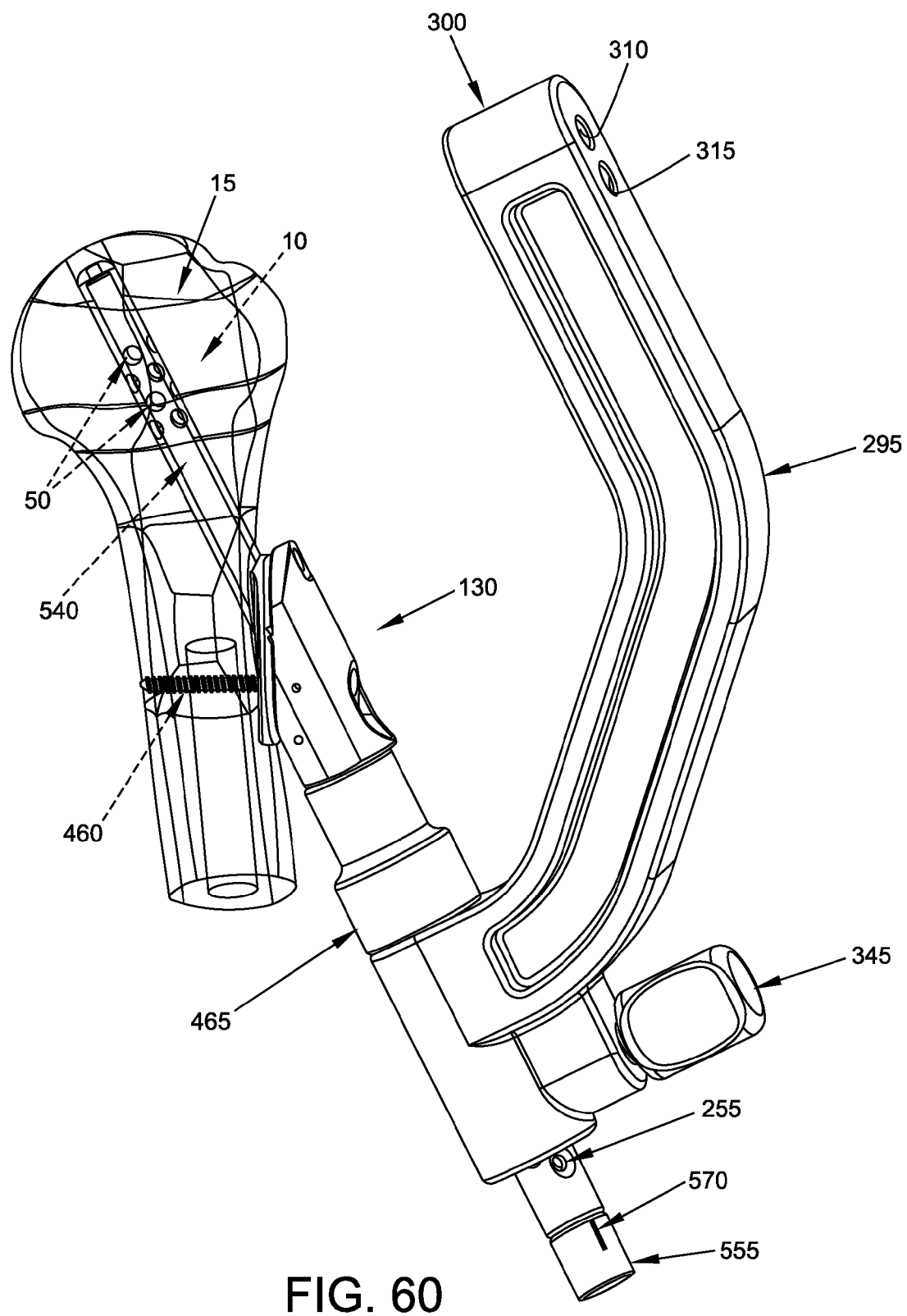
Figure 61:
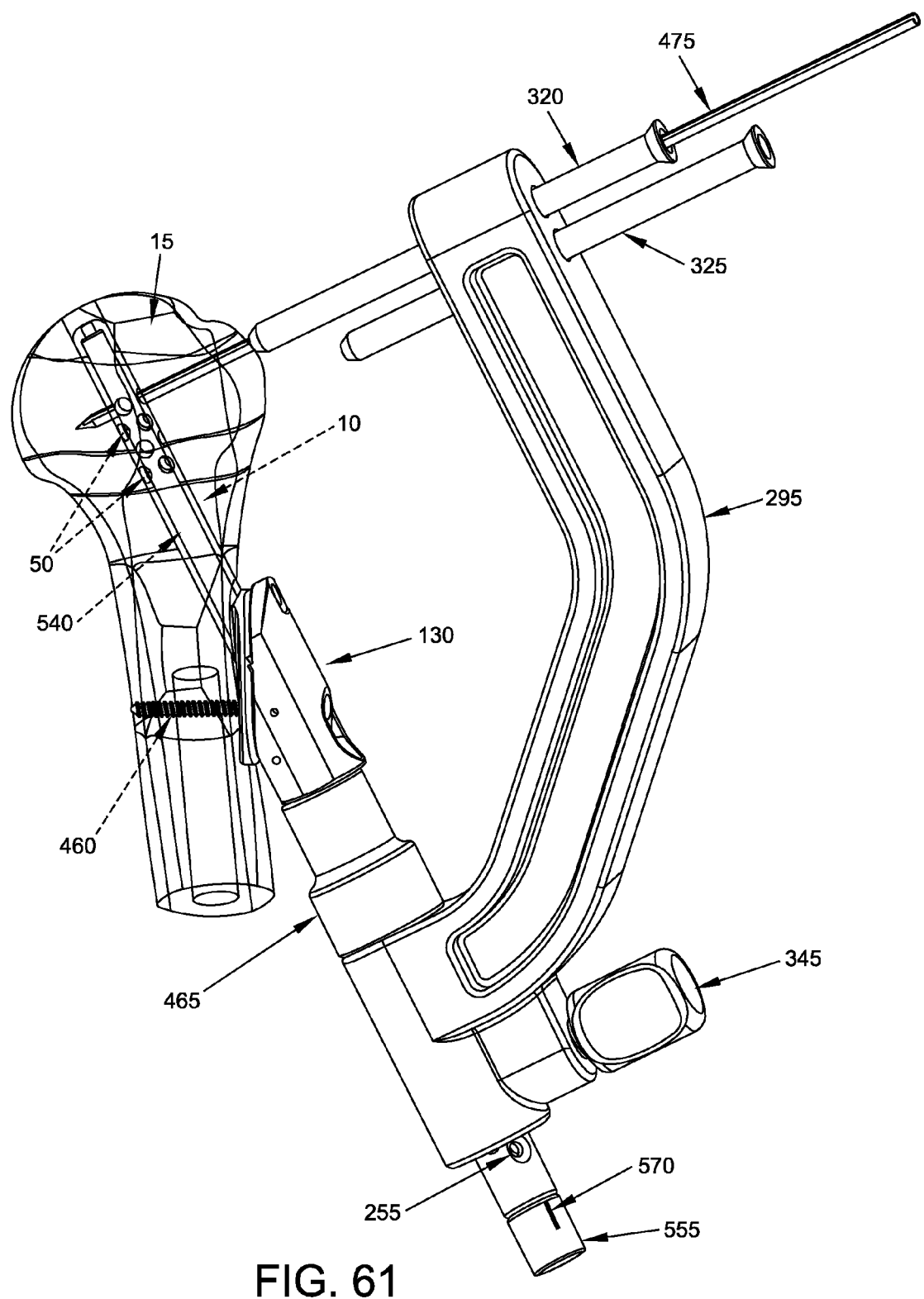
Figure 62:
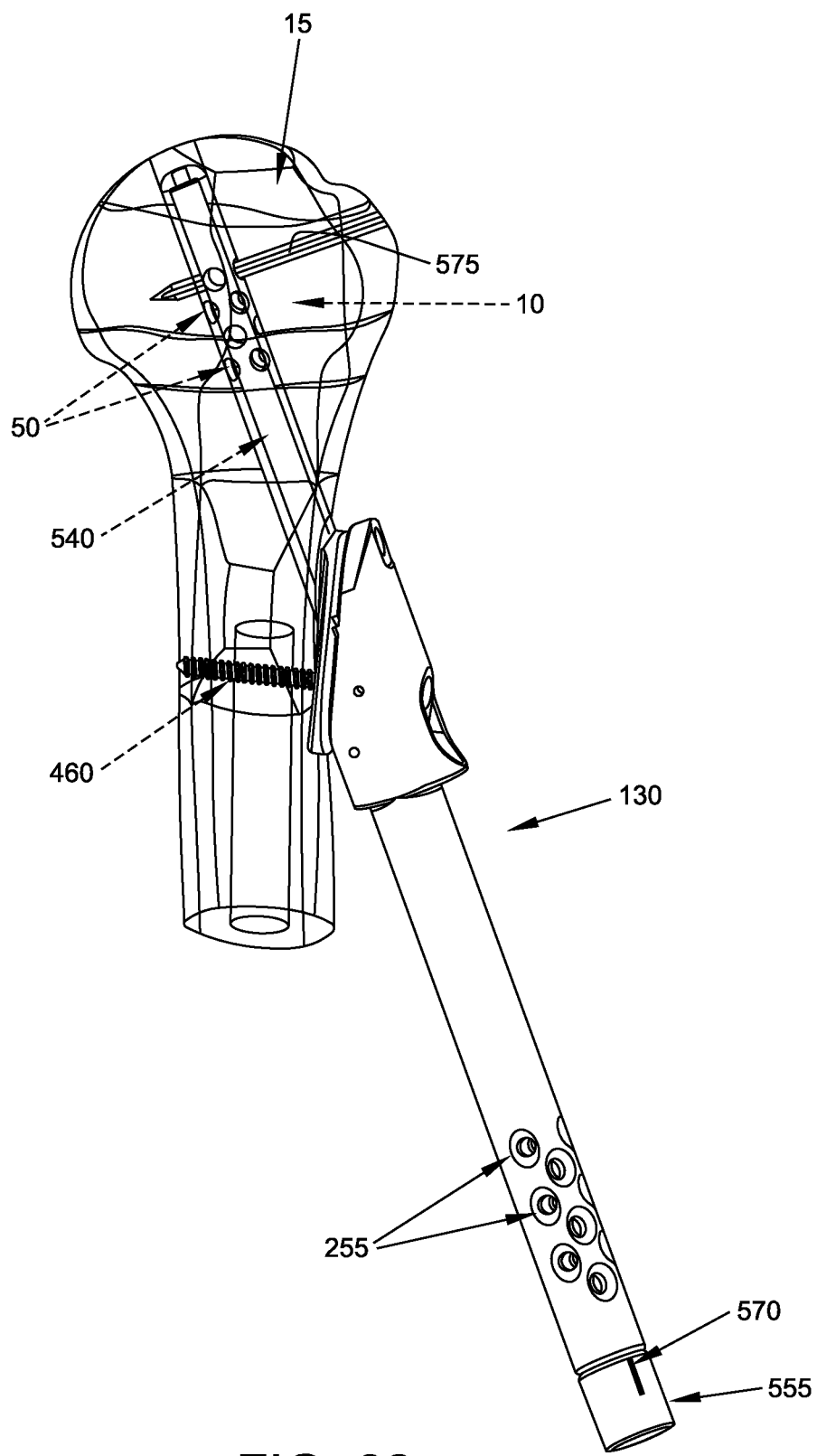
Figure 63:
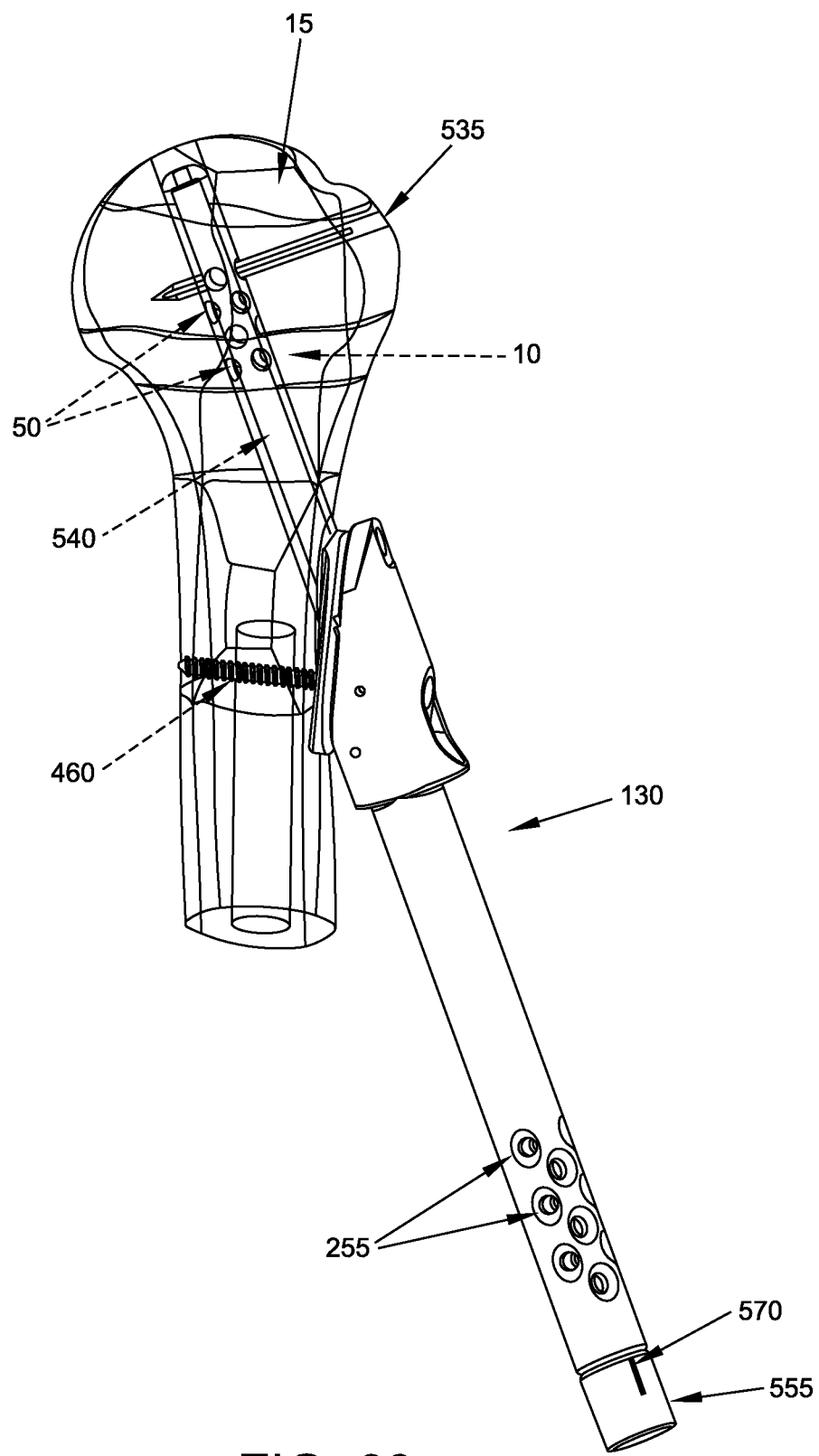
Figure 64:
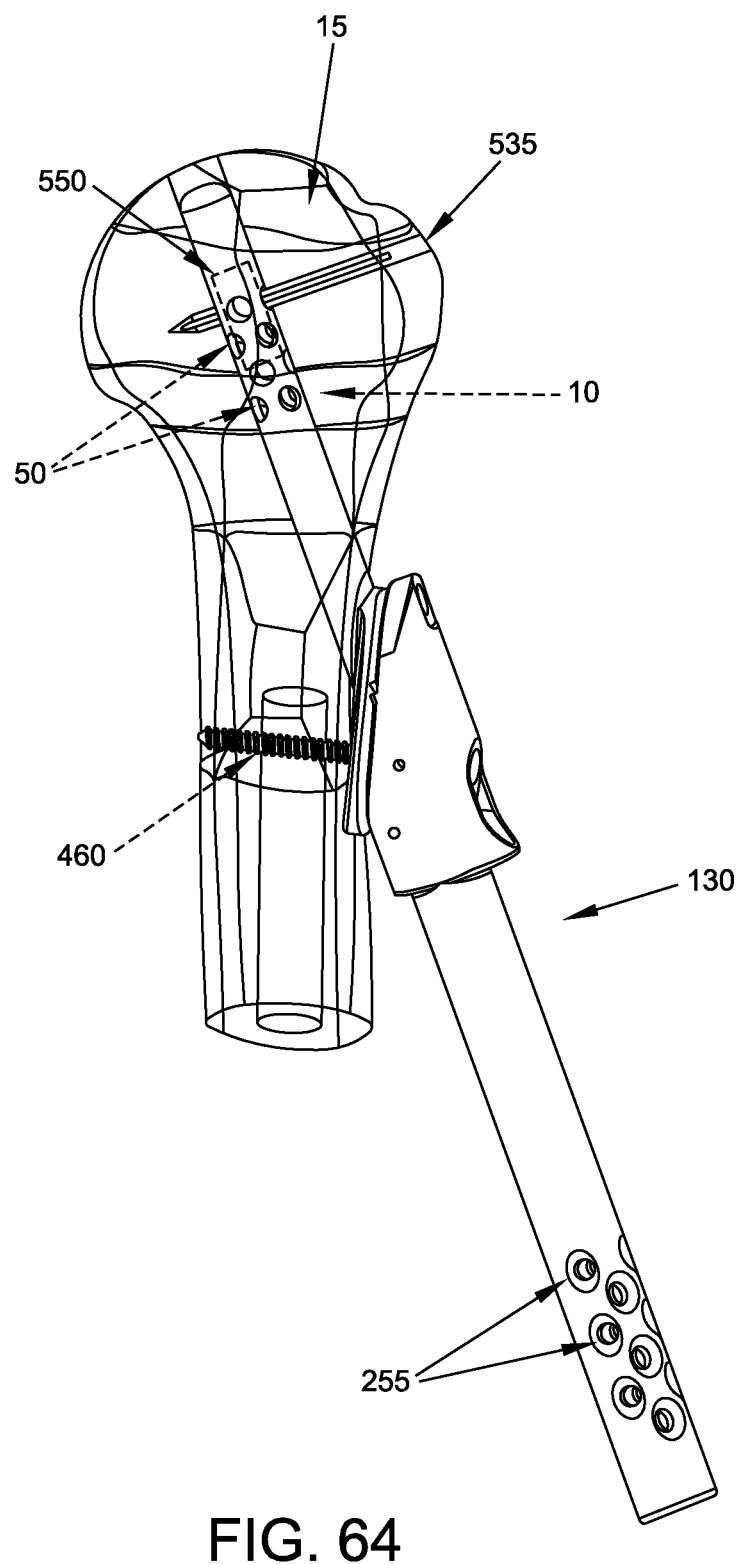
Figure 65:
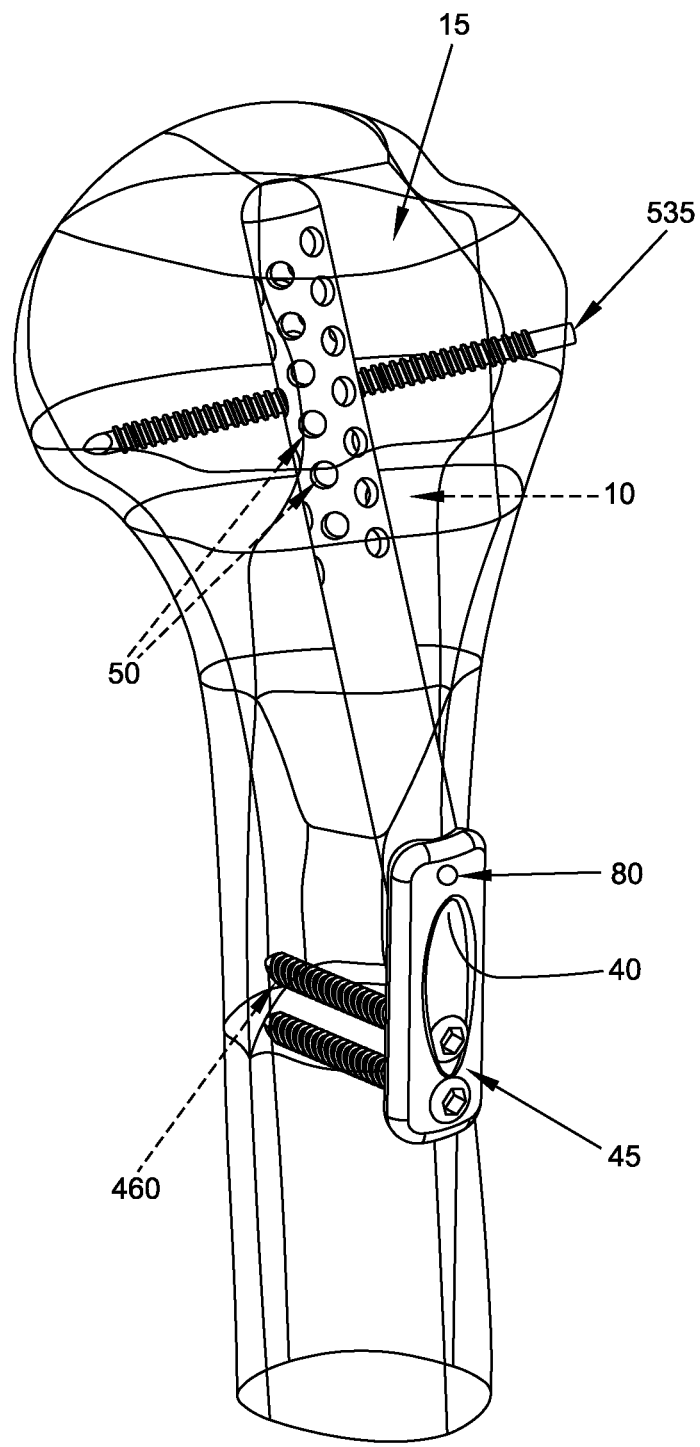

In use, novel fracture fixation apparatus 530 is used in a manner similar to novel fracture fixation apparatus 5, except that after the aforementioned step 10, when the apparatus is in the state shown in FIGS. 32 and 59, breakaway rod 540 is inserted up lumen 225 of inserter 130 and into lumen 40 of anchoring tube 10 (FIG. 60). Proper sizing of breakaway rod 540, and an appropriate marking 570 on proximal end 555 of breakaway rod 540, permits the at least one transverse hole 560 in breakaway rod 540 to be aligned with one or both of the holes 310, 315 in crossbore aimer 140. Thereafter, using drill sleeves 320, 325, drill 475 is advanced through proximal humerus 15, through two diametrically-opposed holes 50 in anchoring tube 10 and through the at least one transverse hole 560 in breakaway rod 540 (FIG. 61). Then cannulated drill 475, drill sleeves 320, 325 and crossbore aimer 140 are removed (FIG. 62), leaving a bore 575 extending through proximal humerus 15, two diametrically-opposed holes 50 in anchoring tube 10 and through the at least one transverse hole 560 in breakaway rod 540 (FIG. 62). Next, a threaded pin 535 is advanced through proximal humerus 15, two diametrically-opposed holes 50 in anchoring tube 10 and through the at least one transverse hole 560 in breakaway rod 540 (FIG. 63). At this point proximal end 555 of breakaway rod 540 is pulled proximally so as to cause breakaway rod 540 to separate at breakaway section 565 (FIG. 64). The distal section of breakaway rod 540 remains in anchoring tube 10, pierced by threaded pins 535, while the proximal section of breakaway rod 540 is removed. Then inserter 130 is removed, and screw 480 is passed through hole 470 in anchoring tube 10 (FIG. 65). As a result of the foregoing, threaded pin 535 will secure the bone fragment to anchoring tube 10 and, as a result, to proximal humerus 15.

Figure 66:
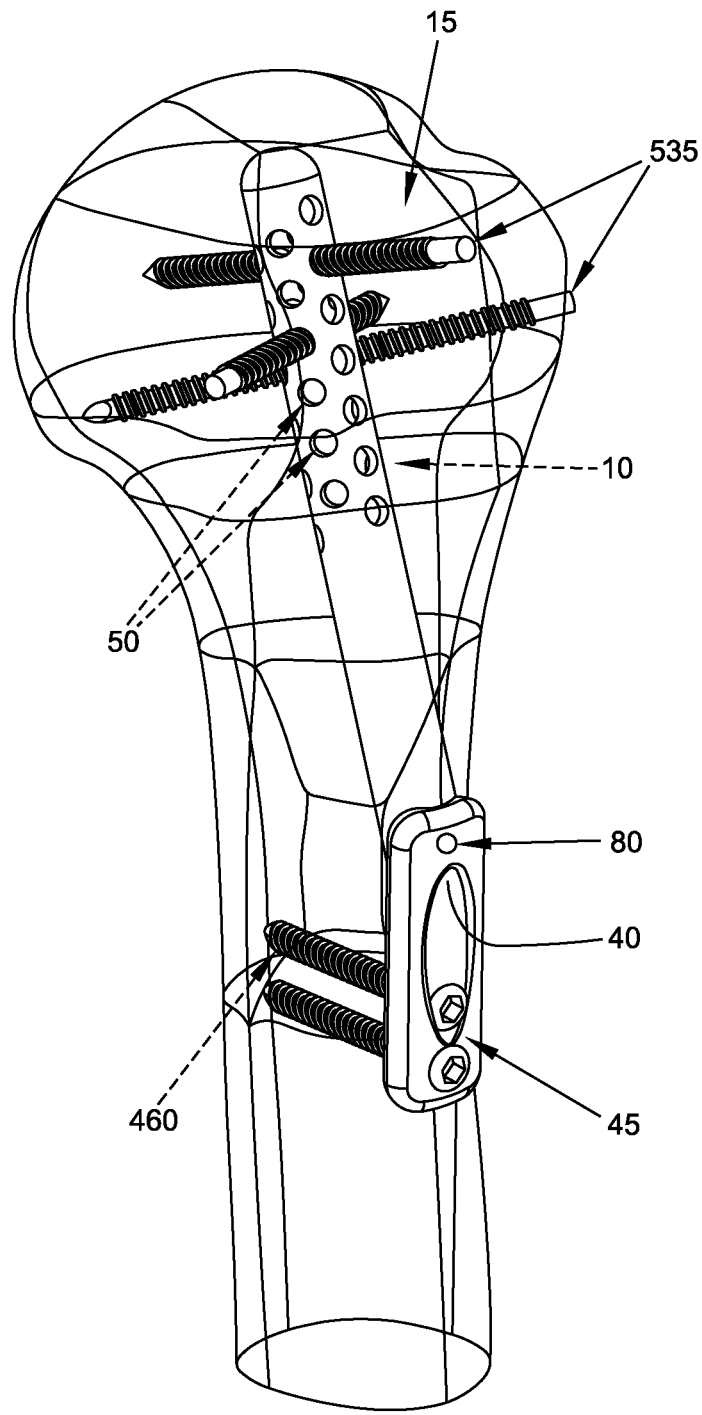

If desired, the foregoing procedure may be used to position multiple threaded pins 535 in proximal humerus 15 (FIG. 66), thereby providing the opportunity to fix multiple bone fragments to proximal humerus 15.

Fracture Fixation with Bone Screws

Figure 67:
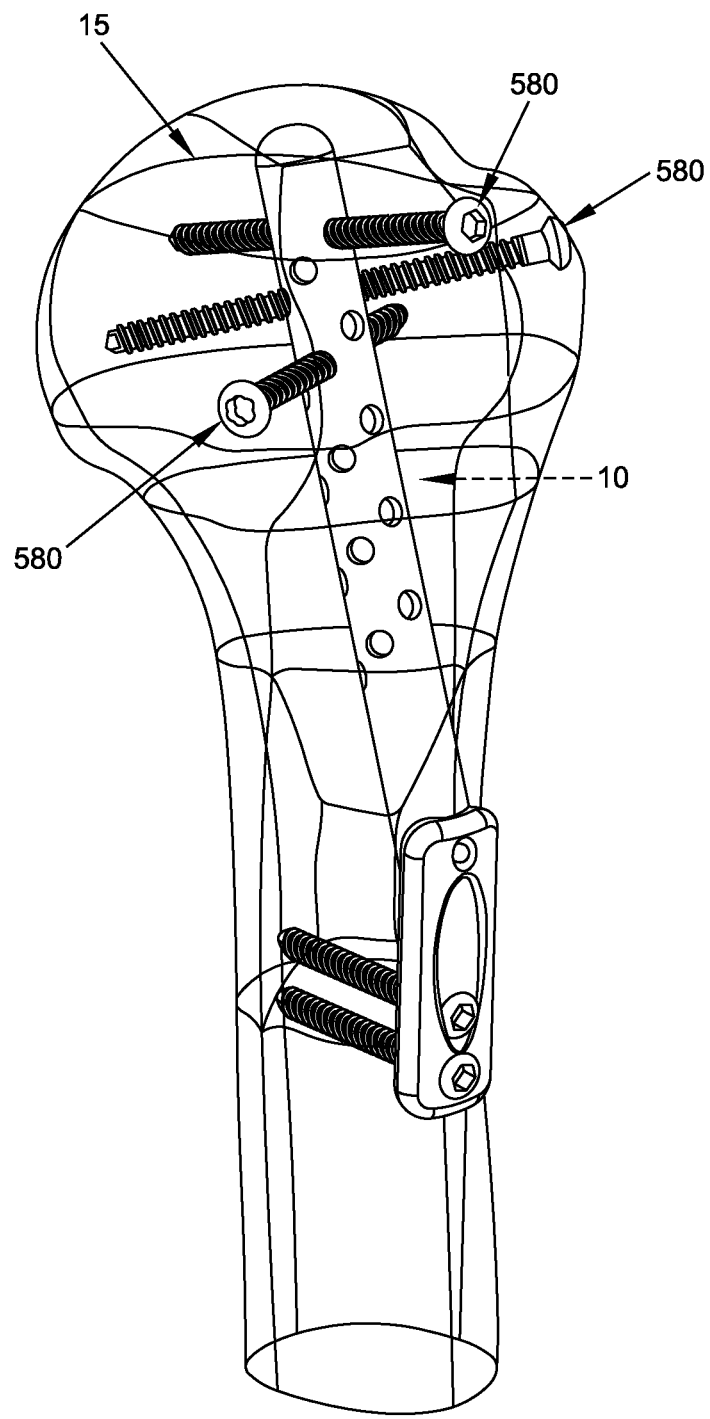
FIG. 67 is a schematic view showing a variation of the fracture fixation apparatus shown in FIG. 57.

If desired, and looking now at FIG. 67, bone screws 580 may be used in place of the aforementioned threaded pins 535. Preferably, bone screws 580 are cannulated and delivered over a guidewire.

Fracture Fixation with Projecting Barbs

Figure 68:
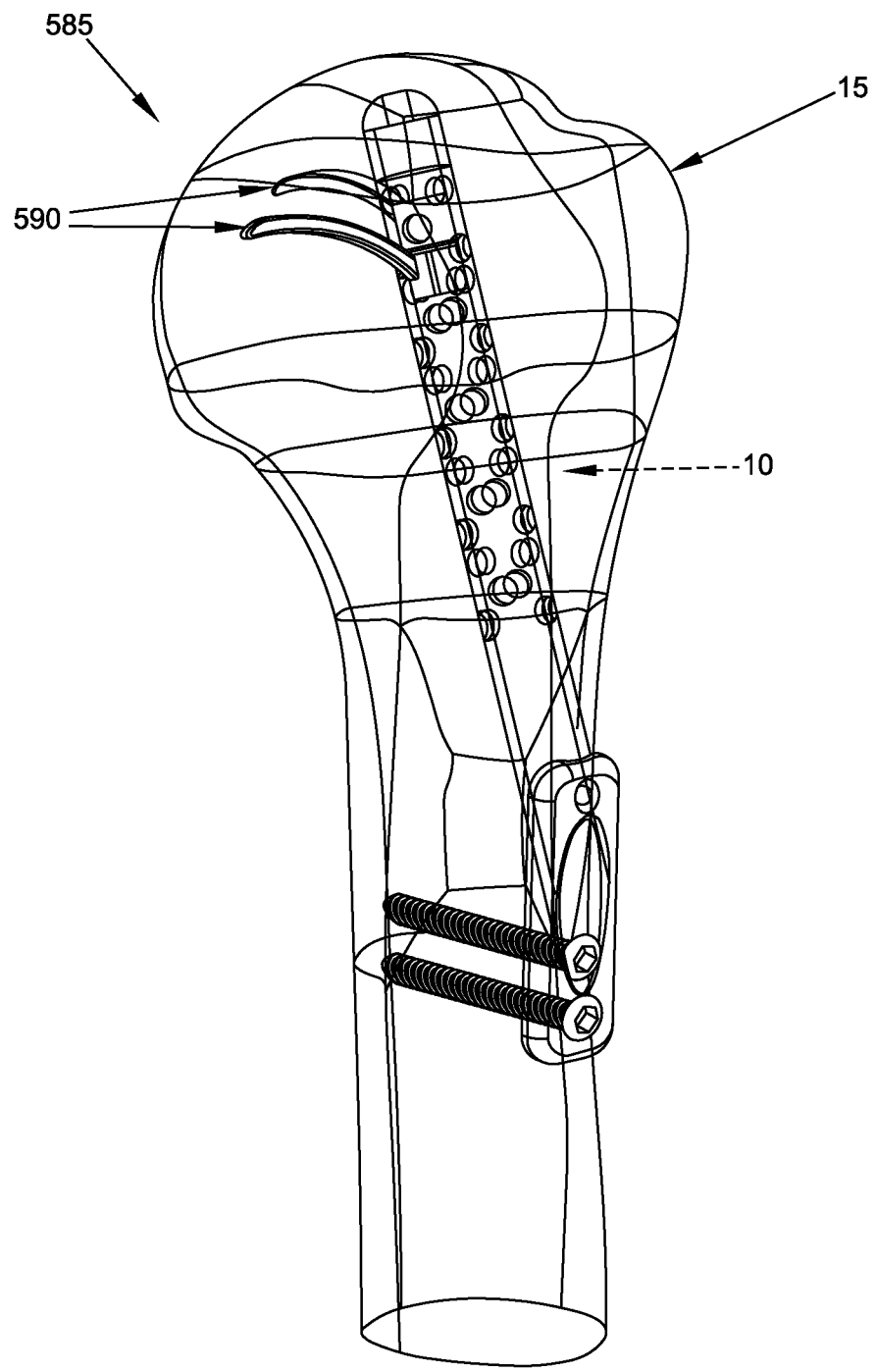
FIG. 68 is a schematic view showing fracture fixation in the proximal humerus using still another novel fracture fixation apparatus formed in accordance with the present invention.

Looking next at FIG. 68, there is shown novel fracture fixation apparatus 585 for treating bone fractures in general, and for treating proximal humeral fractures in particular. As seen in FIG. 68, novel fracture fixation apparatus 585 generally comprises the aforementioned anchoring tube 10 for disposition in a proximal humerus 15, and one or more projecting barbs 590 for securing bone fragments to anchoring tube 10 and, as a result, for securing bone fragments to proximal humerus 15. Except as will otherwise be described below, novel fracture fixation apparatus 585 is identical to novel fracture fixation apparatus 5 discussed above.

Figure 69:
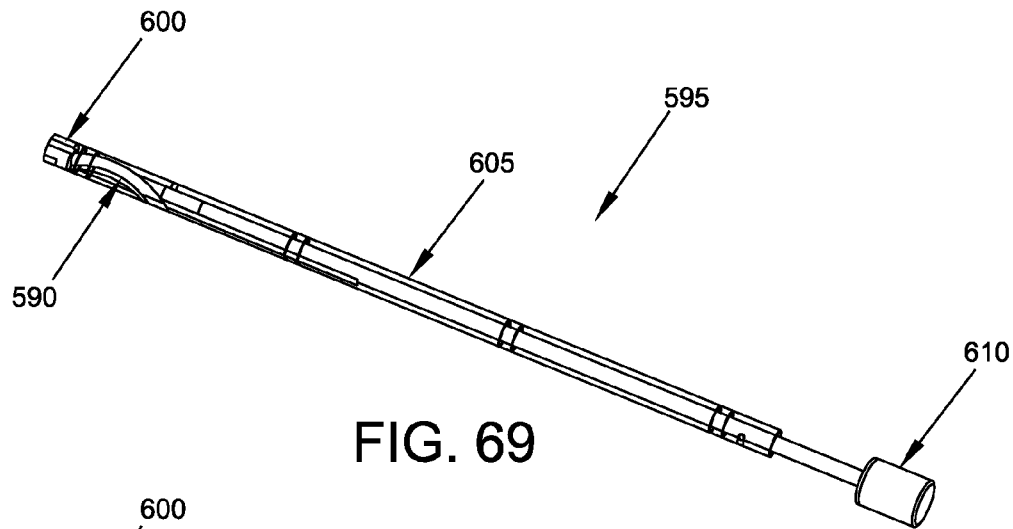
FIGS. 69-73 are schematic views showing apparatus for use with the novel fracture fixation shown in FIG. 68.
Figure 70:
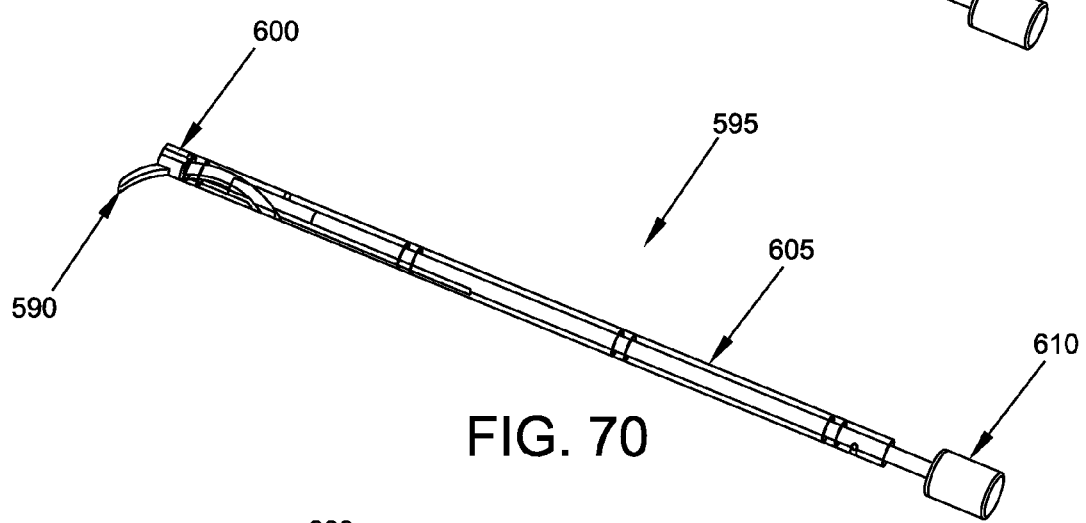
Figure 71:
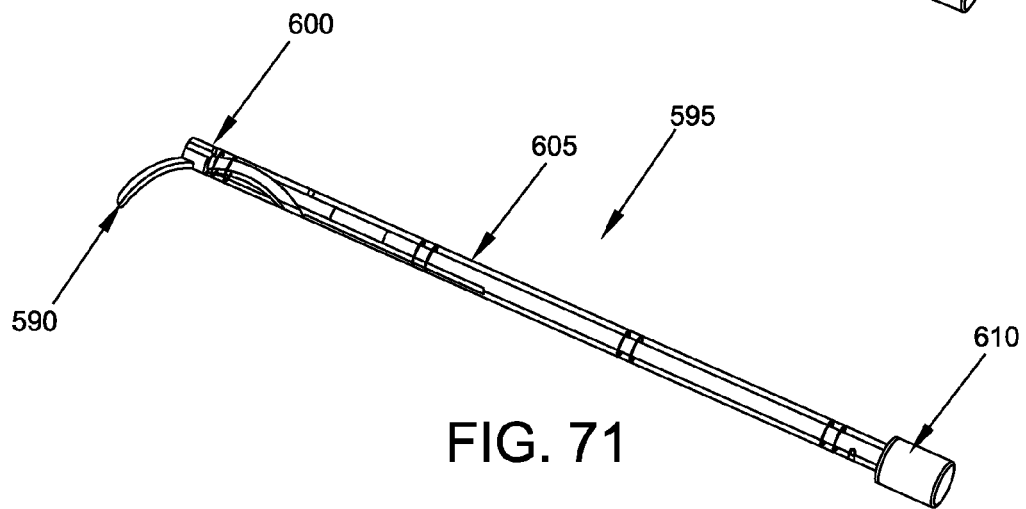
Figure 72:
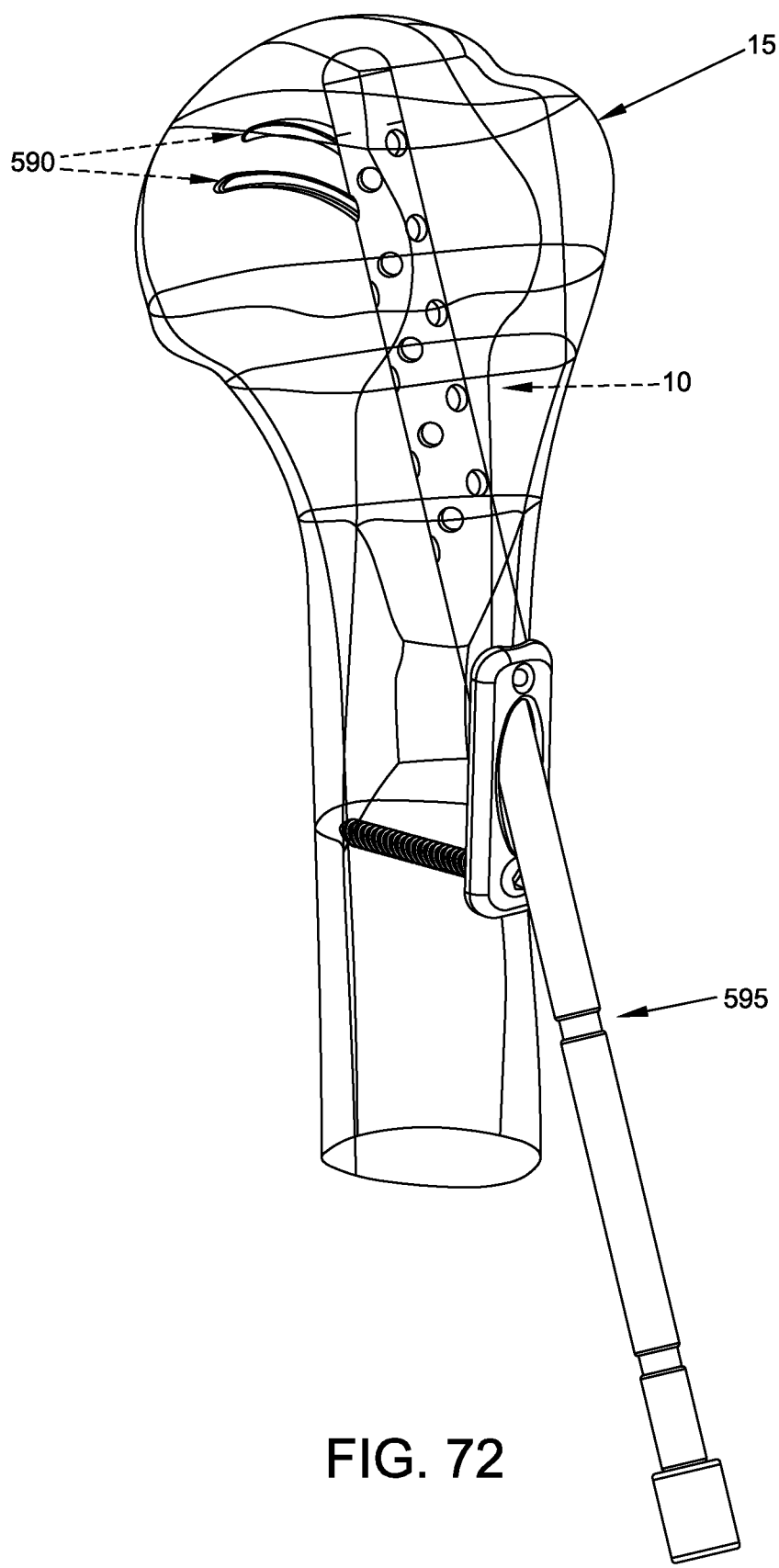
Figure 73:
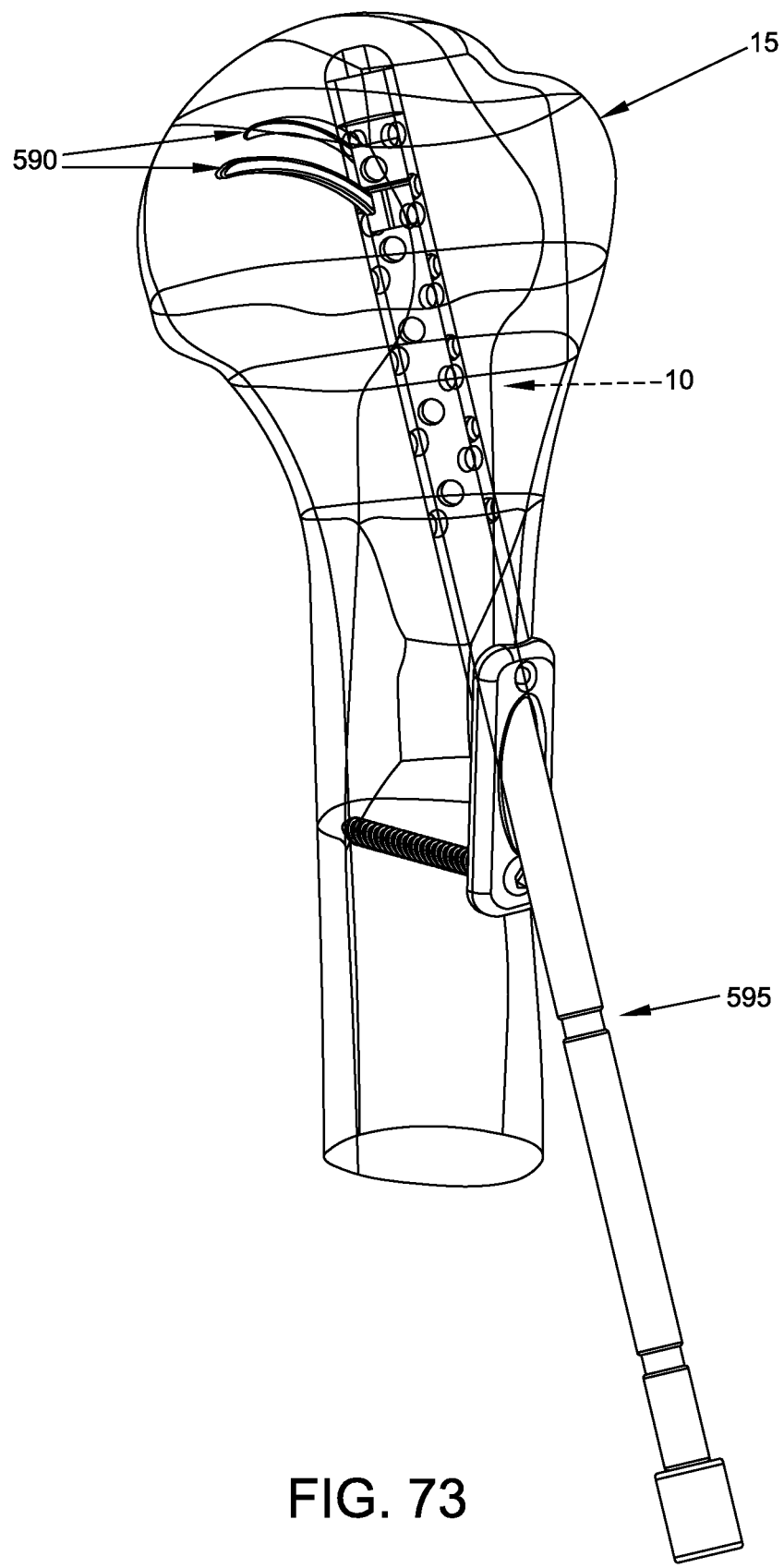

The primary differences between novel fracture fixation apparatus 585 and novel fracture fixation apparatus 5 are (i) the substitution of projecting barbs 590 in place of suture assemblies 20, and (ii) the provision of a deployment mechanism 595 for deploying projecting barbs 590 out of anchoring tube 10. More particularly, projecting barbs 590 are secured to a mount 600, and deployment mechanism 595 comprises a tube 605 and a plunger 610. As seen in FIGS. 69-71, mount 600 is releasably carried by tube 605, with projecting barb 590 being disposed in tube 605 distal to plunger 610. Distal movement of plunger 601 within tube 605 causes projecting barbs 590 to advance distally and proximally out of mount 600 and, at the limit of its throw, to separate mount 600 from tube 605.

As a result of this construction, and looking now at FIGS. 68-73, deployment mechanism 595 can be used to carry mount 600 and projecting barbs 590 into the anchoring tube 10, then cause projecting barbs 590 to advance distally and proximally out of mount 600 and through holes 50 of anchoring tube 10 and into adjacent bone and, at the limit of its throw, to separate mount 600 from tube 605. Mount 600 makes a friction fit with the surrounding anchoring tube 10 to securely seat therein. As a result of the foregoing, projecting barbs 590 are able to secure bone fragments to anchoring tube 10 and, as a result, to proximal humerus 15.

Figure 74:
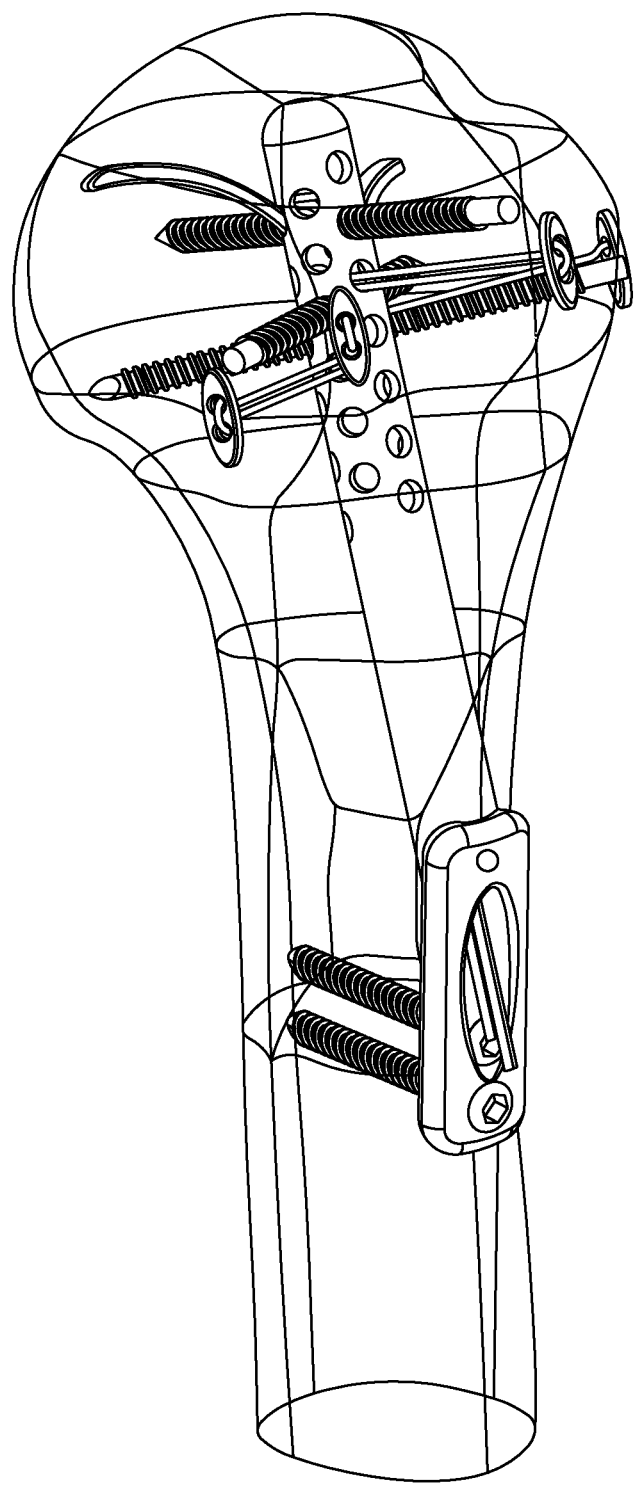
FIG. 74 is a schematic view showing fracture fixation in the proximal humerus using yet another novel fracture fixation apparatus formed in accordance with the present invention.

Fracture Fixation with Various Combinations of Suture Assemblies, Threaded Pins (or Bone Screws) and/or Projecting Barbs It should be appreciated that anchoring tube 10 may be used with various combinations of suture assemblies 20, threaded pins 535 (or bone screws 580) and/or projecting barbs 590, as preferred by the physician. Thus, for example, and looking now at FIG. 74, there is shown a fracture fixation utilizing a plurality of suture assemblies 20, threaded pins 535 and projecting barbs 590.

Use of the Present Invention for Fracture Fixation in Applications Other than the Proximal Humerus It should also be appreciated that the present invention may be used for fracture fixation in applications other than the proximal humerus. By way of example but not limitation, the present invention may be used for fracture fixation in the femur.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method, for treating a bone fracture, the method comprising:
providing an apparatus comprising:
an anchoring tube comprising a hollow elongated shaft adapted for disposition in a hole formed in a bone and having a distal end, a proximal end and a lumen extending therebetween, and a substantially planar plate mounted to the proximal end of the hollow elongated shaft and adapted for disposition against the outer surface of the bone;
wherein the hollow elongated shaft comprises at least two diametrically-opposed holes extending therethrough;
a suture assembly; and
a buckle holder for holding a buckle while a suture is secured to the buckle, wherein the buckle has two holes therein and a slot connecting one of the holes to an end of the buckle, the buckle holder comprising a body having a proximal end, a distal end, a top surface and a bottom surface, a pair of holes extending from the top surface to the bottom surface, a buckle seat adjacent the distal end and extending proximally, and a vertical slot opening on the distal end and extending proximally, the vertical slot extending between the top surface and the bottom surface, the buckle holder being sized so that the buckle seat can receive the buckle, with the two holes in the buckle being aligned with the two holes in the buckle holder;
forming a hole in the bone;
positioning the hollow elongated shaft of the anchoring tube in the hole in the bone; and
extending the suture assembly through a bone fragment, through at least one of the diametrically-opposed holes in the hollow elongated shaft, and through the lumen of the anchoring tube, the suture assembly securing the bone fragment to the anchoring tube under tension, thereby securing the bone fragment to the bone receiving the anchoring tube.

2. A method according to claim 1 wherein the buckle seat comprises a recess opening on the distal end of the buckle holder and extending proximally.

3. A method according to claim 2 wherein the recess comprises a horizontal slot opening on the distal end of the buckle holder and extending proximally.

4. A method for treating a bone fracture, the method comprising:
providing an apparatus comprising:
an anchoring tube comprising a hollow elongated shaft adapted for disposition in a hole formed in a bone and having a distal end, a proximal end and a lumen extending therebetween, and a substantially planar plate mounted to the proximal end of the hollow elongated shaft and adapted for disposition against the outer surface of the bone;
wherein the hollow elongated shaft comprises at least two diametrically-opposed holes extending therethrough; and
a suture assembly;
forming a hole in the bone;
positioning the hollow elongated shaft of the anchoring tube in the hole in the bone;
extending the suture assembly through a bone fragment, through at least one of the diametrically-opposed holes in the hollow elongated shaft, and through the lumen of the anchoring tube, the suture assembly securing the bone fragment to the anchoring tube under tension, thereby securing the bone fragment to the bone receiving the anchoring tube; and rotating the anchoring tube about the longitudinal axis of the hollow elongated shaft while a convex bottom surface of the substantially planar plate maintains supporting contact with the outer surface of the bone.

5. A method according to claim 4, further comprising after the anchoring tube has been rotated about the longitudinal axis of the hollow elongated shaft, extending a fixation element through another bone fragment and at least one of the two diametrically-opposed holes.

6. A method according to claim 5 wherein the fixation element comprises another suture assembly for securing the another bone fragment to the anchoring tube under tension, thereby securing the another bone fragment to the bone receiving the anchoring tube.

7. A method according to claim 5 wherein the fixation element comprises a pin for securing the another bone fragment to the anchoring tube, thereby securing the another bone fragment to the bone receiving the anchoring tube.

8. A method according to claim 7 wherein the pin is threaded.

9. A method according to claim 5 wherein the fixation element comprises a bone screw for securing the bone another fragment to the anchoring tube, thereby securing the another bone fragment to the bone receiving the anchoring tube.

10. A method for treating a bone fracture, the method comprising:
providing an apparatus comprising:
an anchoring tube comprising a hollow elongated shaft adapted for disposition in a hole formed in a bone and having a distal end, a proximal end and a lumen extending therebetween, and a substantially planar plate mounted to the proximal end of the hollow elongated shaft and adapted for disposition against the outer surface of the bone;
wherein the hollow elongated shaft comprises at least two diametrically-opposed holes extending therethrough; and
a suture assembly;
forming a hole in the bone;
positioning the hollow elongated shaft of the anchoring tube in the hole in the bone; and
extending the suture assembly through a bone fragment, through at least one of the diametrically-opposed holes in the hollow elongated shaft, and through the lumen of the anchoring tube, the suture assembly securing the bone fragment to the anchoring tube under tension, thereby securing the bone fragment to the bone receiving the anchoring tube;
wherein a first portion of the suture assembly bears against the bone fragment and a second portion of the suture assembly is secured to the substantially planar plate of the anchoring tube.

11. A method according to claim 10 further comprising extending a fixation element through another bone fragment and at least one of the two diametrically-opposed holes, wherein the fixation element comprises a pin for securing the another bone fragment to the anchoring tube, whereby to secure the another bone fragment to the bone receiving the anchoring tube.

12. A method according to claim 11 wherein the pin is threaded.

13. A method according to claim 10 further comprising extending a fixation element through another bone fragment and at least one of the two diametrically-opposed holes, wherein the fixation element comprises a bone screw for securing the another bone fragment to the anchoring tube, whereby to secure the another bone fragment to the bone receiving the anchoring tube.

14. A method according to claim 10 wherein the suture assembly comprises a buckle mounted to the first portion of the suture assembly, wherein the buckle bears against an outer surface of the bone fragment.

15. A method according to claim 14 wherein the buckle comprises a plate having at least one hole formed therein.

16. A method according to claim 10 wherein the second portion of the suture assembly is secured to the substantially planar plate by a screw which also secures the substantially planar plate to the bone.

17. A method according to claim 10 wherein the substantially planar plate comprises a top surface and a bottom surface, and further wherein the bottom surface of the substantially planar plate is convex, such that when the anchoring tube is disposed in the hole formed in the bone and is rotated about the longitudinal axis of the hollow elongated shaft, the convex bottom surface of the substantially planar plate maintains supporting contact with the outer surface of the bone.

18. A method according to claim 10 wherein the apparatus further comprises at least one pin extending through the at least two diametrically-opposed holes formed in the hollow elongated shaft.

19. A method according to claim 18 wherein the at least one pin is threaded.

20. A method according to claim 10 wherein the apparatus further comprises at least one bone screw extending through the at least two diametrically-opposed holes formed in the hollow elongated shaft.

21. A method according to claim 10 wherein the apparatus further comprises at least one barb extending through at least one hole of the at least two diametrically-opposed holes formed in the hollow elongated shaft.

22. A method according to claim 10 wherein the apparatus further comprises at least one breakaway rod for disposition within the lumen of the hollow elongated shaft, the breakaway rod comprising a distal end, a proximal end, a hole proximal to the distal end for alignment with two of the at least two diametrically-opposed holes formed in the hollow elongated shaft, and a breakaway section proximal to the hole formed in the breakaway rod, wherein the breakaway rod further comprises a plurality of holes formed in the breakaway rod distal to the breakaway section, and a plurality of fixation elements each for extending through a bone fragment, two diametrically-opposed holes in the hollow elongated shaft, and a hole in the breakaway rod.

23. A method according to claim 22 wherein the fixation elements are selected from the group consisting of a pin, a threaded pin and a bone screw.

24. A method according to claim 10, wherein the suture assembly further comprises a suture and a buckle for mounting to the suture, wherein the buckle comprises a plate having two holes formed therein, a bridge extending between the two holes, and a slot connecting one of the two holes to a perimeter of the plate.

25. A method according to claim 24 further comprising a buckle holder for holding the buckle while the suture is secured to the buckle, the buckle holder comprising a body having a proximal end, a distal end, a top surface and a bottom surface, a pair of holes extending from the top surface to the bottom surface, a buckle seat adjacent the distal end and extending proximally, and a vertical slot opening on the distal end and extending proximally, the vertical slot extending between the top surface and the bottom surface, the buckle holder being sized so that the buckle seat can receive the buckle, with the two holes in the buckle being aligned with the two holes in the buckle holder.

26. A method according to claim 25 wherein the buckle seat comprises a recess opening on the distal end of the buckle holder and extending proximally.

27. A method according to claim 26 wherein the recess comprises a horizontal slot opening on the distal end of the buckle holder and extending proximally.

28. A method according to claim 10, wherein the suture assembly further comprises a suture and a buckle, the buckle comprising means for attaching a closed end of the suture to the buckle without tying.

29. A method for treating a bone fracture, the method comprising:
   providing an apparatus comprising:
      an anchoring tube comprising a hollow elongated shaft adapted for disposition in a hole formed in a bone and having a distal end, a proximal end and a lumen extending therebetween, and a substantially planar plate mounted to the proximal end of the hollow elongated shaft and adapted for disposition against the outer surface of the bone;
      wherein the hollow elongated shaft comprises at least two diametrically-opposed holes extending therethrough;
      a suture assembly;
      a breakaway rod for disposition within the lumen of the hollow elongated shaft, the breakaway rod comprising a distal end, a proximal end, a hole proximal to the distal end for alignment with the at least two diametrically-opposed holes formed in the hollow elongated shaft, and a breakaway section proximal to the hole formed in the breakaway rod; and
      a fixation element for extending through a bone fragment, through two of the at least two diametrically-opposed holes in the hollow elongated shaft, and through the hole in the breakaway rod for securing the bone fragment to the anchoring tube, whereby to secure the bone fragment to the bone receiving the anchoring tube;
   forming a hole in the bone;
   positioning the hollow elongated shaft of the anchoring tube in the hole in the bone;
   extending the suture assembly through a bone fragment, through at least one of the diametrically-opposed holes in the hollow elongated shaft, and through the lumen of the anchoring tube, the suture assembly securing the bone fragment to the anchoring tube under tension, thereby securing the bone fragment to the bone receiving the anchoring tube;
   positioning the breakaway rod within the lumen of the hollow elongated shaft; and
   extending the fixation element through another bone fragment, through two of the at least two diametrically-opposed holes in the hollow elongated shaft, and through the hole in the breakaway rod, the fixation element securing the another bone fragment to the anchoring tube, thereby securing the another bone fragment to the bone receiving the anchoring tube.

30. A method according to claim 29 wherein the fixation element is a pin.

31. A method according to claim 30 wherein the pin is threaded.

32. A method according to claim 29 wherein the fixation element is a bone screw.

* * * * *